United States Patent [19]

Tomei et al.

[11] Patent Number: 5,037,207
[45] Date of Patent: Aug. 6, 1991

[54] LASER IMAGING SYSTEM

[75] Inventors: L. David Tomei; Jogikal Jagadeesh, both of Columbus; Fred Cornhill, Worthington; Inching Chen, Columbus, all of Ohio

[73] Assignee: Ohio State University Research Foundation, Columbus, Ohio

[21] Appl. No.: 174,977

[22] Filed: Mar. 28, 1988

Related U.S. Application Data

[63] Continuation-in-part of Ser. No. 828,651, Feb. 12, 1986, abandoned.

[51] Int. Cl.$^5$ ............................................. G01J 3/10
[52] U.S. Cl. .................................. 356/444; 250/458.1; 356/344; 356/417
[58] Field of Search .............. 356/344, 444, 317, 318, 356/417; 250/458.1, 459.1, 461.1, 461.2

[56] References Cited

U.S. PATENT DOCUMENTS

| | | | |
|---|---|---|---|
| 3,450,455 | 6/1969 | Landre | 356/444 |
| 3,516,746 | 6/1970 | Shibata et al. | 356/319 |
| 3,981,590 | 9/1976 | Perkins | 356/419 |
| 4,107,534 | 8/1978 | Piltingsrud | 250/368 |
| 4,523,799 | 6/1985 | Delhaye | 350/6.3 |
| 4,586,781 | 5/1986 | Gunther et al. | 350/3.7 |
| 4,758,727 | 7/1988 | Tomei et al. | 250/461.2 |

FOREIGN PATENT DOCUMENTS

| | | |
|---|---|---|
| 0123942 | 11/1984 | European Pat. Off. |
| 0155813 | 9/1985 | European Pat. Off. |

OTHER PUBLICATIONS

Nicoll, F., "Mural Television Display Using Fiber Optics", RCA Technical Notes (RCA TN No. 188, 1958).
Dyer et al., "Vidicon Microscope for Counting Fluorescent Particles", Review of Scientific Instruments, vol. 24, No. 4 (1971), p. 508.
Slomba et al., "A Laser Flying Spot Scanner for Use in Automated Fluorescence Antibody Instrumentation", Journal of the Association for the Advancement of Medical Instrumentation, vol. 6, No. 3, May-Jun. 1972.
Bussini et al., "A Silicon Rubber Scintillation Compound for Complex Geometry Radiation Detectors", Nuclear Instruments and Methods, No. 2, (1973), pp. 333-335.
"The New FACS 400 Series, FACS 440, FACS 420, FACS 400, Fluorescence Activated Cell Sorting", Becton Dickenson FACS Systems, 1981.
"The FACS Analyzer Fluorescence and Volume Cell Analysis" Brochure, Becton Dickenson FACS Systems, 1982.
Young et al., IEEE Transactions on Biomed. Engineering, BME-29;2, 1983.
Shoemaker et al., IEEE Transactions on Biomed. Engineering, BME-33, 1984.
"Photodigitizing with PDS Microdensitometer Systems" Brochure, Perkin-Elmer, not dated.

(List continued on next page.)

Primary Examiner—Richard A. Rosenberger
Attorney, Agent, or Firm—Emch, Schaffer, Schaub & Porcello Co.

[57] ABSTRACT

A laser imaging system is disclosed which provides the versatility of wide field digital imaging with enhanced spatial resolution and light gathering efficiency. The system will scan targets of any size, dependent only upon the data retrieval and storage limitation of the computer support system, for forward light loss densitometry images as well as fluorescent and forward scatter images. The system is easily adaptable for rare event detection and tracking. The laser system will provide image capture of an entire target within 10 to 60 seconds and controls the scan of the laser beam in three-dimensional pattern and speed. The beam may be repositioned to any one of 16 million locations on a target within an accuracy of +/−0.5 um. Finally, the imaging system of the present invention utilizes a novel optical fiber based detector assembly having NA values of 0.58-0.95 and filters having less than 15% loss at emission wavelengths. Thus, the imaging system of the present invention can capture from 14% to 32% of total fluorescence emission.

11 Claims, 74 Drawing Sheets

OTHER PUBLICATIONS

"Microdensitometer 3 CS" Brochure, Joyce-Loebl, not dated.

"Microdensitometer 6" Brochure, Joyce-Loebl, not dated.

"EIKONIX® Applied Research Software and Product Development Feasibility and Impact Studies Automated Instruments" Brochure, EIKONIX® Corporation, not dated.

"ACAS 470 Workstation" Brochure, Meridian Instruments, Inc., not dated.

"Cytoscan-Cytogenetic Scanning Analyser System" Brochure, Image Recognition Systems, Ltd., not dated.

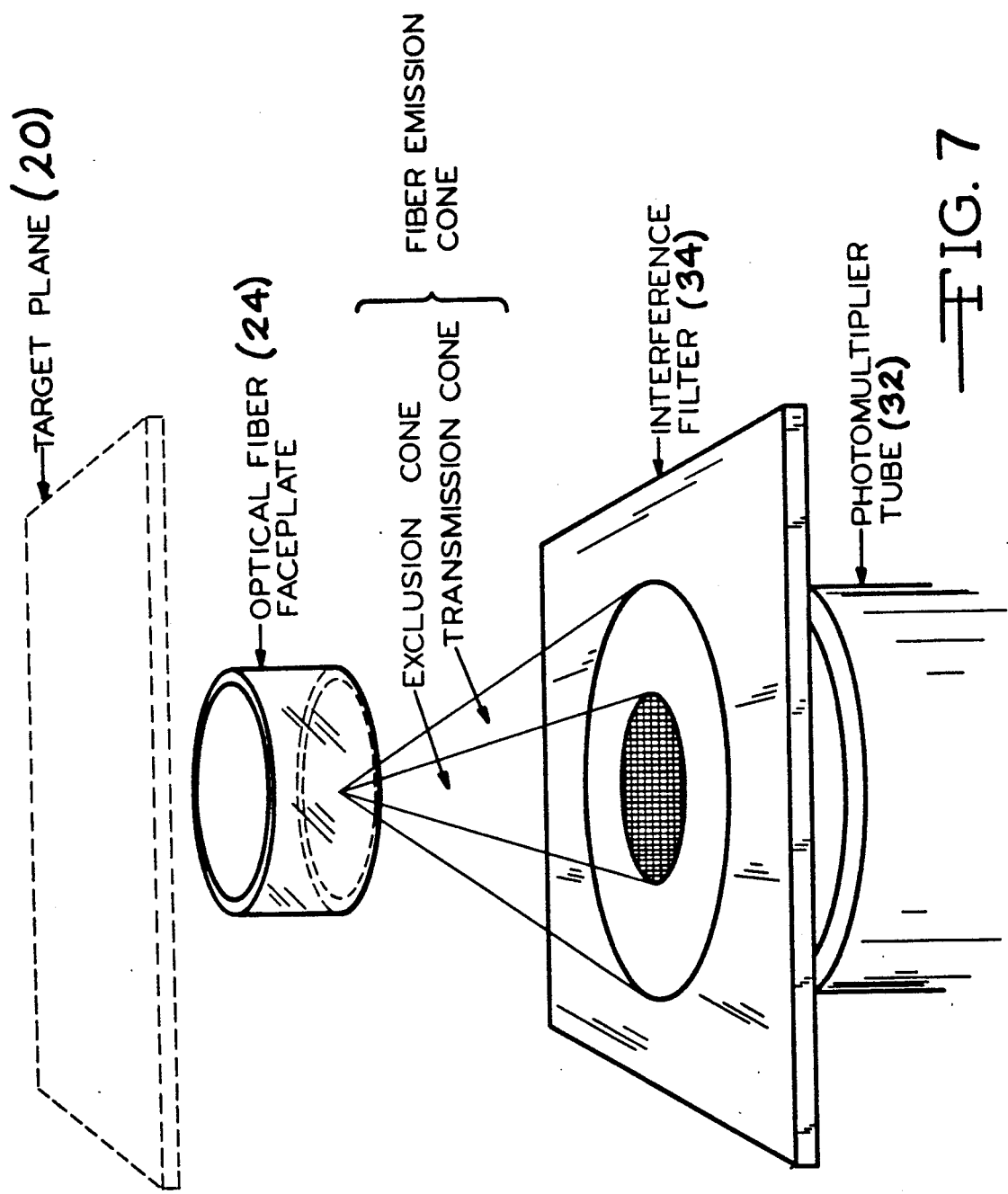

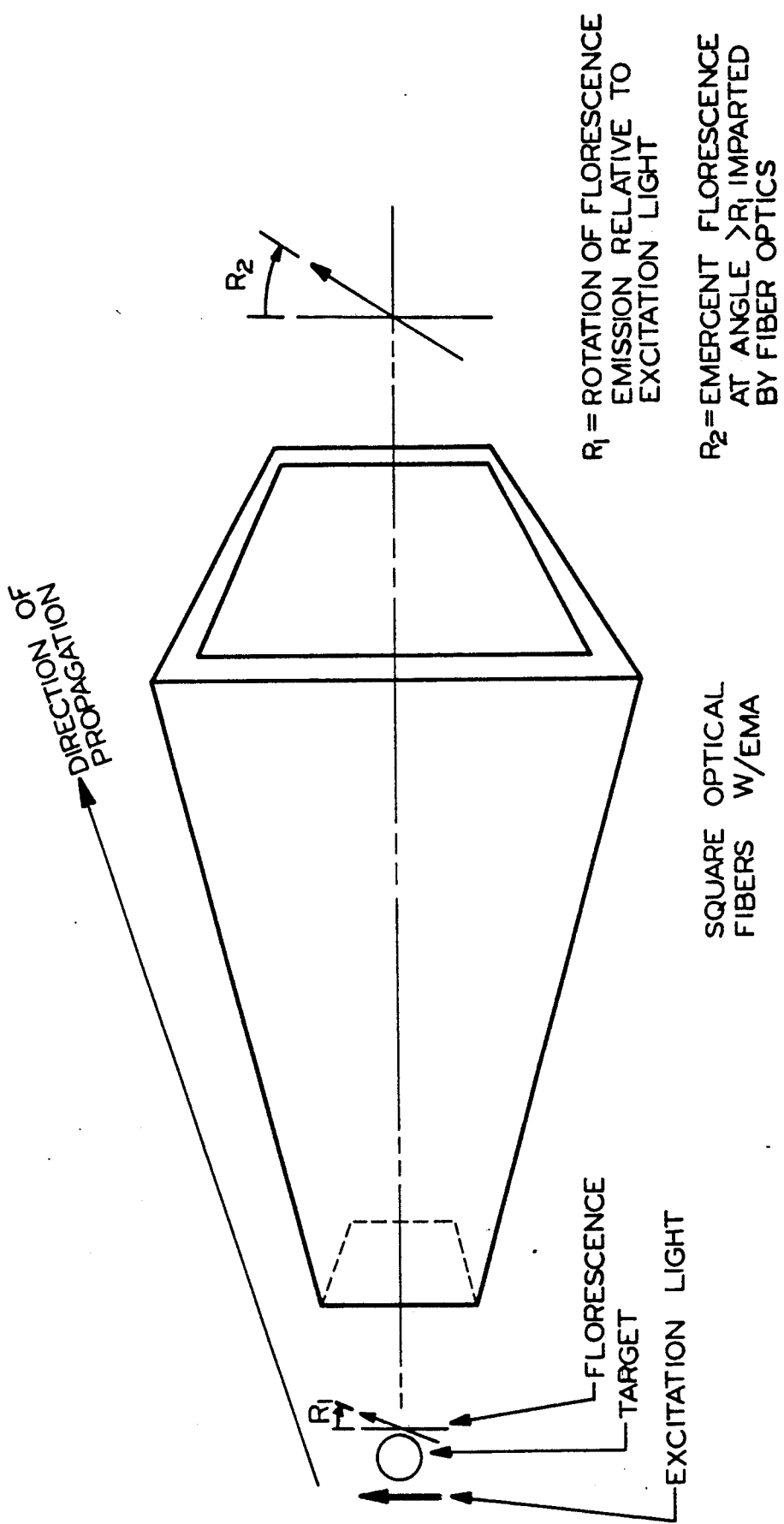

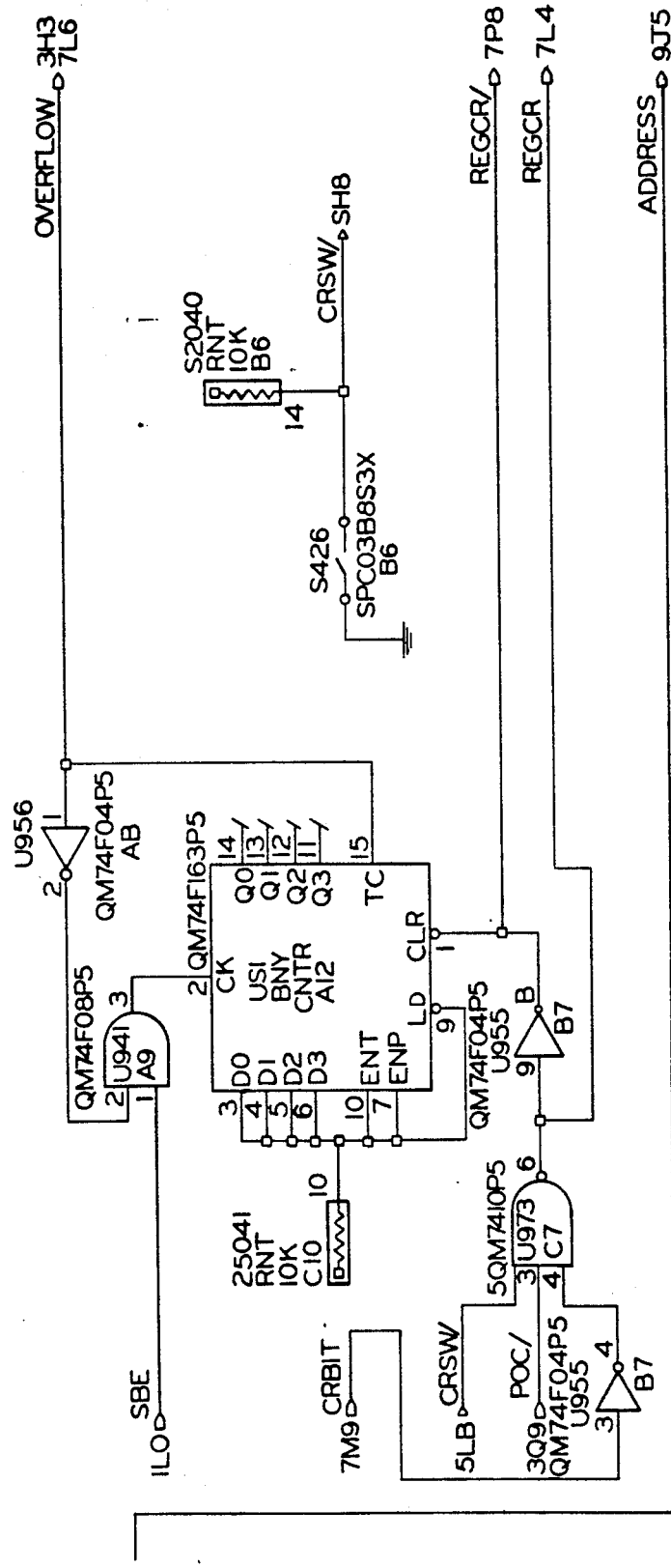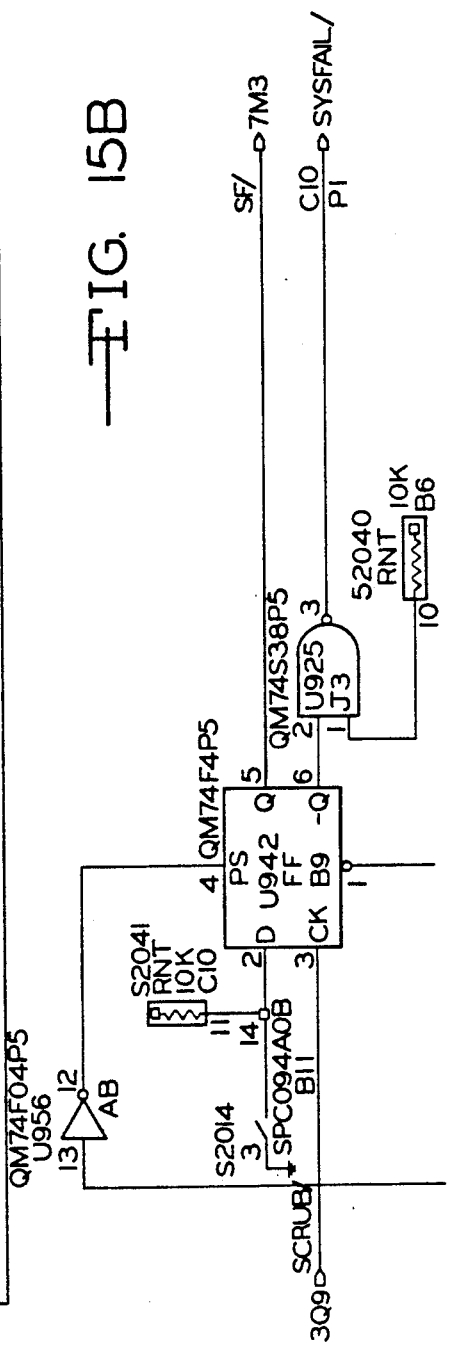
FIG. 15B

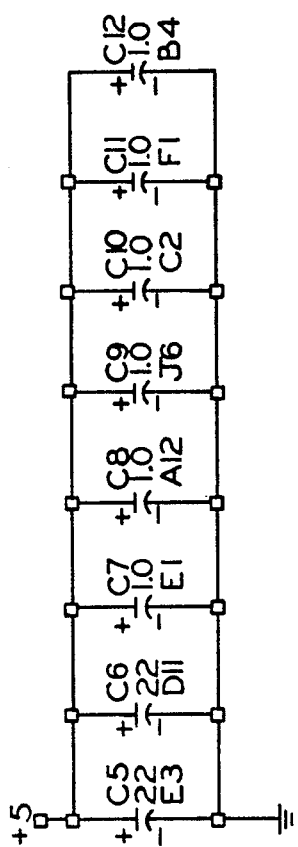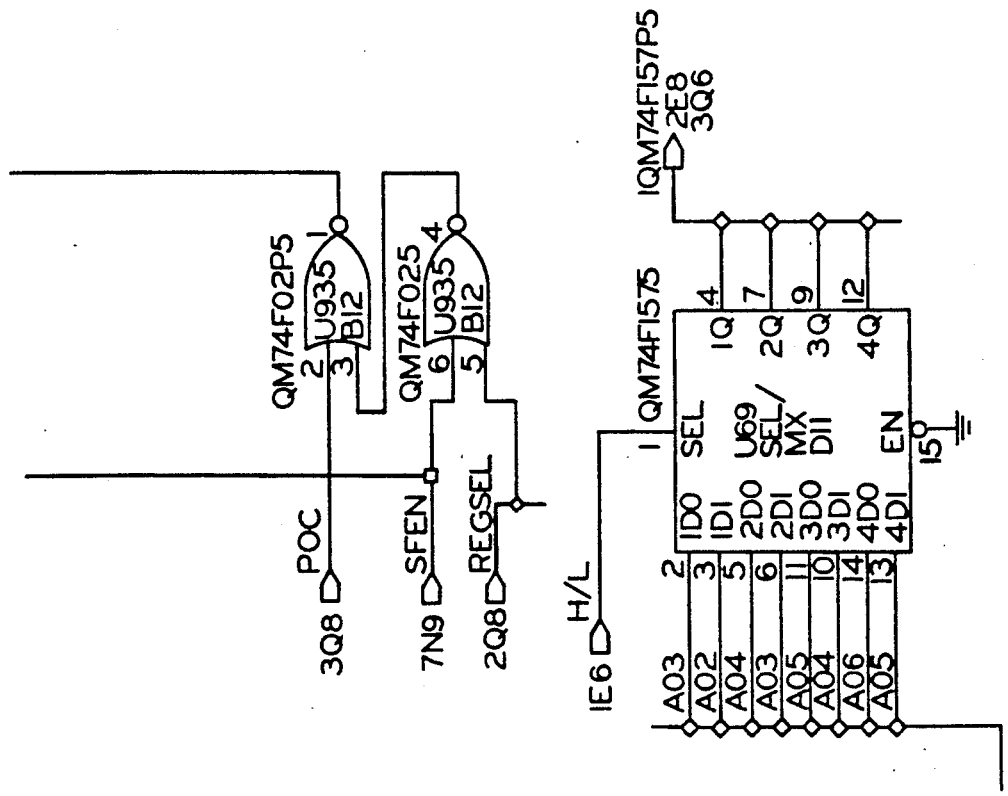
FIG. 15D

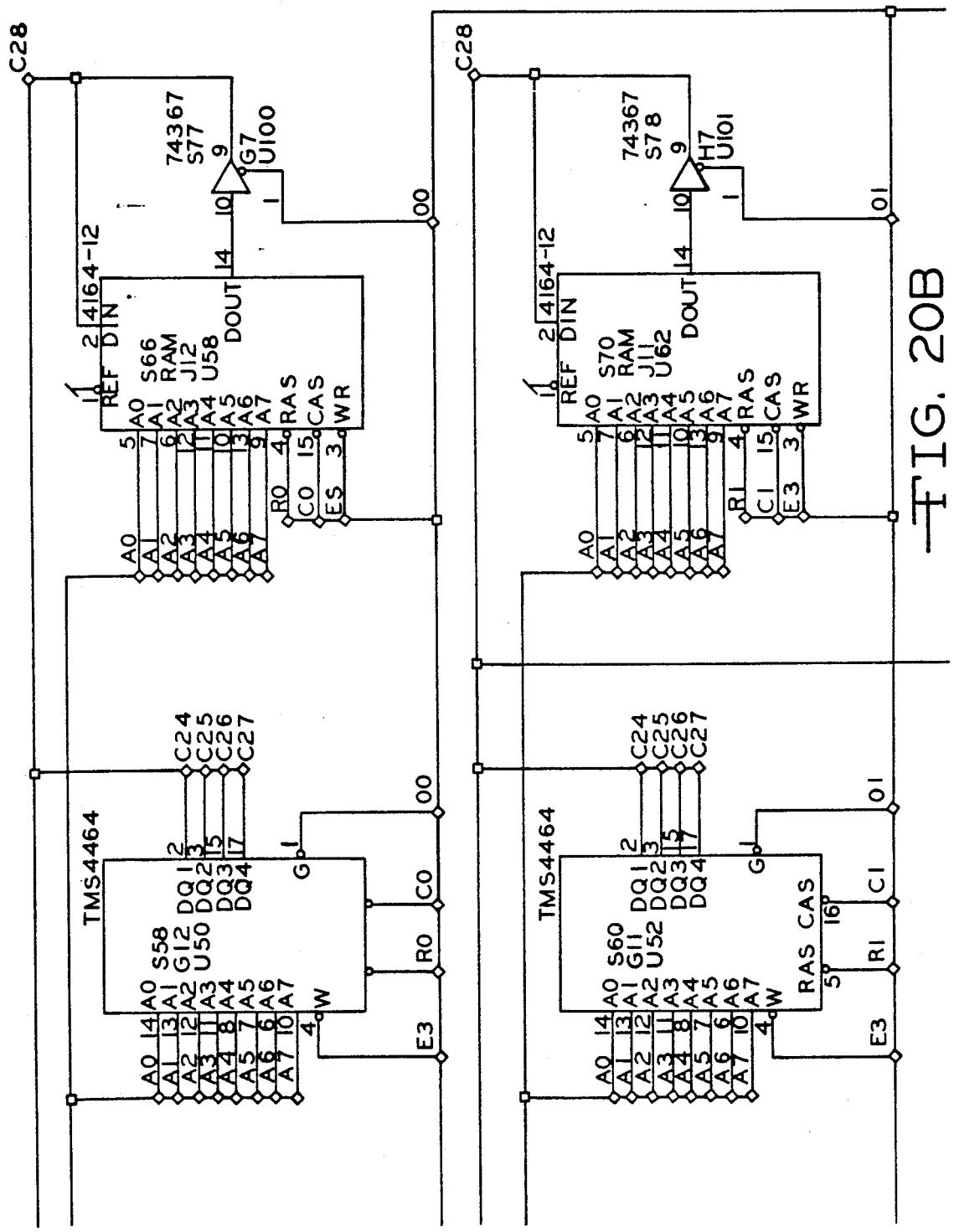

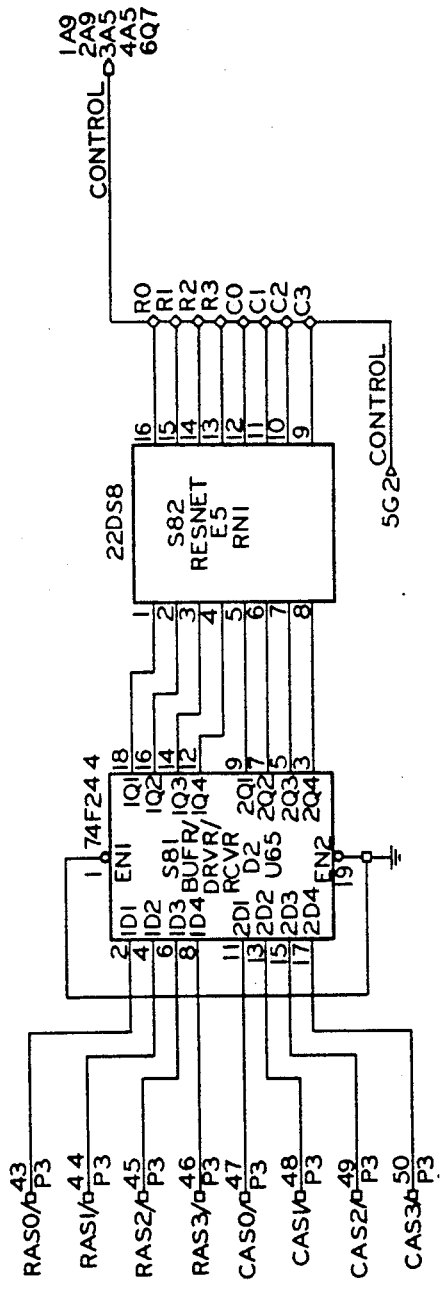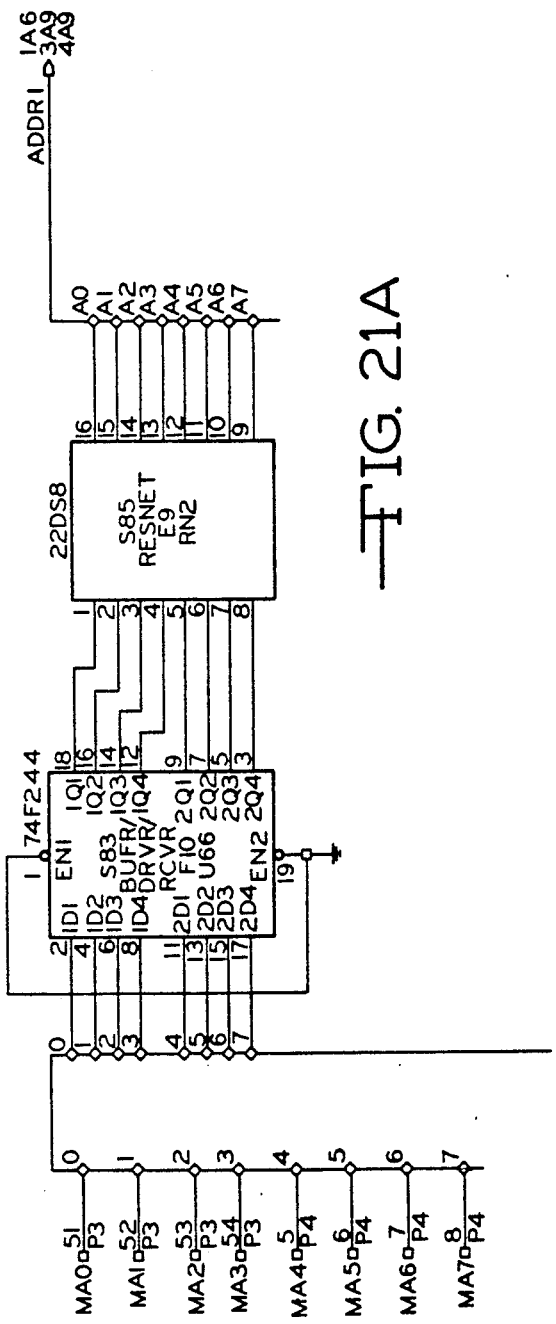
FIG. 21A

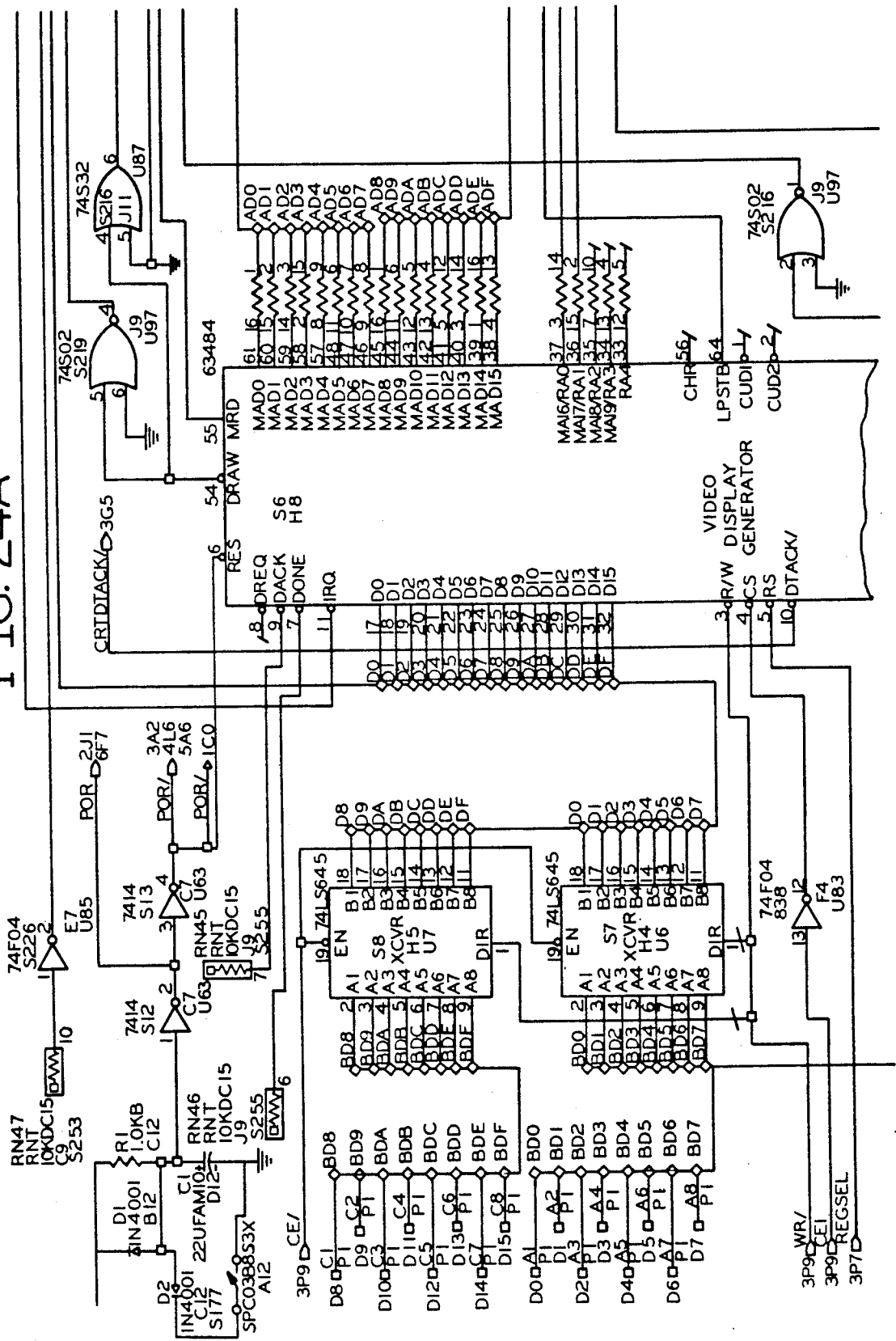

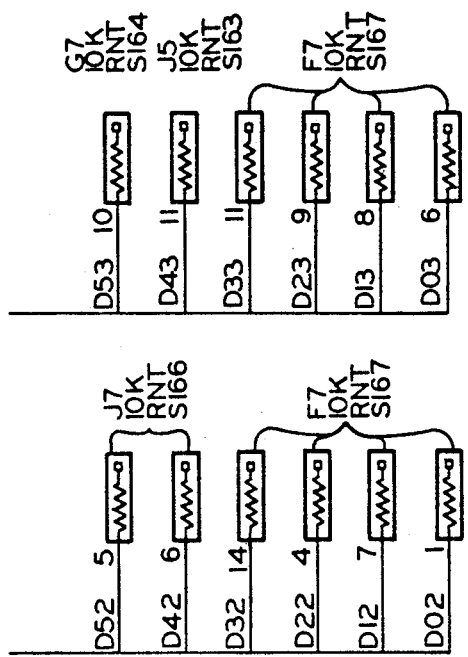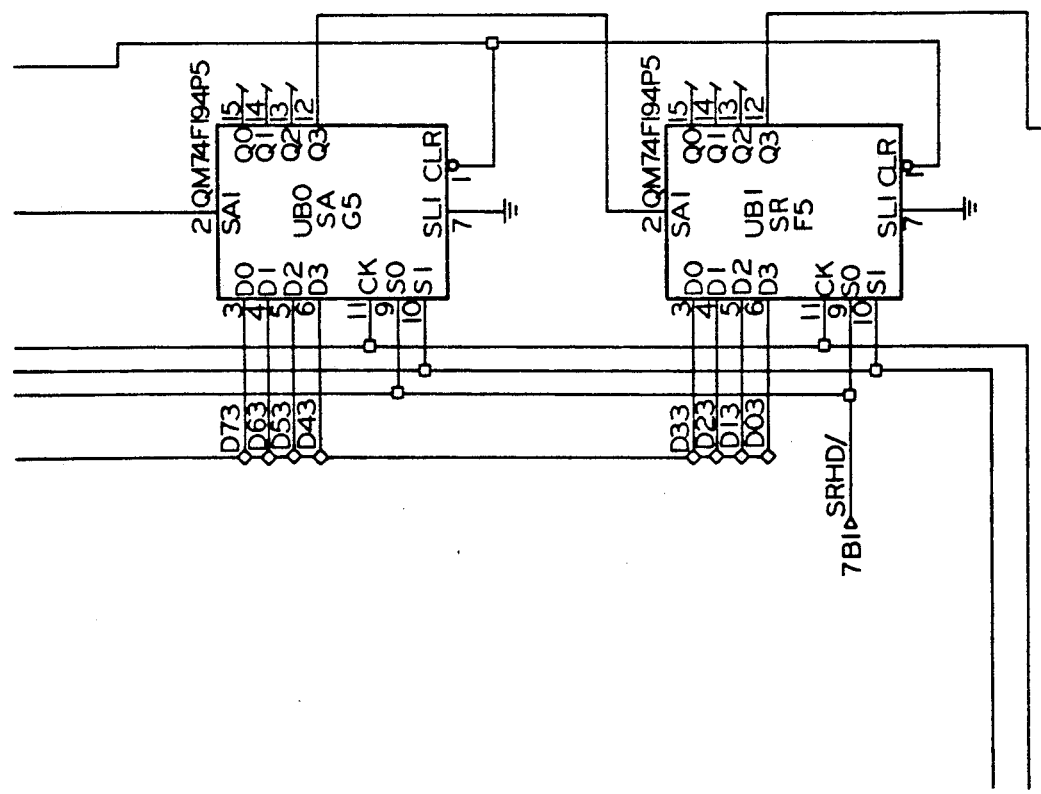
FIG. 28D

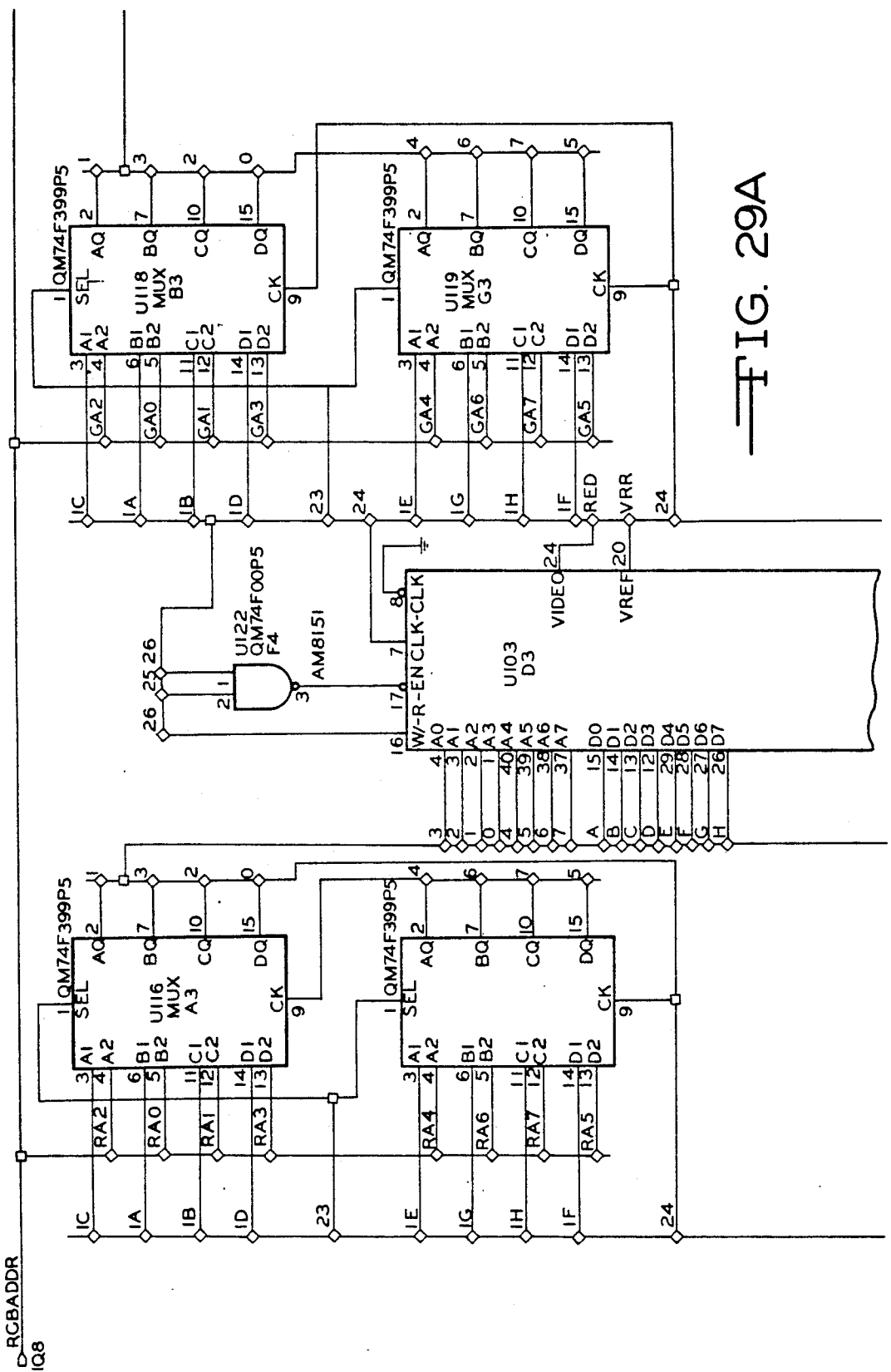

LASER IMAGING SYSTEM

This is a continuation-in-part of copending application Ser. No. 828,651 filed on Feb. 12, 1986, now abandoned.

BACKGROUND OF THE INVENTION

The laser imaging system of the present invention is designed to provide a means for rapid quantitative image capture and digitization where requirements for field size, speed, spatial resolution, dynamic range, and low light sensitivity are not adequately provided for by conventional optical imaging devices.

Specifically, optical devices that incorporate lenses to form a real or virtual image at any point in the system are limited with respect to the target field size, given a particular effective numerical aperture (NA) and spatial resolution. For instance, a microscope provides a means of imaging using lenses of high light gathering power, i.e., high numerical aperture (NA). Typically the value of the NA for an objective lens with 20X is 0.50 (range 0.40-0.75). However, this type of lens is capable of imaging a field of only 3 square millimeters. See for example FIG. 1. If a field of 20 mm×40 mm is to be imaged (approximately the area of a standard microscope slide), then the maximum effective NA for conventional optical lenses would be approximately 0.04-0.10. For this reason highly sensitive fluorescence measuring devices have incorporated microscopes with high NA lenses equipped with mechanical stages to move the target and effect the wide field scan.

Gross mechanical translation of targets such as microscope slides is generally slow and subject to maintenance problems related to wear and failure. The ability of mechanical stages to physically move the target is limited by the need for high positioning accuracy which is typically within 0.5 um. Thus, a high precision autostage will have a maximal translation rate of only about 20 mm/second. Other additional complicating factors involved in image capture require that the mechanical stage stop at each field location long enough for the capture device to electronically transfer the image data to some storage form. Thus, these conventional optical devices, when used for high resolution, low light level scans (e.g., immunofluorescence), can require several hours to capture target fields the size of a standard microscope slide.

If a field of 20 mm×40 mm is to be imaged, then compromises are necessary when using optical lenses. Wide field imaging with effective numerical apertures of 0.9 or higher has led to complex designs and instruments that require hours for image capture. A significant improvement upon these conventional optical devices is the flying spot scanner. However, the flying spot scanners available today including the most recent laser-induced devices, have a significant problem, which is the simple fact that the focal point of the light beam is fixed. Therefore, for a two dimensional scan, the beam spot is found on a curved surface. Correction for this curvature in the present day flying spot scanner requires the incorporation of cumbersome multisided spinning mirrors of complex design. These mirrors afford little control over the location of the laser beam. Conventional flying spot scanners also move the laser in a preprogrammed ballistic direction. The direction and velocity parameters are preprogrammed and the scan cannot be controlled outside of the programming.

Another problem associated with the design of a flying spot scanner for use in fluorescence detection or forward scatter detection is the relatively low efficiency light gathering available using conventional design which use lenses for detection. For instance, a design described by Slomba, et al., (*J. Assoc. Adv. Medical Instr.*, 6:230, 1972) for a flying spot fluorescence detection is capable of capturing less than 1% of the total target emission. This is equivalent to an unacceptable NA of 0.10.

Imaging systems can be designed for a large variety of applications. Generally, however, the requirements of target field size, NA, and spatial resolution dictate specific structures for specific applications. There is little crossover in design for the varying applications. The imaging system of the present invention overcomes the design limitations of current imaging devices and is easily adaptable to perform a large number of imaging operations.

SUMMARY OF THE INVENTION

The laser imaging system of the present invention eliminates the need for mechanical translation stages for targets. The system is capable of scanning targets of any size without gross stage movement subject only to the limitations of available data processing and storage capabilities. The imaging provided by the present invention is based not only upon optical density and forward light loss (FLL) densitometry, but light scatter and fluorescence emission as well. The scanning system can also be programmed to scan for rare event detection and tracking, (i.e., the following of a neutron path in a target). The system will provide image capture of an entire target within 10 to 60 seconds and controls the scan of the laser beam in both pattern and speed. The beam spot may be repositioned to any one of 16 million locations on a target within an accuracy of $+/-0.5$ um. Finally, the imaging system of the present invention utilizes a novel optical fiber based detector assembly having NA values of 0.58-0.95 and filters having less than 15% loss at emission wavelengths. Thus, the imaging system of the present invention can capture from 14% to 32% of total fluorescence emission.

The imaging system is easily adaptable to undertake a large variety of imaging applications. The system will perform Clonogenic Assays and cDNA and genomic DNA imaging. The system will perform multiwell plate assays such as a fluorescence assay from any immobilized immunofluorescence assay system. Another application is the imaging of submicron particles based on scatter characteristics. Other applications include the discrimination of plane polarized fluorescence emissions and qualitative and quantitative imaging of those emissions. The imaging system of the present invention will perform neuroautoradiographs yielding quantitative digital images in neutral density or digital color. Yet another application is the migration inhibition assay using multiwell plates for bone marrow transplantation testing. The imaging system of the present invention will perform 3D Interferometry Surface Profiling for non-contact micro-surface quantitative analysis. Another application for the imaging system is the measurement of scatter or density for a cytochemistry analysis of large sample screening.

The imaging system of the present invention performs opaque gel scanning as well as transparent or semitransparent (i.e., translucent) gel scanning. Scanning densitometry is used to quantitate typical translucent gels such as agarose gels following chemical staining of the DNA, RNA, or protein bound to the gel. However, the high degree of biochemical resolution required for gene sequence analyses has resulted in the development of analytical techniques which involve the electrophoretic transfer of material from translucent separation gels to opaque membranes typically constructed of glass fibers or nylon matrix. The material on these membranes is visualized by introducing a chemical stain to colorimetrically mark the position and amount of the material. The material can also be labeled with a radioactive marker for subsequent analysis using autoradiographic techniques and additional photosensitive elements such as x-ray film. The membrane matrix prevents the use of conventional optical scanning densitometry techniques because of the high light diffusion and attenuation produced by the matrix. This is comparable to a high resolution image located on a single side of heavy photographic paper. The optical fiber detector assembly of the laser imaging system of the present invention collects all light, from the entire scanned area, emitted at angles up to 90° from the optical axis simultaneously at each and every position of the laser spot and assigns the value of the light intensity to that individual position or pixel. Within seconds, this process is performed several million times and a quantitative digital reproduction is obtained of the image on the surface of the stained membrane, photographic paper, or similar target scanned. Since this differs from simple axial light loss or optical density, it is referred to as Forward Light Loss (FLL) scanning.

Finally, the imaging system will perform the scanning of fluorescence shadowing and forward scatter fluorescence shadowing through the use of a fluorescent sensor, thus eliminating the problems of measuring the laser spot size and focusing the spot.

These applications of the present invention are currently known, however, this list is not intended to be limiting upon the range of potential uses for this system.

BRIEF DESCRIPTION OF THE DRAWINGS

FIG. 7 is a conceptical illustration of the detector assembly of FIG. 6.

FIG. 9 is an illustrative schematic of the plane polarization by a square cross-sectional optical fiber of fluorescence emissions.

DESCRIPTION OF THE PREFERRED EMBODIMENT

The laser imaging system of the present invention provides wide field digital imaging with enhanced spatial resolution and light gathering efficiency.

Figure 1:
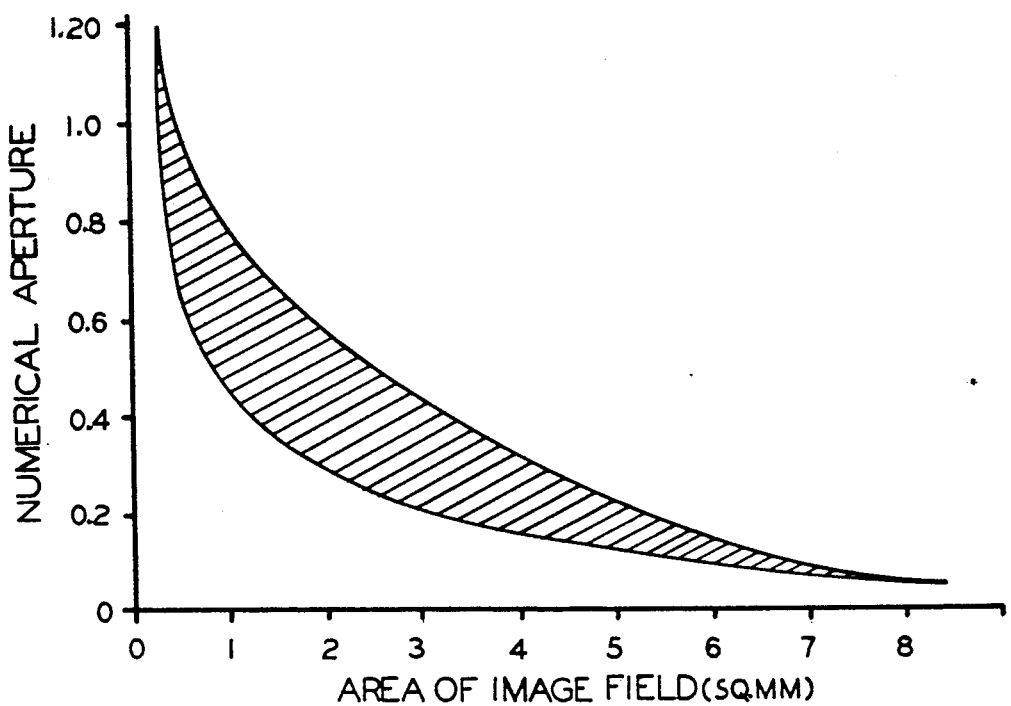
FIG. 1 is a graph showing the relationship of the numerical aperture (NA) and target field image size for conventional lenses.
Figure 2:
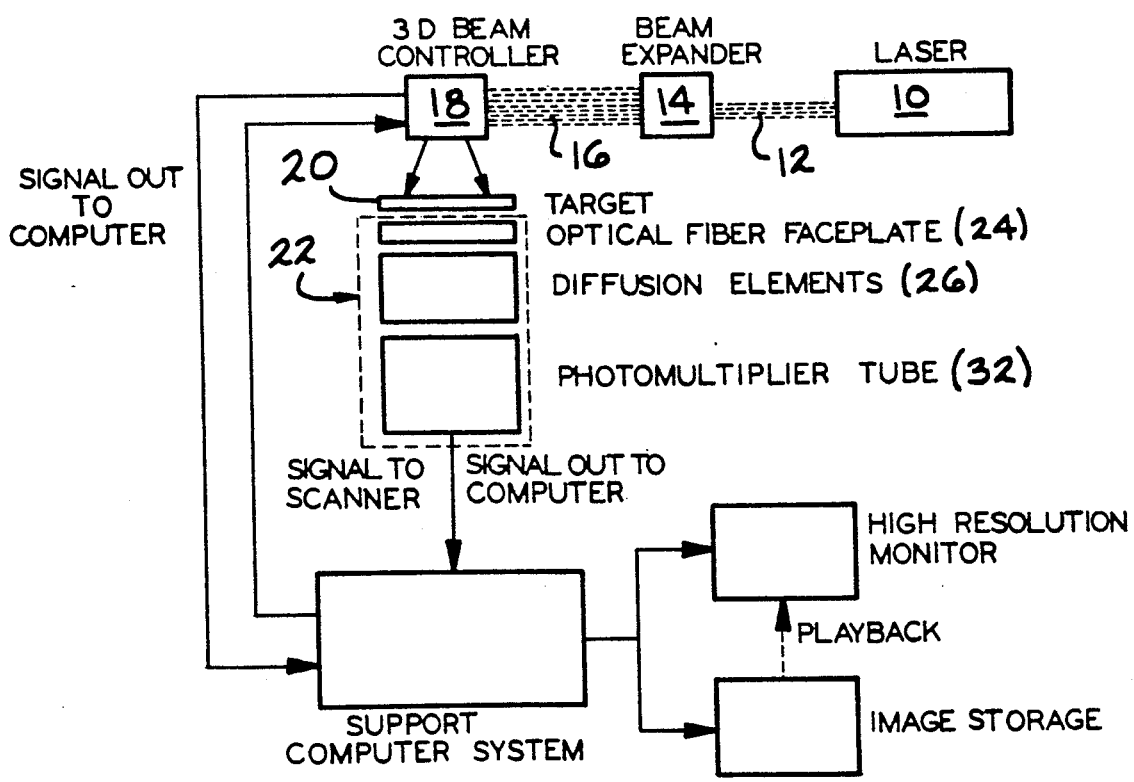
FIG. 2 is a schematic illustration of the laser imaging system of the present invention.
Figure 3:
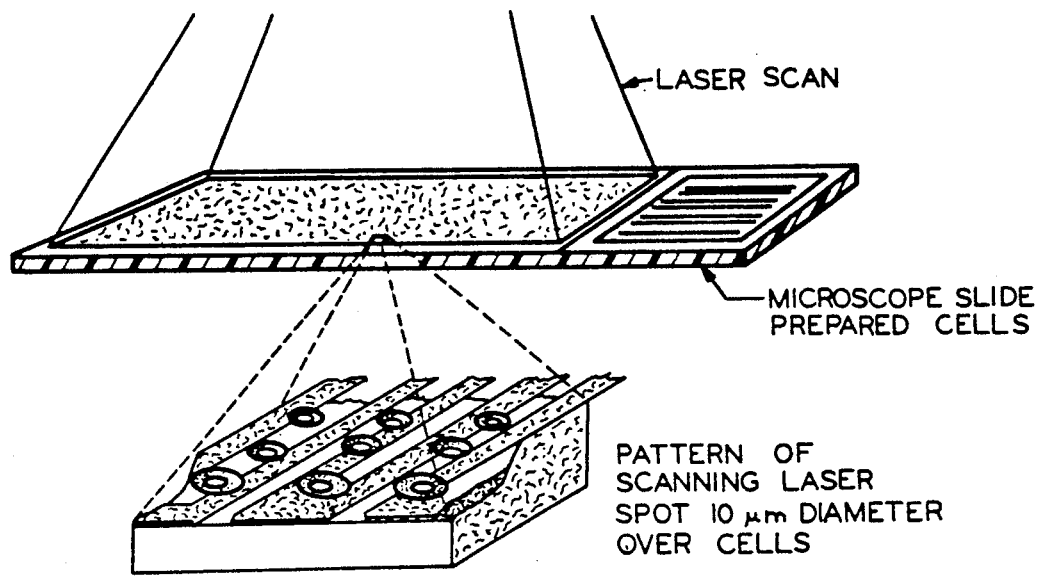
FIG. 3 is an illustrative representation of a typical microscope slide and a pattern of laser scanning the slide.

Referring now to FIG. 2, the optical design used with the imaging system is shown. The primary laser 10, a 25 mW He-Cd, Omnichrome 450X, provides a beam 12 to a beam expander 14 composed of an objective lens and a 50 um spatial filter. The beam 12 exits the beam expander 14 as an input collimated beam 16, 10 mm in diameter. A three dimensional beam position controller 18, manufactured by General Scanning Corp., receives the collimated beam 16.

The beam expander 14 ensures the utilization of the greatest possible surface area of the mirrors of the beam controller 18. The beam 12 from the laser 10 is too small and the beam expander 14 provides an adjustable spot size from 1 mm to 10 mm according to the needs of the controller 18. The beam expander 14 can be modified optically to take advantage of Bessel Function beam characteristics if desired. Such beam characteristics are evidenced by diminishing diffraction rings which circle around the center spot. The optics of the beam expander 14 can be modified by replacement of the spatial filter with a circular disc to block the high energy diffraction rings. Such a modification focuses the imaging beam to a carefully selected spot size without any unwanted spillover.

The beam controller 18 includes an imaging lens (not shown) which produces a 2–10 um diameter spot depending on the diameter of the collimated beam 16. Galvanometrically driven mirrors (not shown) incorporated within the beam controller 18 provide for control over the 2–10 um diameter spot in the X, Y and Z axes as the spot is focused on the target plane 20. The beam controller 18 allows for maximum scanning rates up to 100 Hz or an approximate spot vector rate of 800 cm/sec. Each of the three axes of the beam controller 18 are under individual software control which permits any desired scanning or tracking pattern to be performed. Placement of the laser spot is accurate within +/−0.5 um, thus the laser spot can be fixed on any specified cell in the target 20 area after scanning. Such placement accuracy permits further imaging at a higher resolution and the recording of cell location for further direct examination if desired.

The 3-D beam controller 18 manufactured by General Scanning, Inc., incorporates independent temperature control on all three main galvanometer drives which maintains the temperature at 40 (+/−0.5) degrees C. The upper scanner and lower laser chambers incorporate sensors (not shown) for continuous monitoring of ambient temperature during operation. The He-Cd or Argon-ION laser in the lower chamber is provided with ducted positive ventilation using room air in order to minimize environmental contamination and control the operating temperatures of the optical components.

Figure 4:
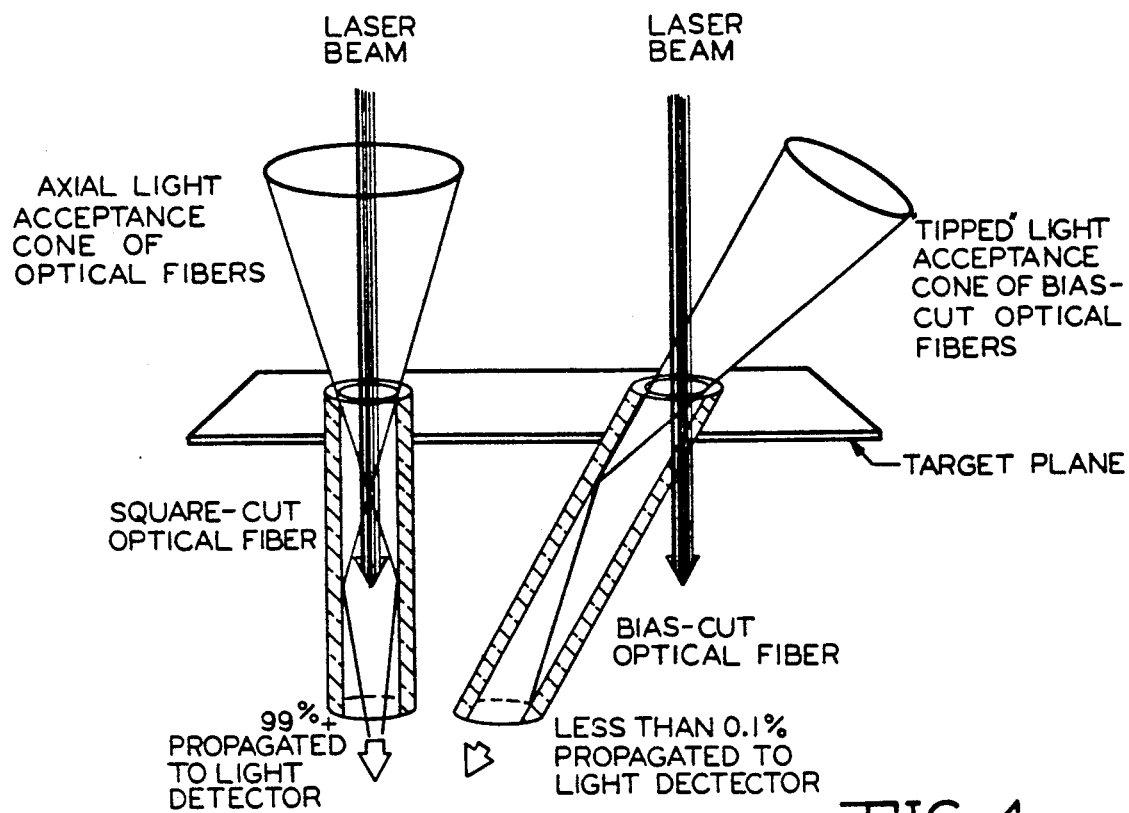
FIG. 4 is an illustrative representation of the light detection properties of a blunt-cut optical fiber faceplate and a bias-cut optical fiber faceplate.

As shown in FIG. 4, the imaging system can scan the entire sample area of a microscope slide of prepared cells which will include 5 million to 20 million cells. The system is driven at rates up to 100 Hz, which means that a single line can be scanned in 0.005 seconds. The system can be programmed to perform either vector scans or raster scans equally efficiently. The X and Y steps are variable from 0.6 um to 40 mm in 0.6 um units. To illustrate the effectiveness of this approach to scanning blood smears, the system is capable of detecting a single positive fluorescent cell on a slide area of 400 sq. mm. (which can include as many as 20 million cells), measure the fluorescence emission level (up to 12 bit resolution), and specify the location of the cell within an accuracy of +/−0.5 um.

The basic detector assembly 22 is comprised of three basic elements: a high numerical aperture optical fiber faceplate 24; a diffusion assembly 26 and a photomultiplier tube (PMT) 32. The basic diffusion assembly 26 includes flashed opal diffusion filters 30 and an internally reflective cylindrical coupling 28. Two basic configurations of the optical fiber faceplate 24 are utilized dependent on whether the imaging is to be based upon light transmission or fluorescence emission within the target.

Figure 11:
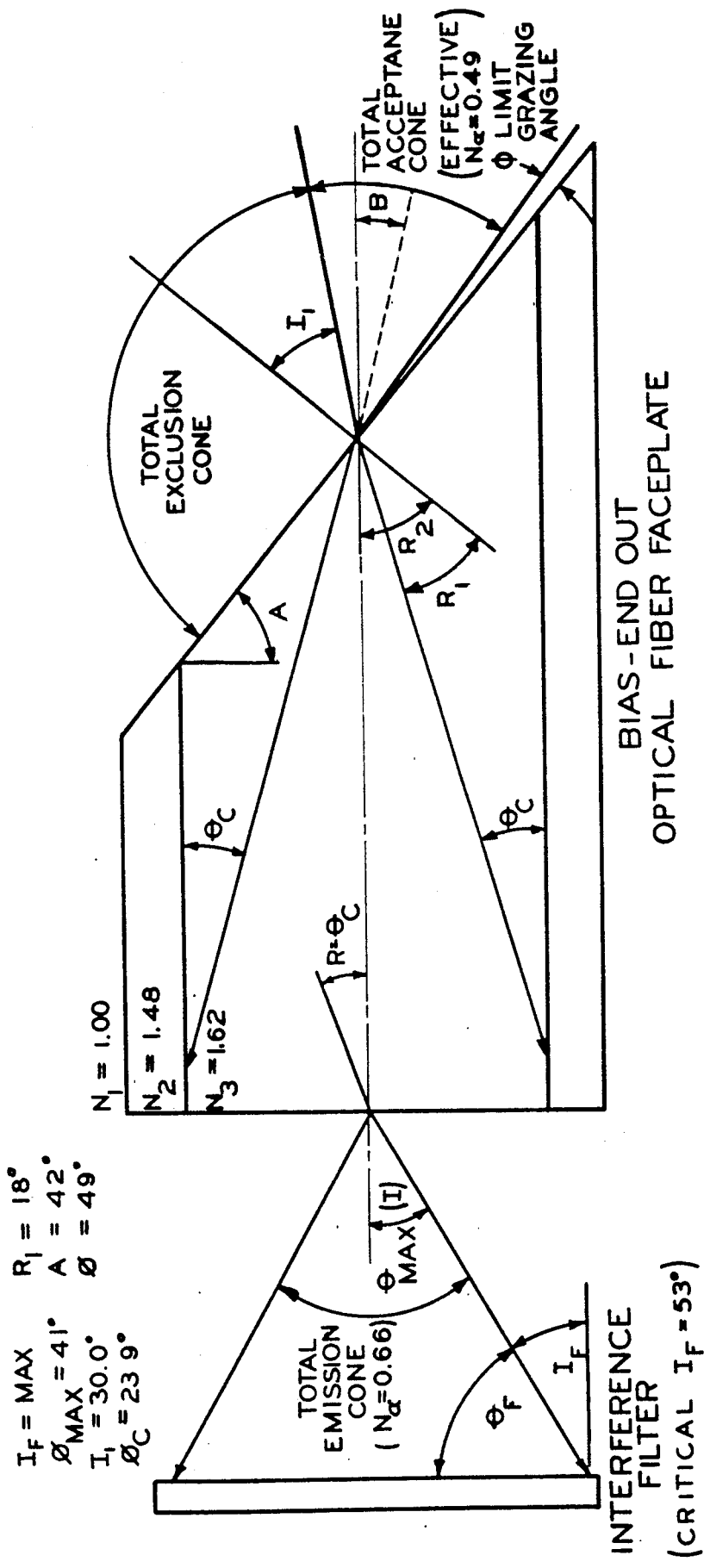
FIG. 11 is a schematic illustration of the light acceptance cone of a bias-cut optical fiber faceplate.
Figure 12A:
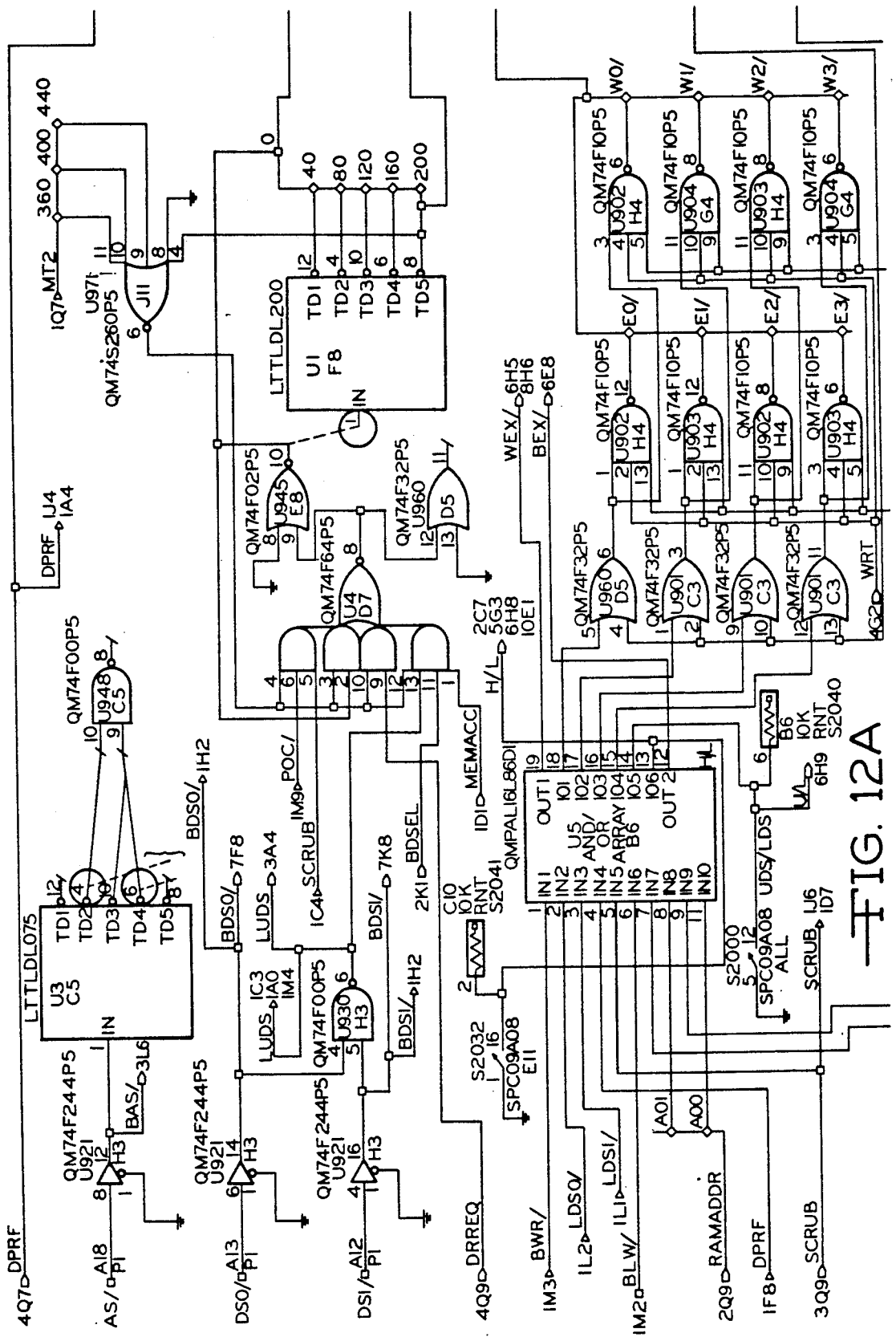
FIGS. 12A, B, C and D are schematics for the Image Memory Controller of the present invention showing the circuitry for the Memory Request Arbiters and the Input/Out Access circuitry.
Figure 12B:
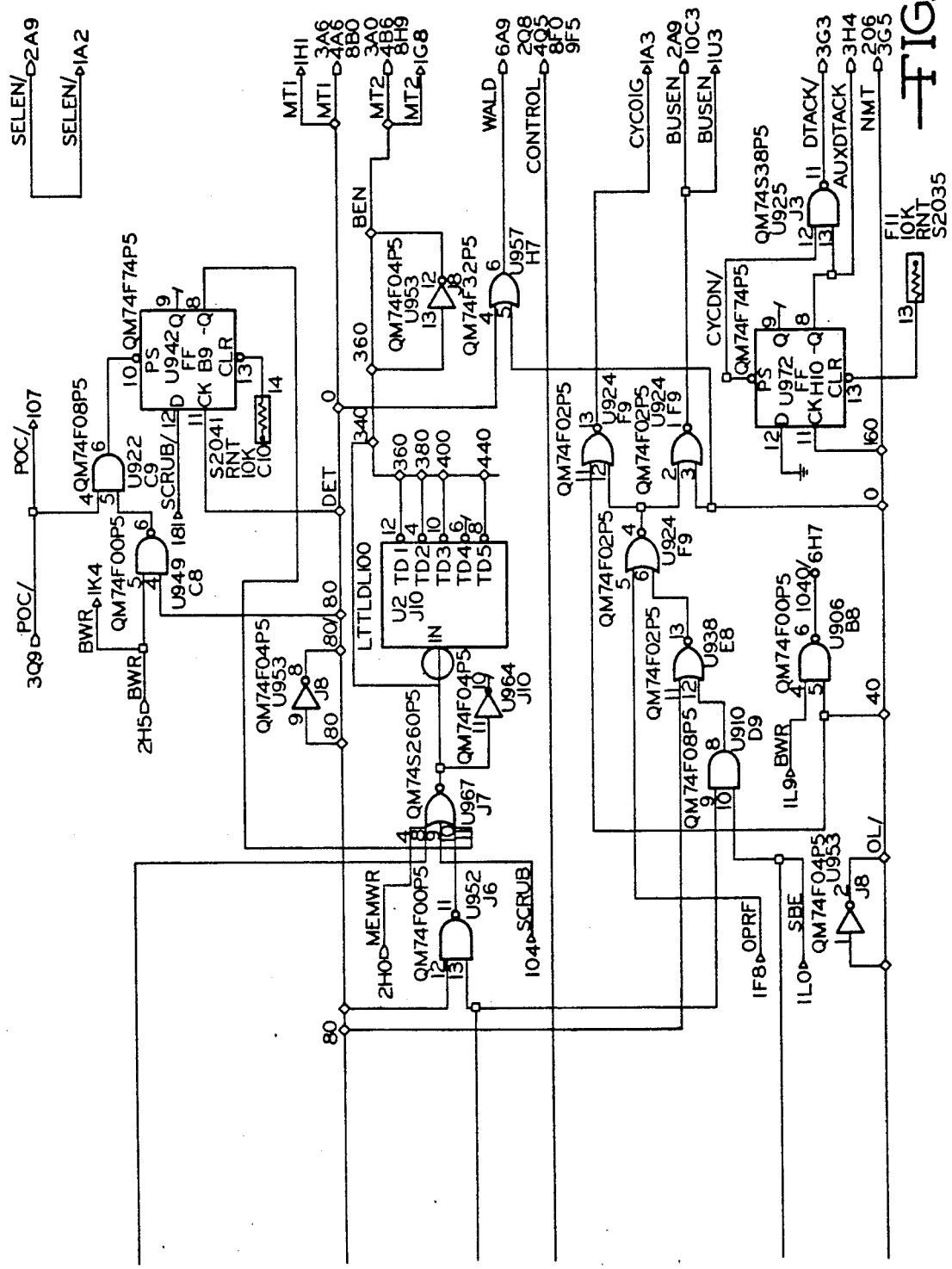
Figure 12C:
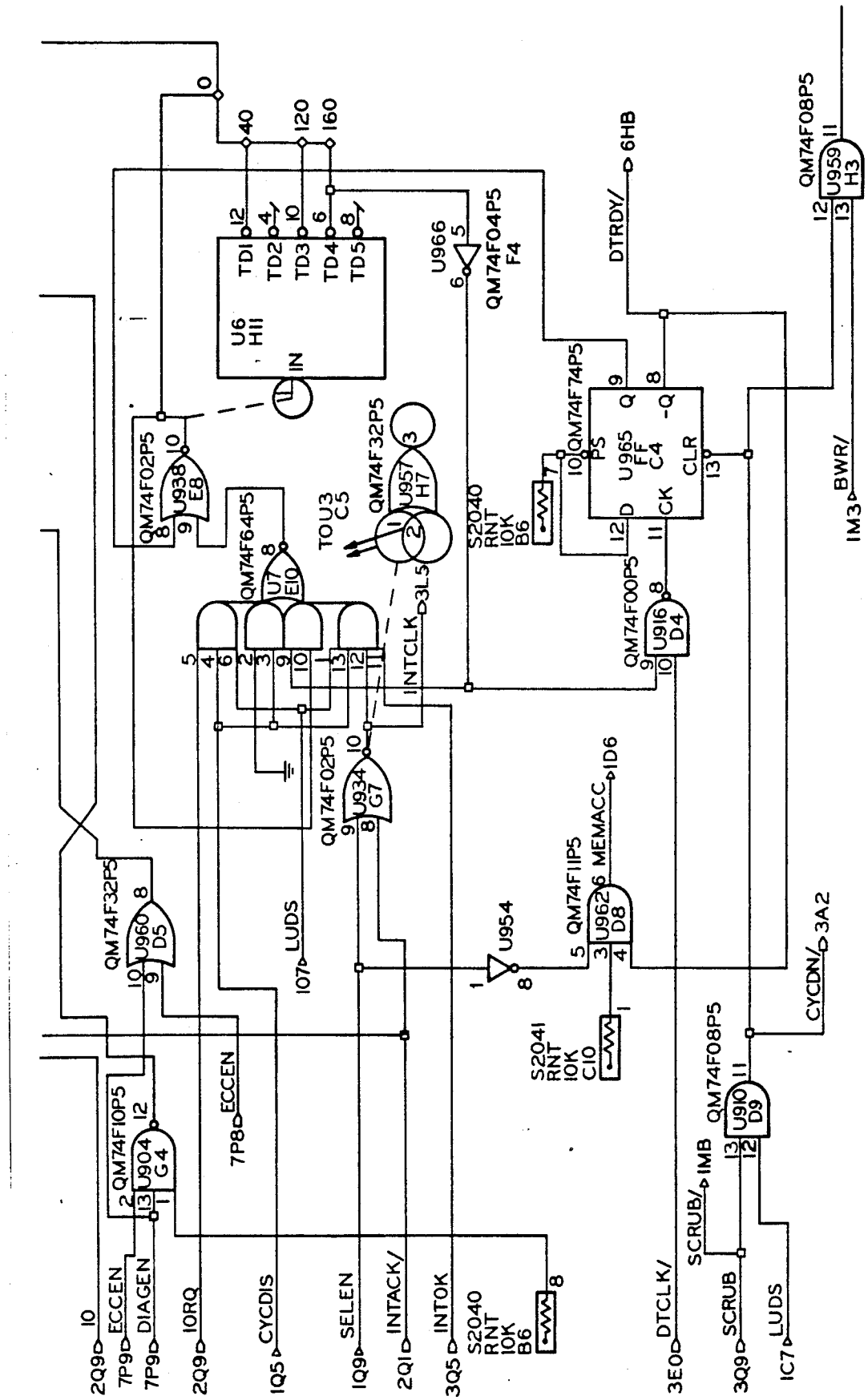
Figure 12D:
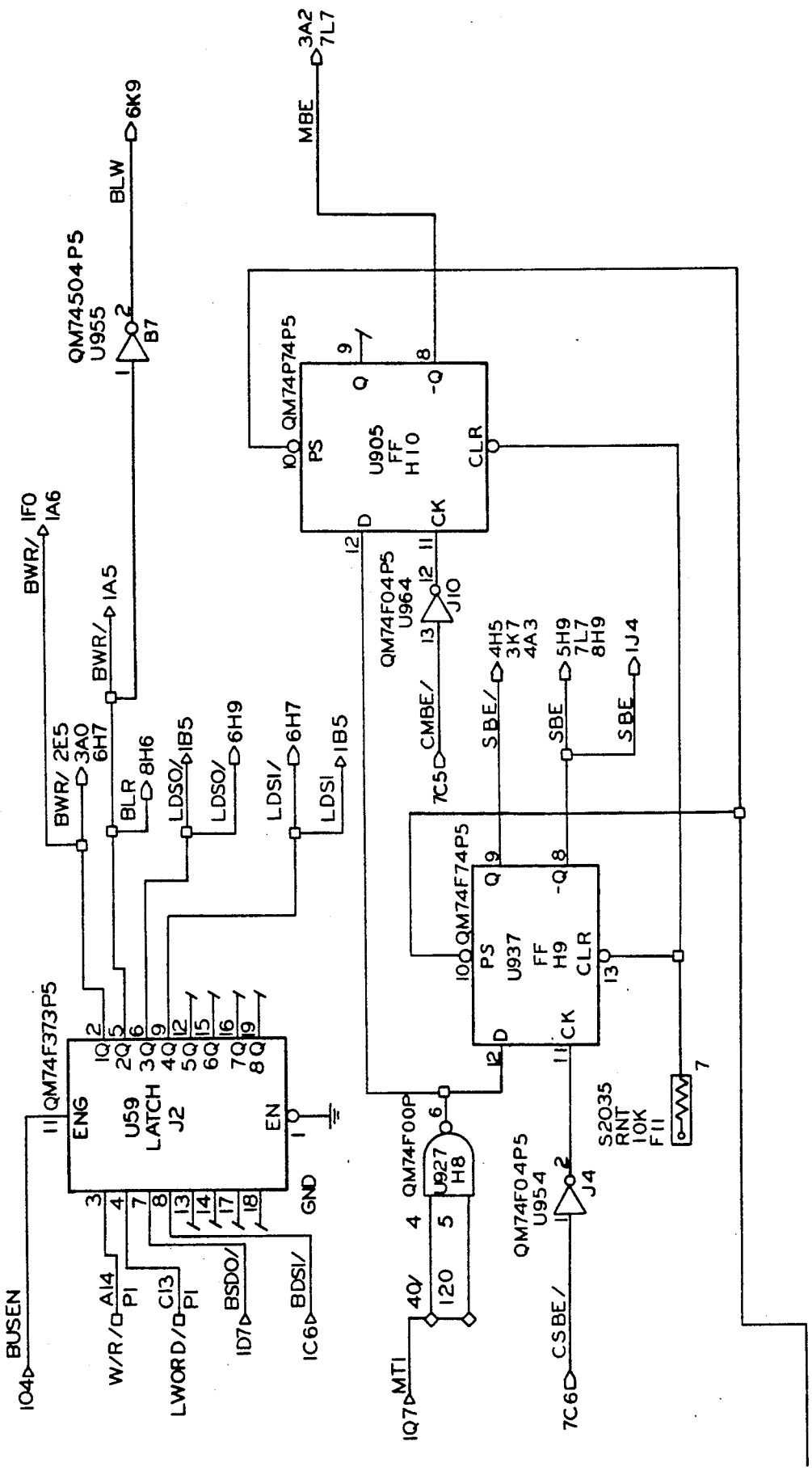
Figure 13A:
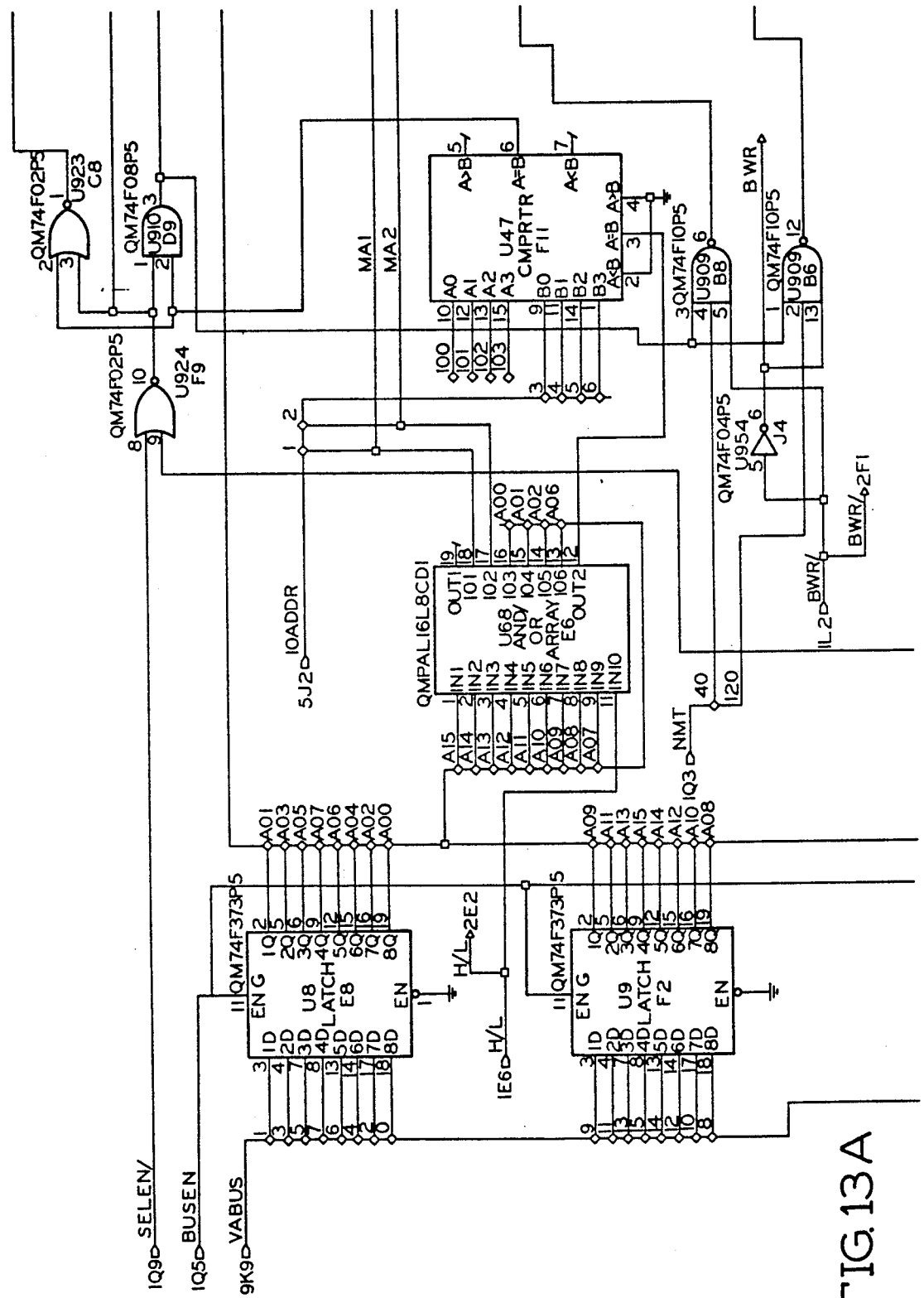
FIGS. 13A, B, C and D are schematics for the Image Memory Controller of the present invention showing the circuitry for the Memory and the Input/Output Address Decoder.
Figure 13B:
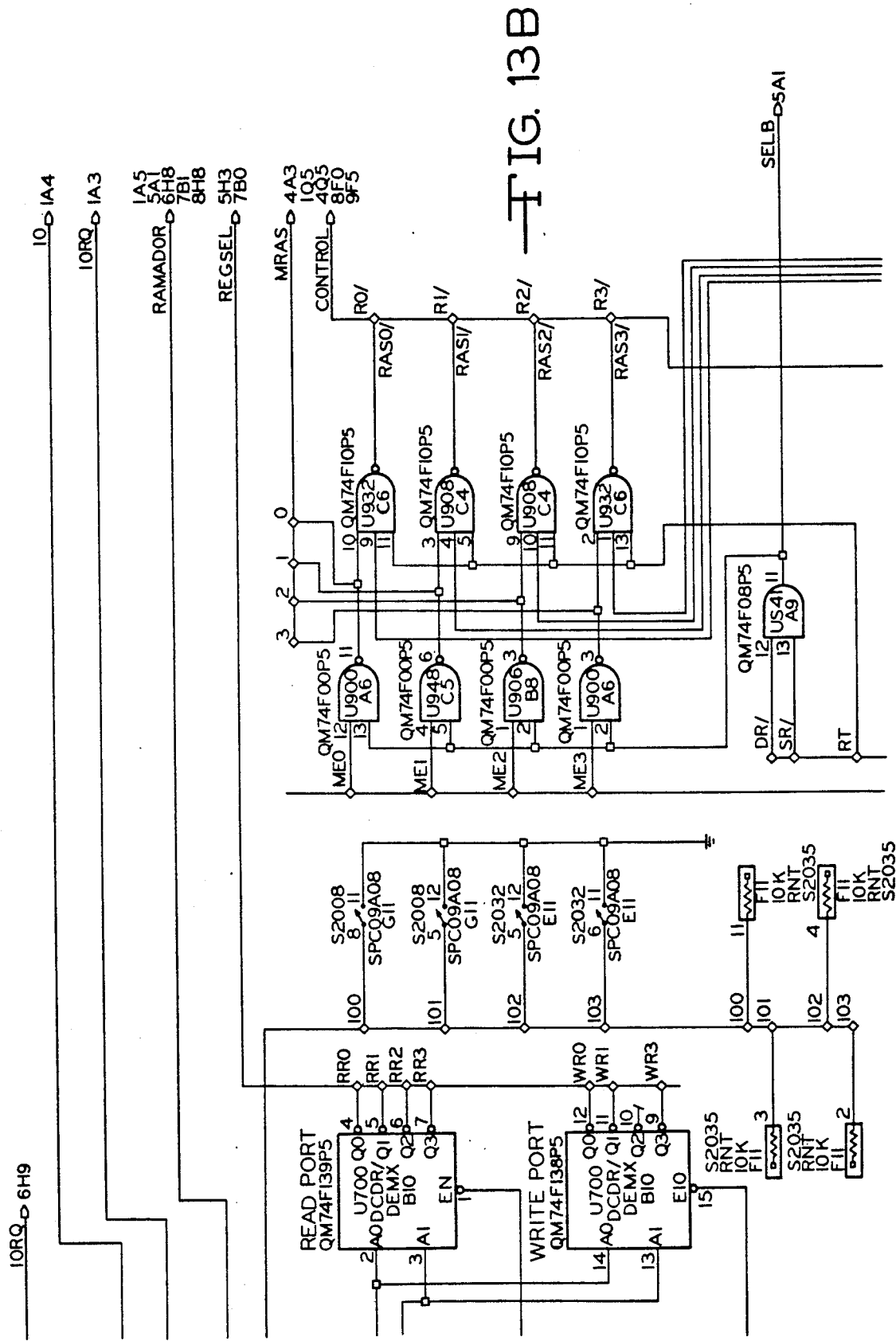
Figure 13C:
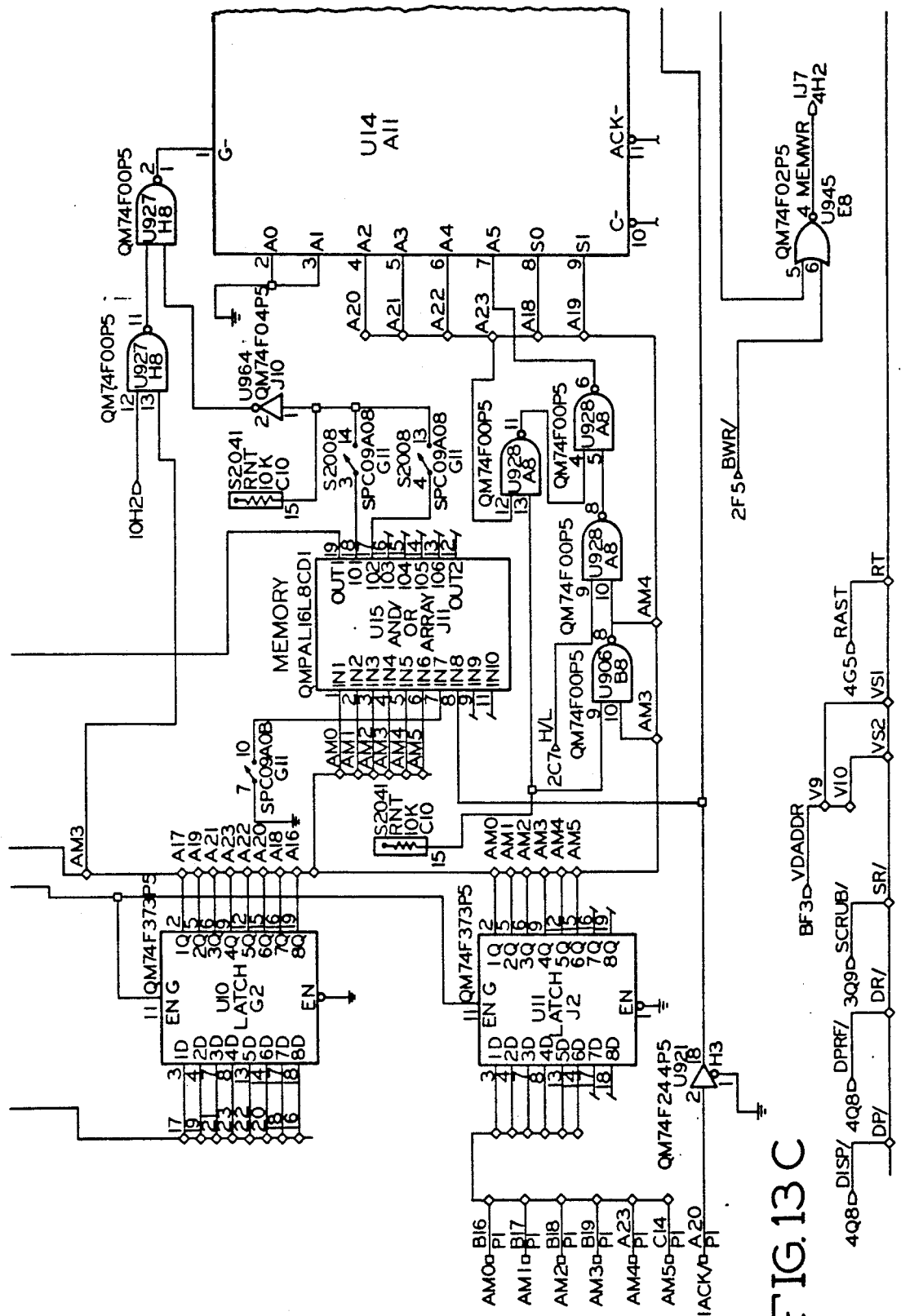
Figure 13D:
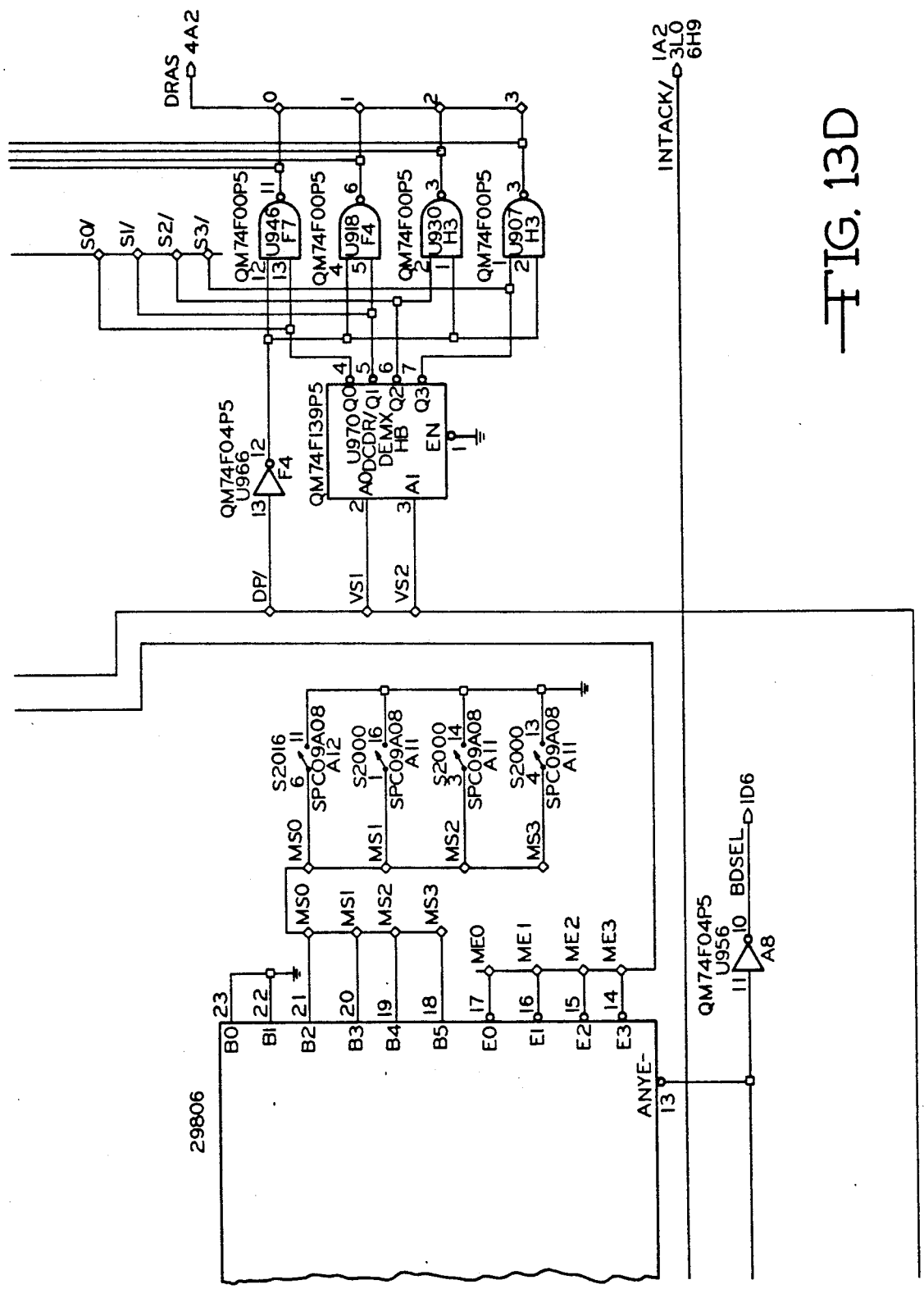
Figure 14A:
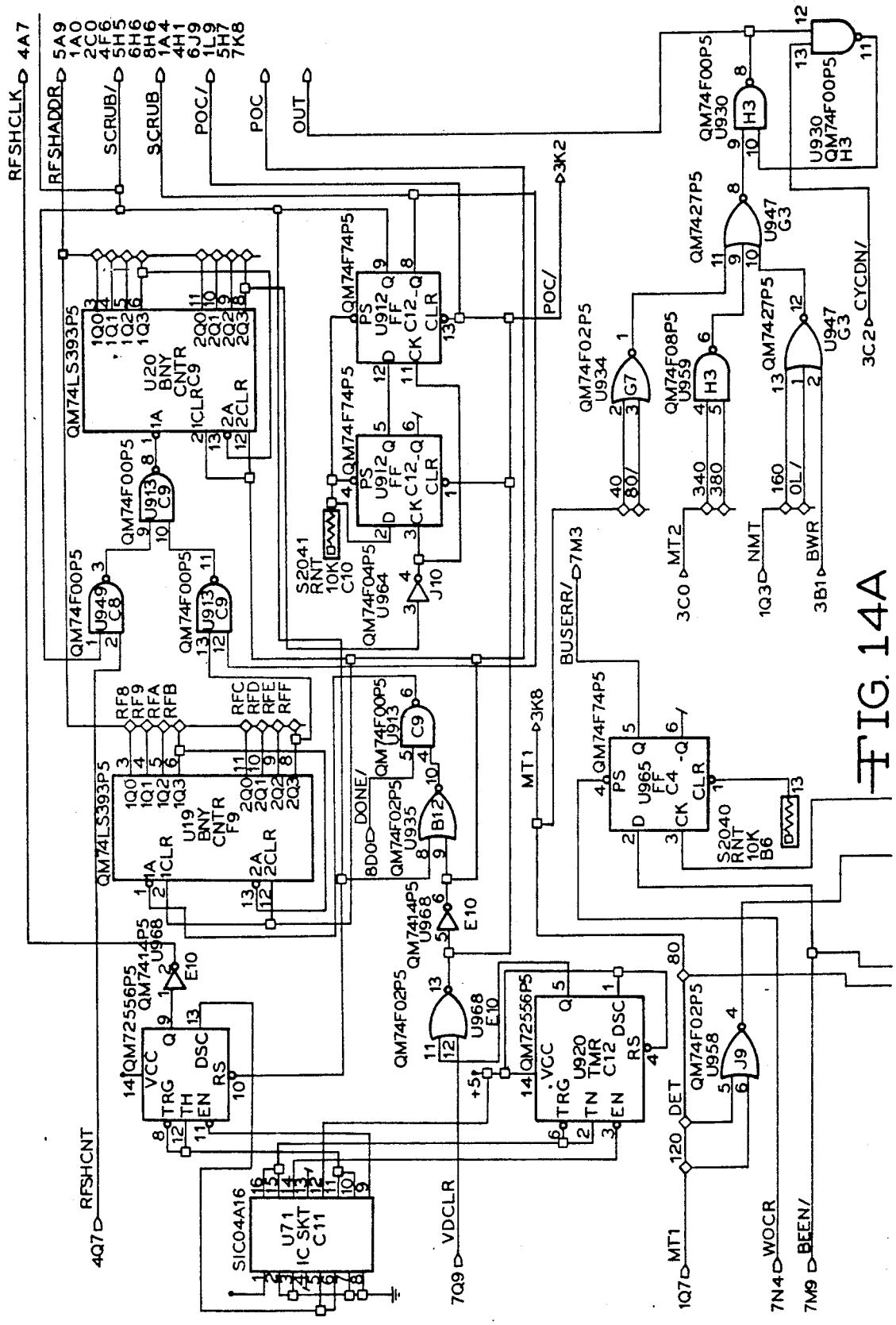
FIGS. 14A, B, C and D are schematics for the Image Memory Controller of the present invention showing the circuitry for the Memory Refresh Function and the Interrupt Request Function and Data Transfer Acknowledgement Generation.
Figure 14B:
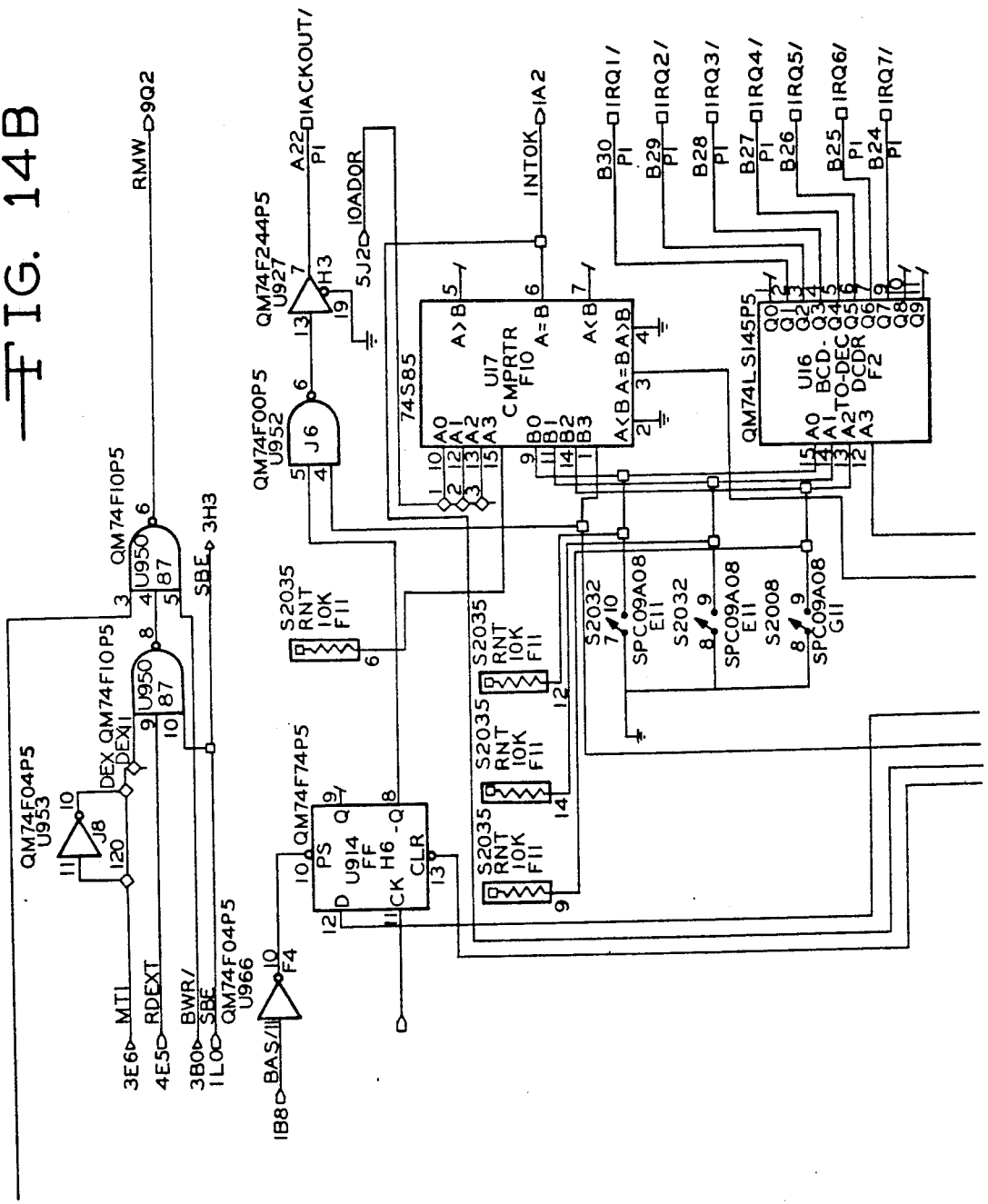
Figure 14C:
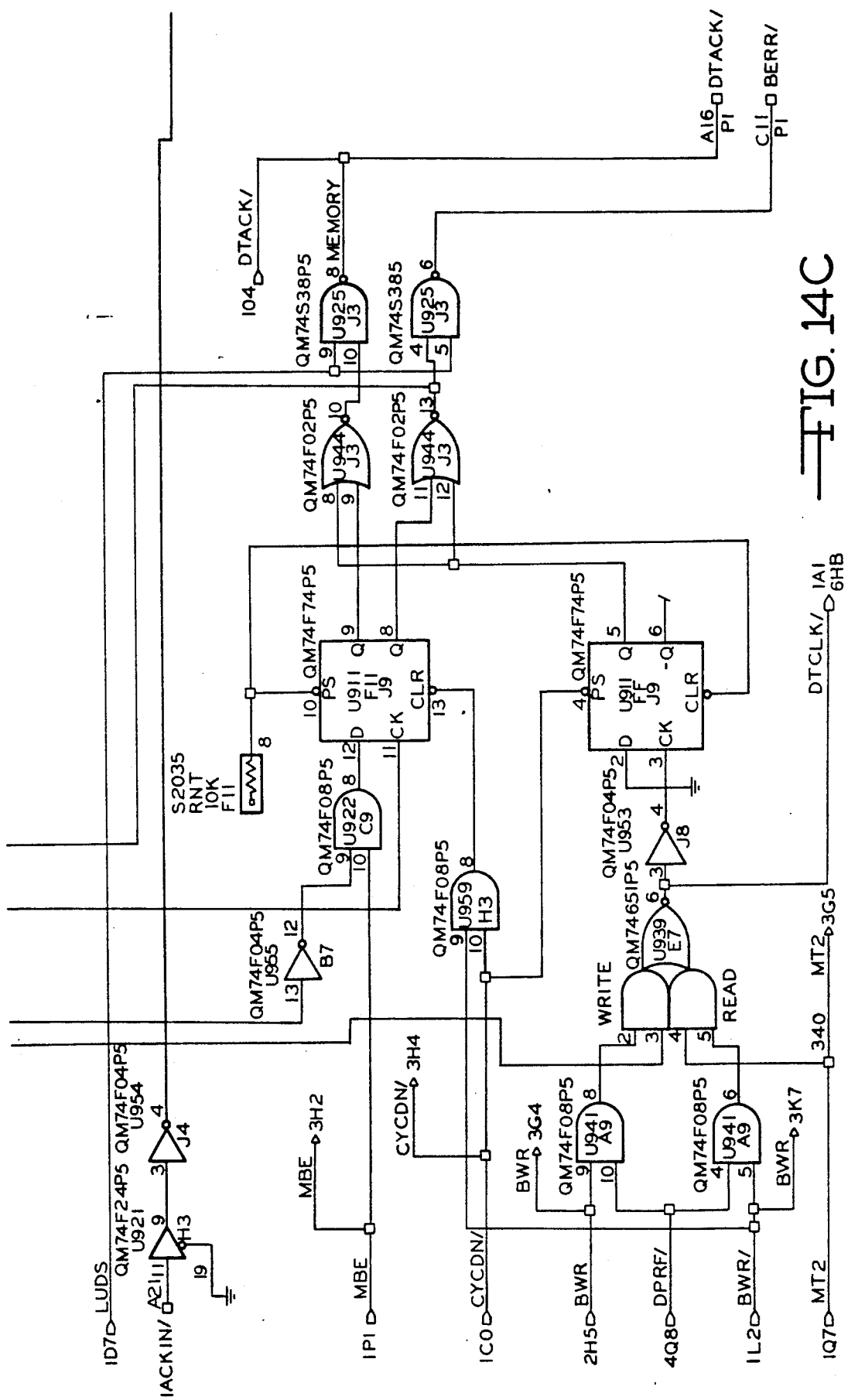
Figure 14D:
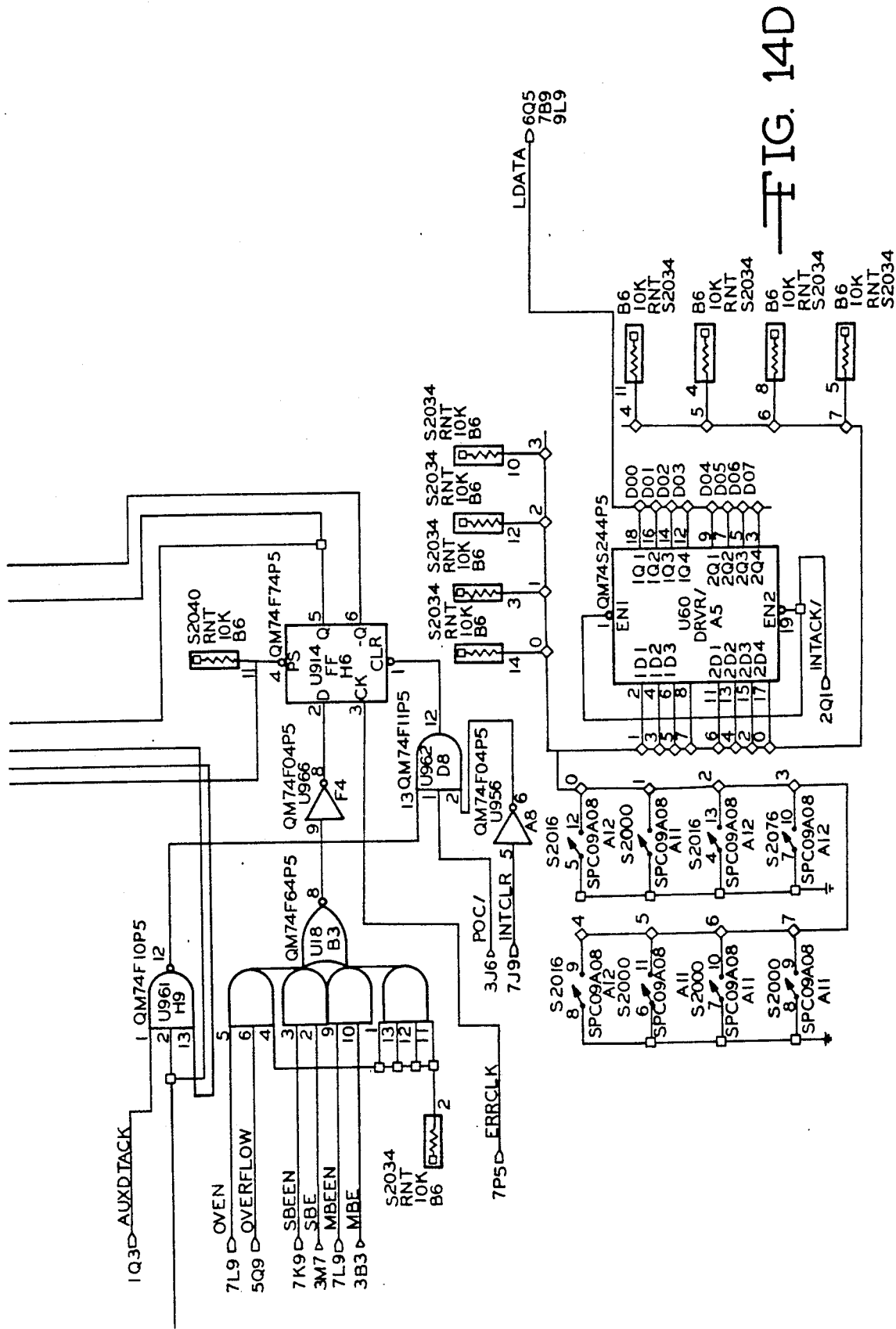
Figure 15A:
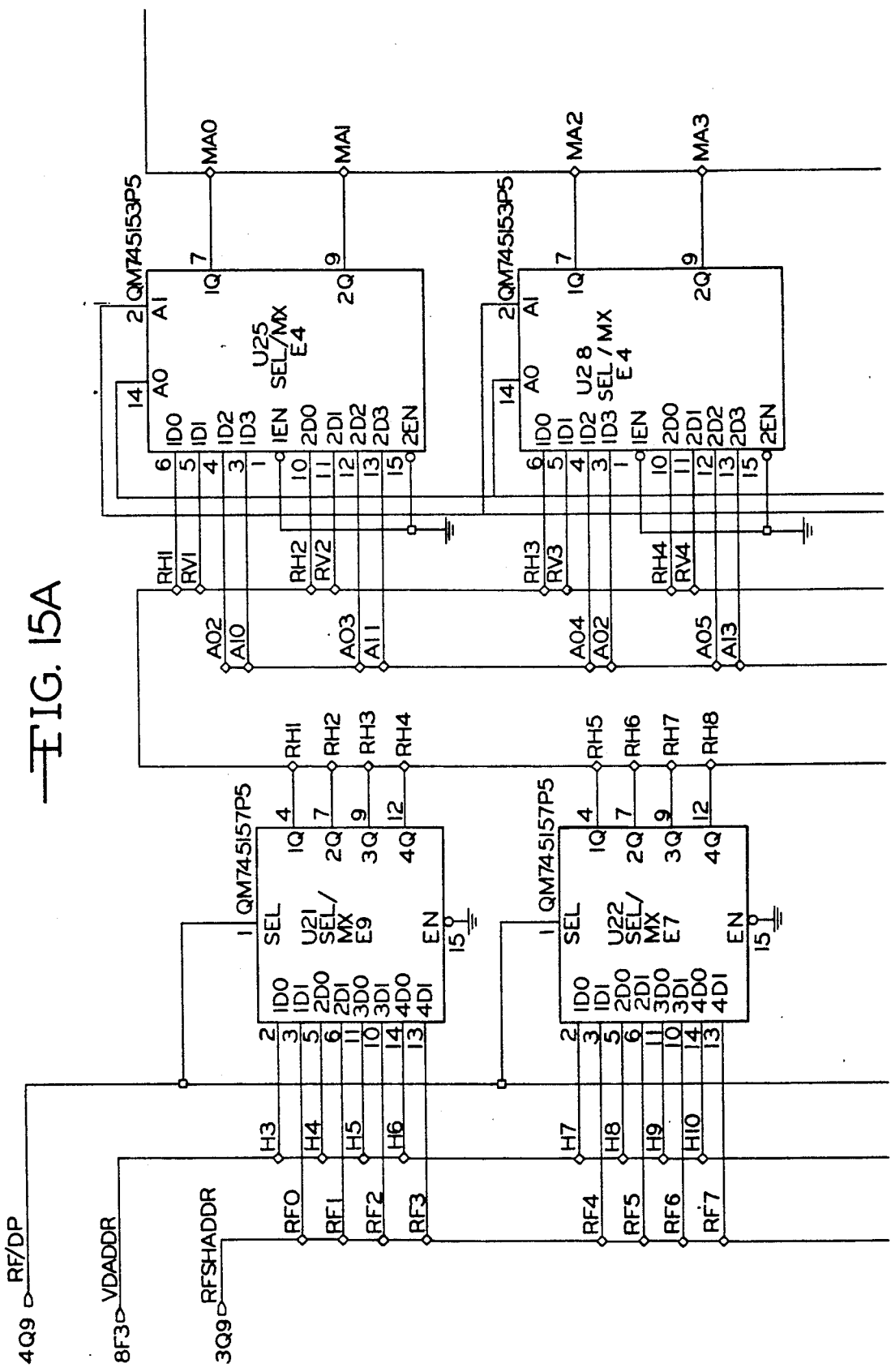
FIGS. 15A, B, C and D are schematics showing the Address Multiplexer circuitry for the Image Memory Controller of the present invention.
Figure 15C:
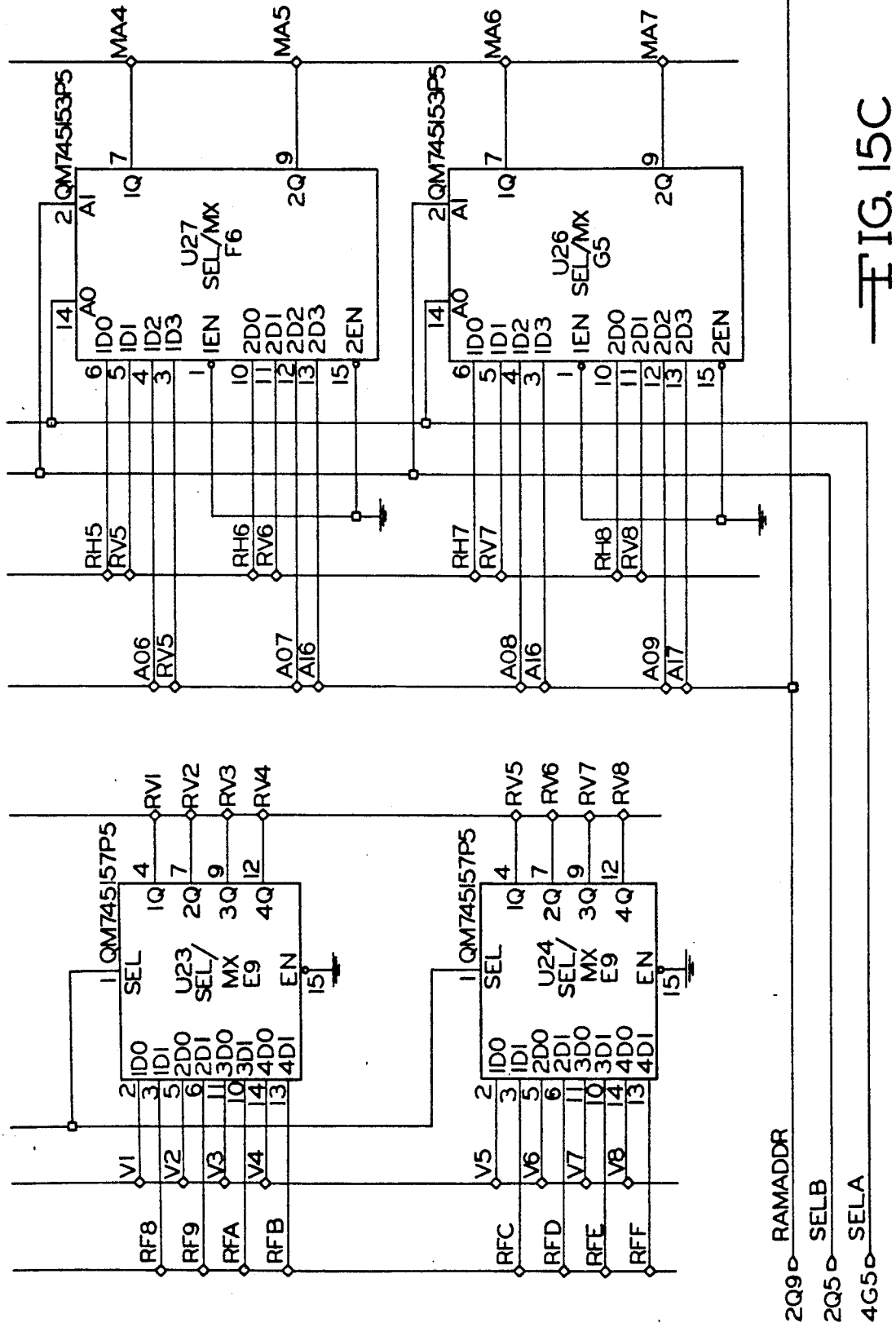
Figure 16A:
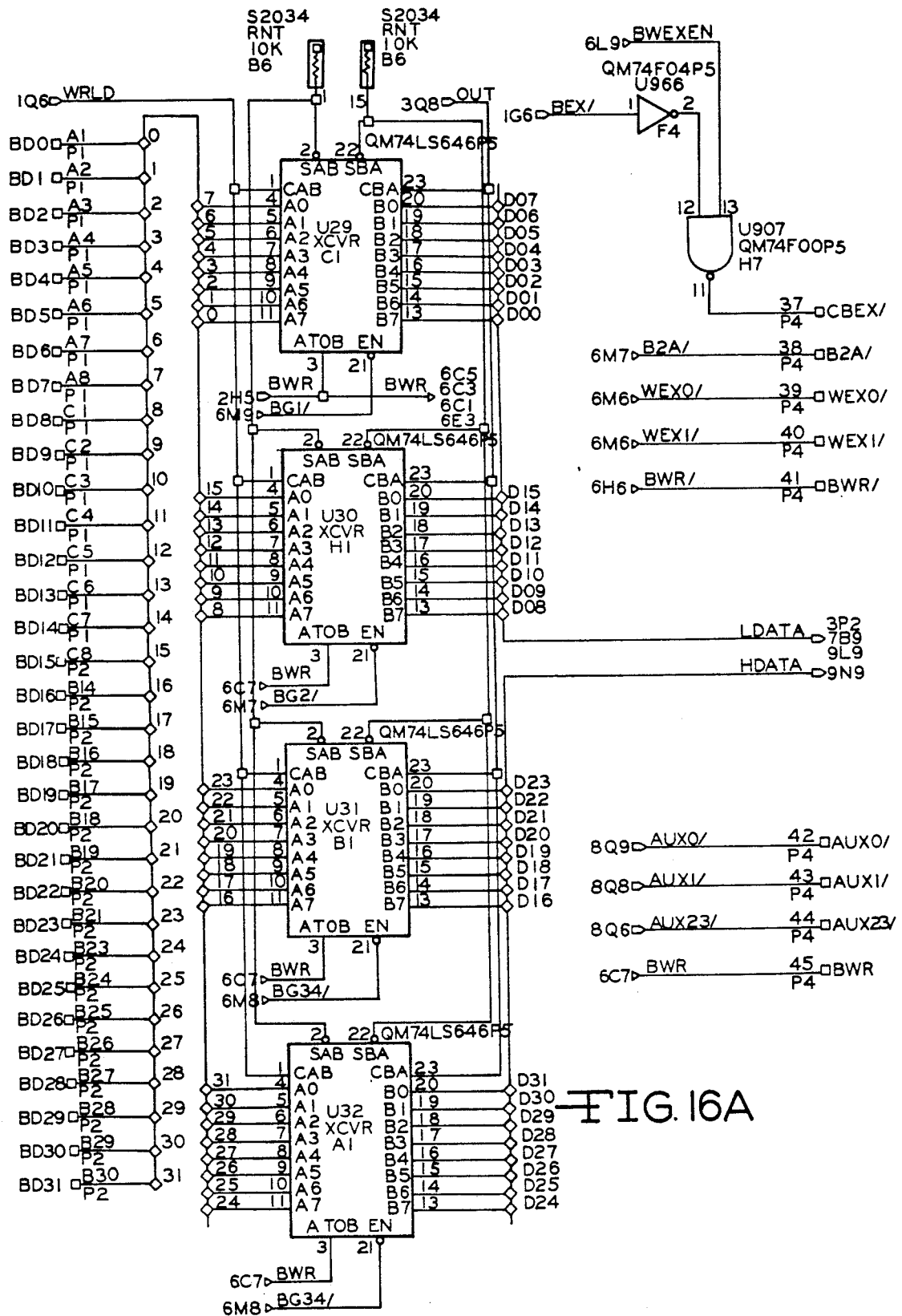
FIGS. 16A and B are schematics showing the Memory Buffers circuitry for the Image Memory Controller of the present invention.
Figure 16B:
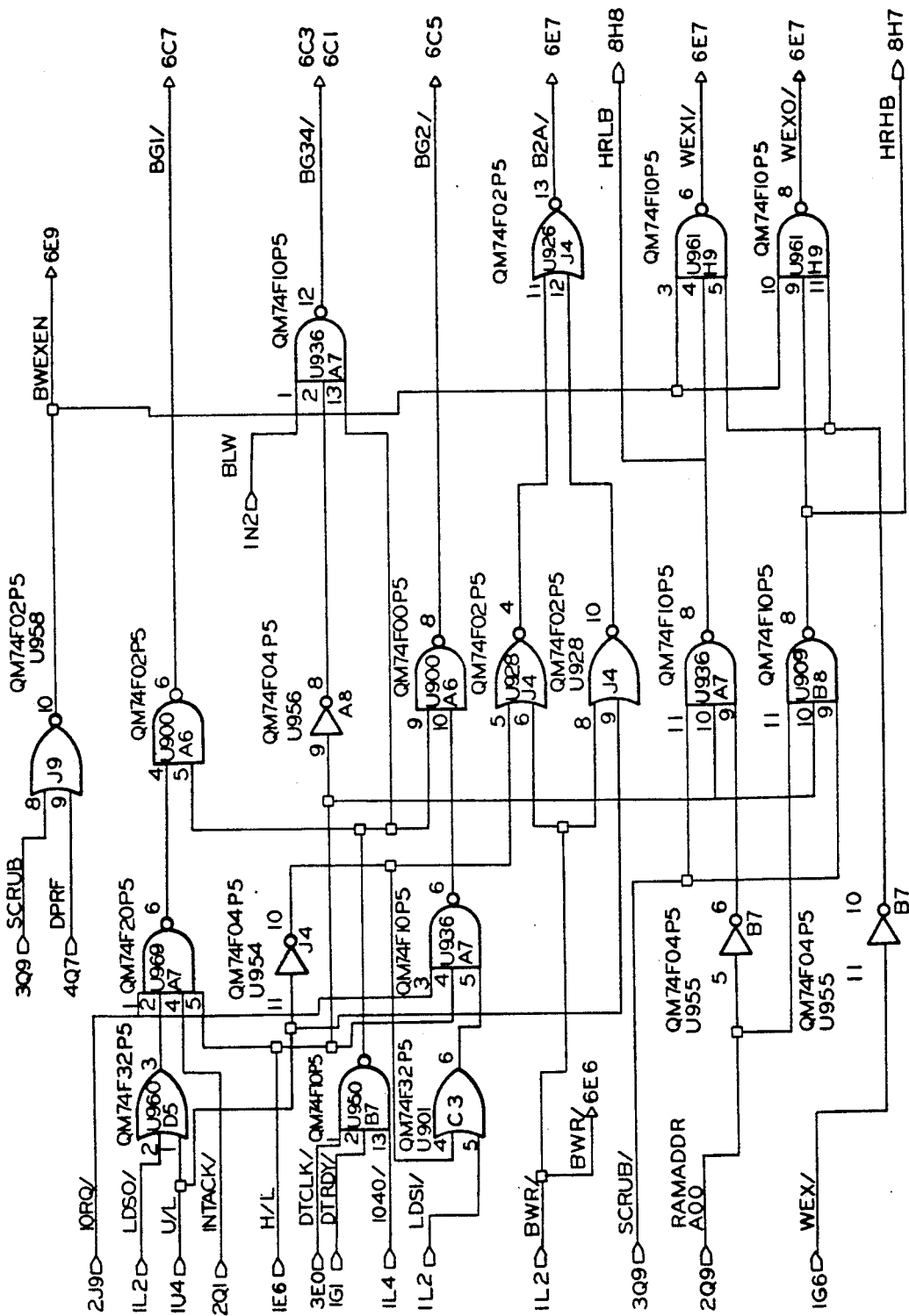
Figure 17A:
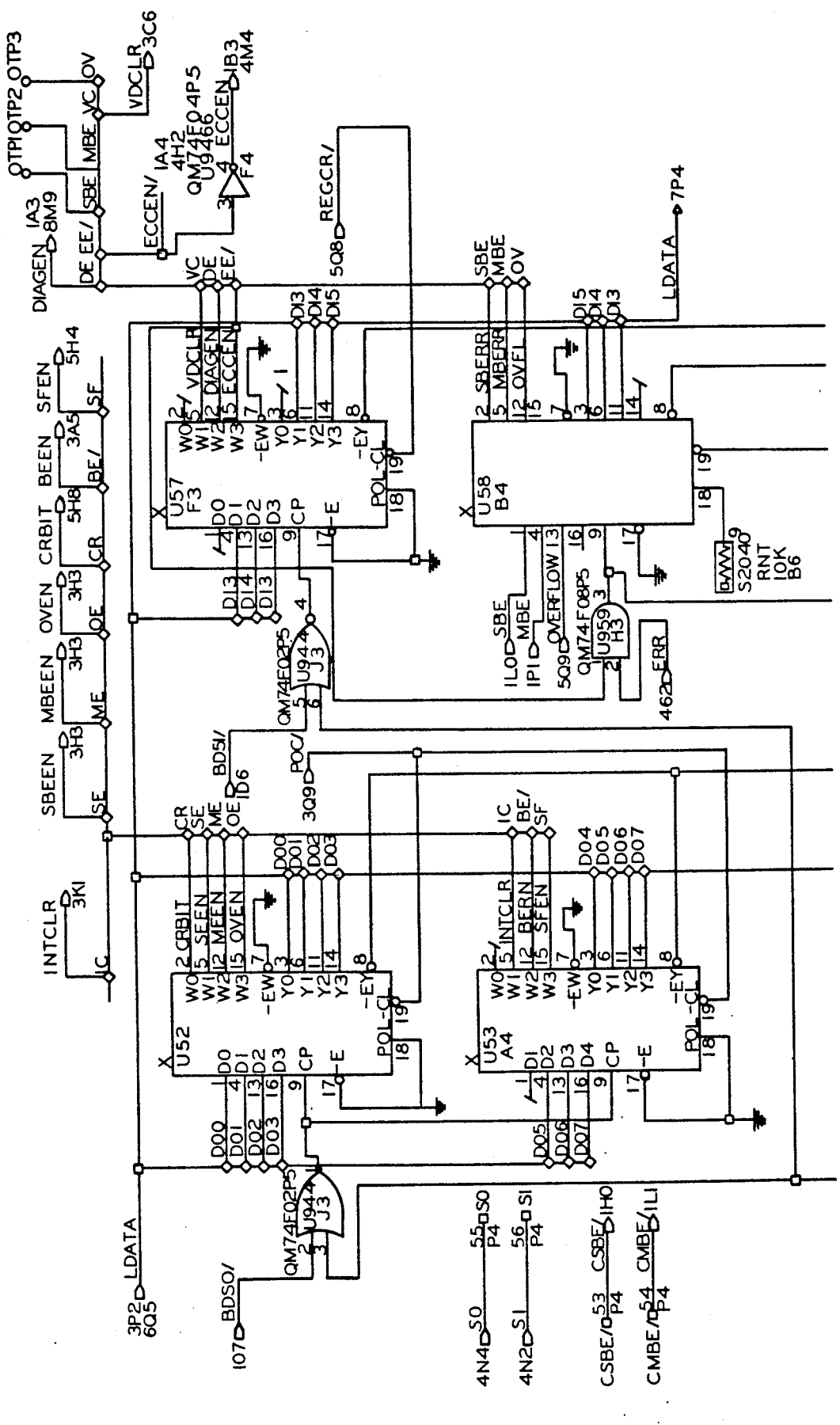
FIGS. 17A and B are schematics showing the Input/Output registers circuitry for the Image Memory Controller of the present invention.
Figure 17B:
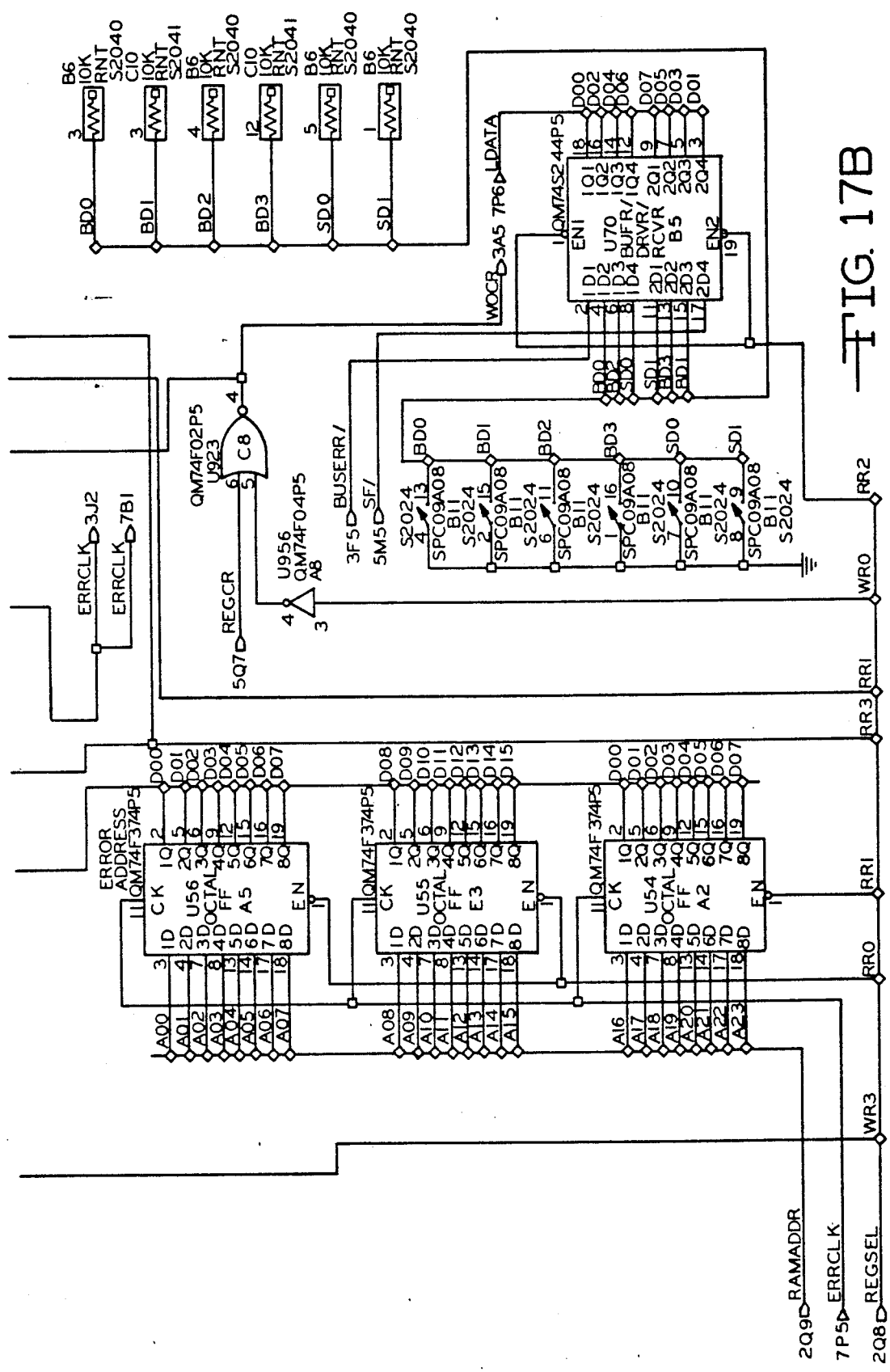
Figure 18A:
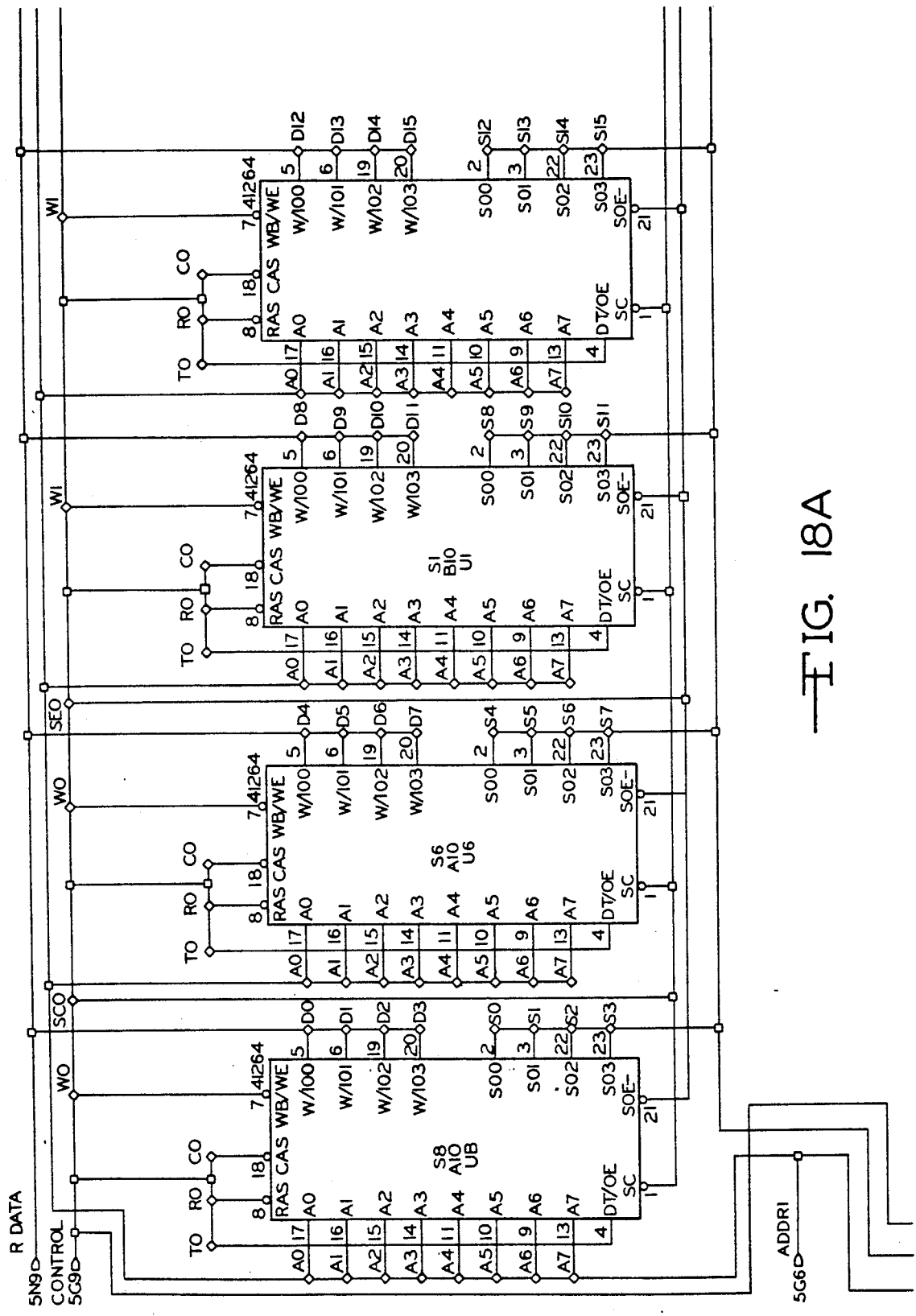
FIGS. 18A, B, C and D through 20A, B, C and D are schematics showing the Memory Chip Array circuitry for the Image Memory Array of the present invention.
Figure 18B:
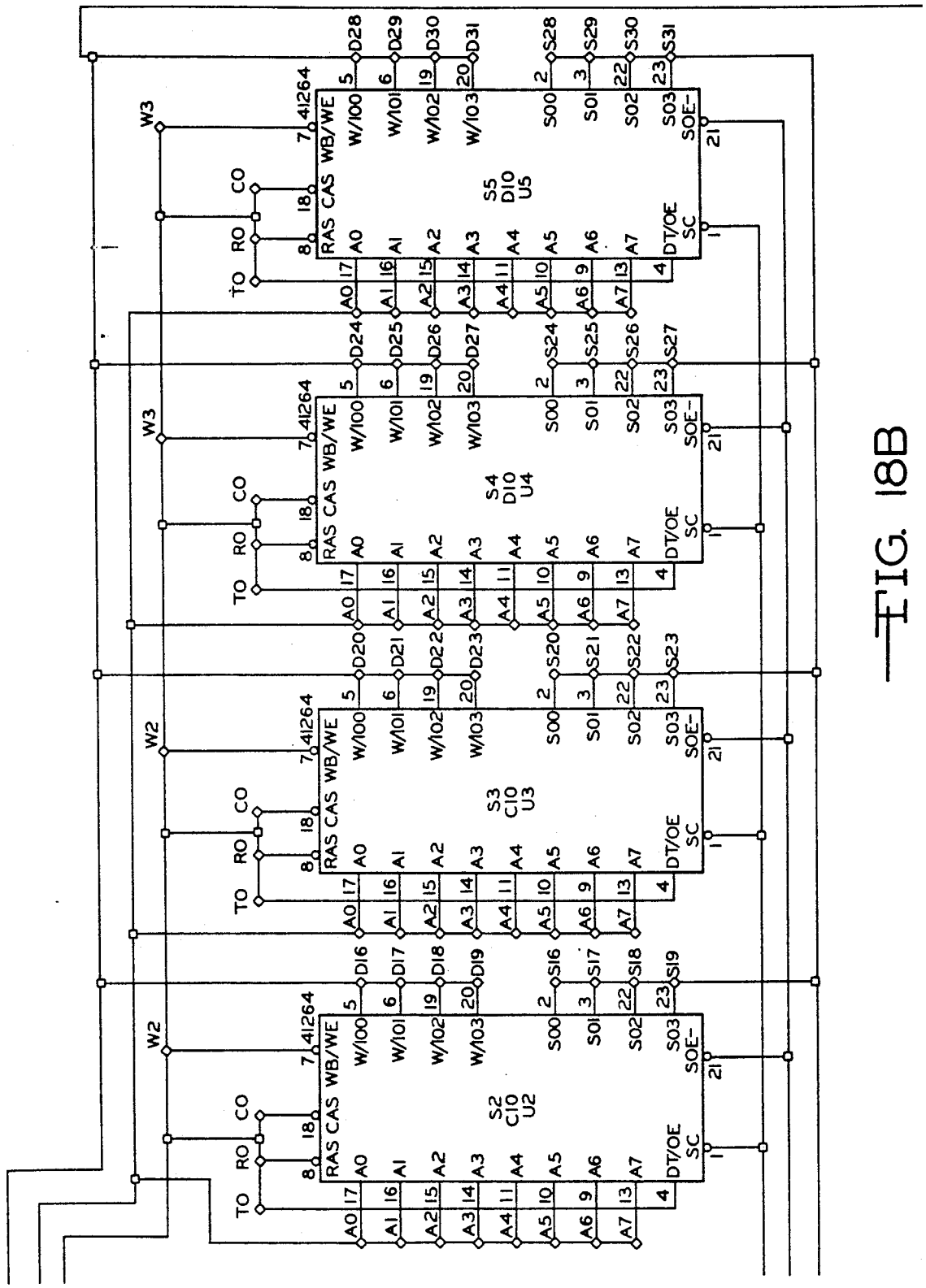
Figure 18C:
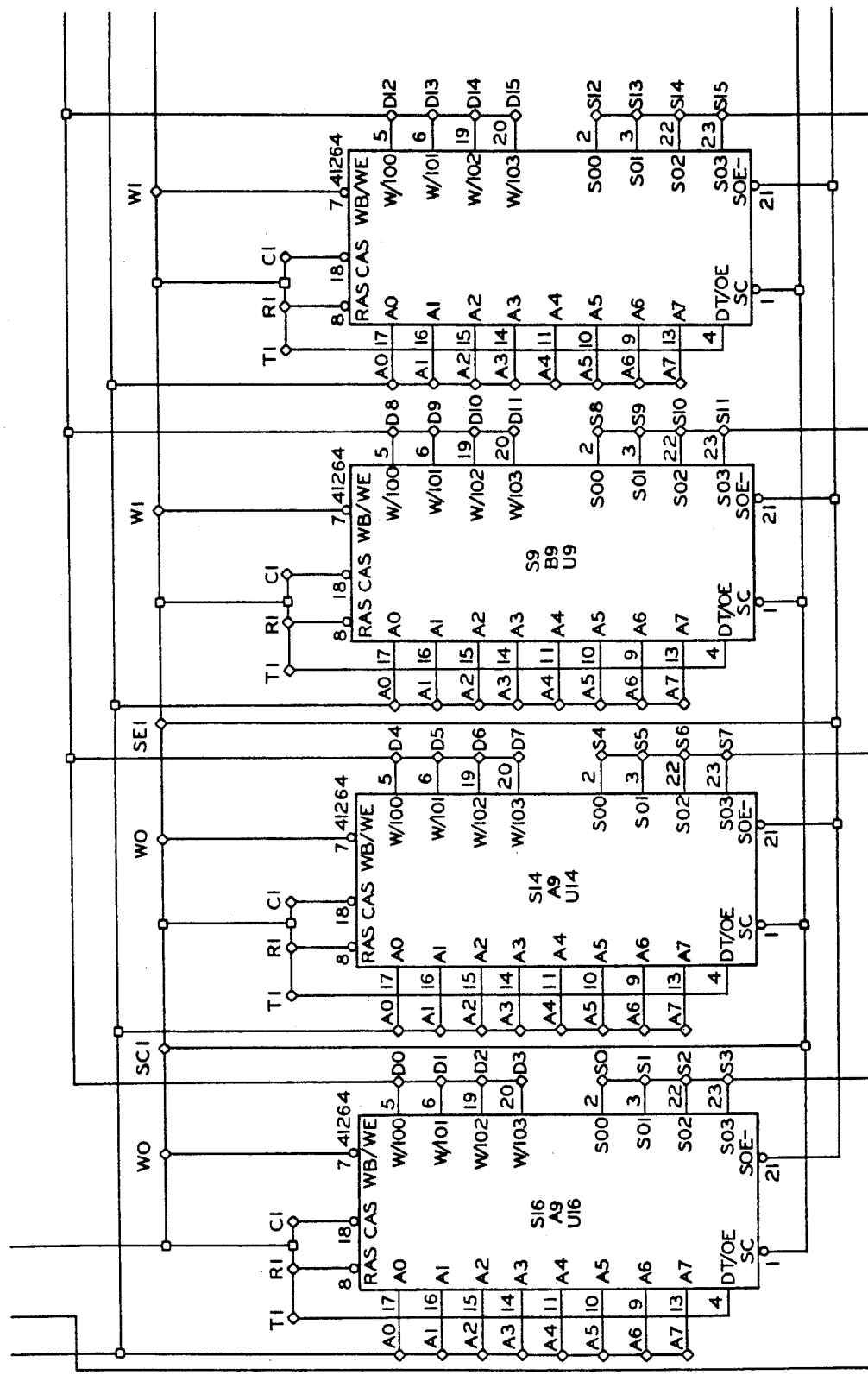
Figure 18D:
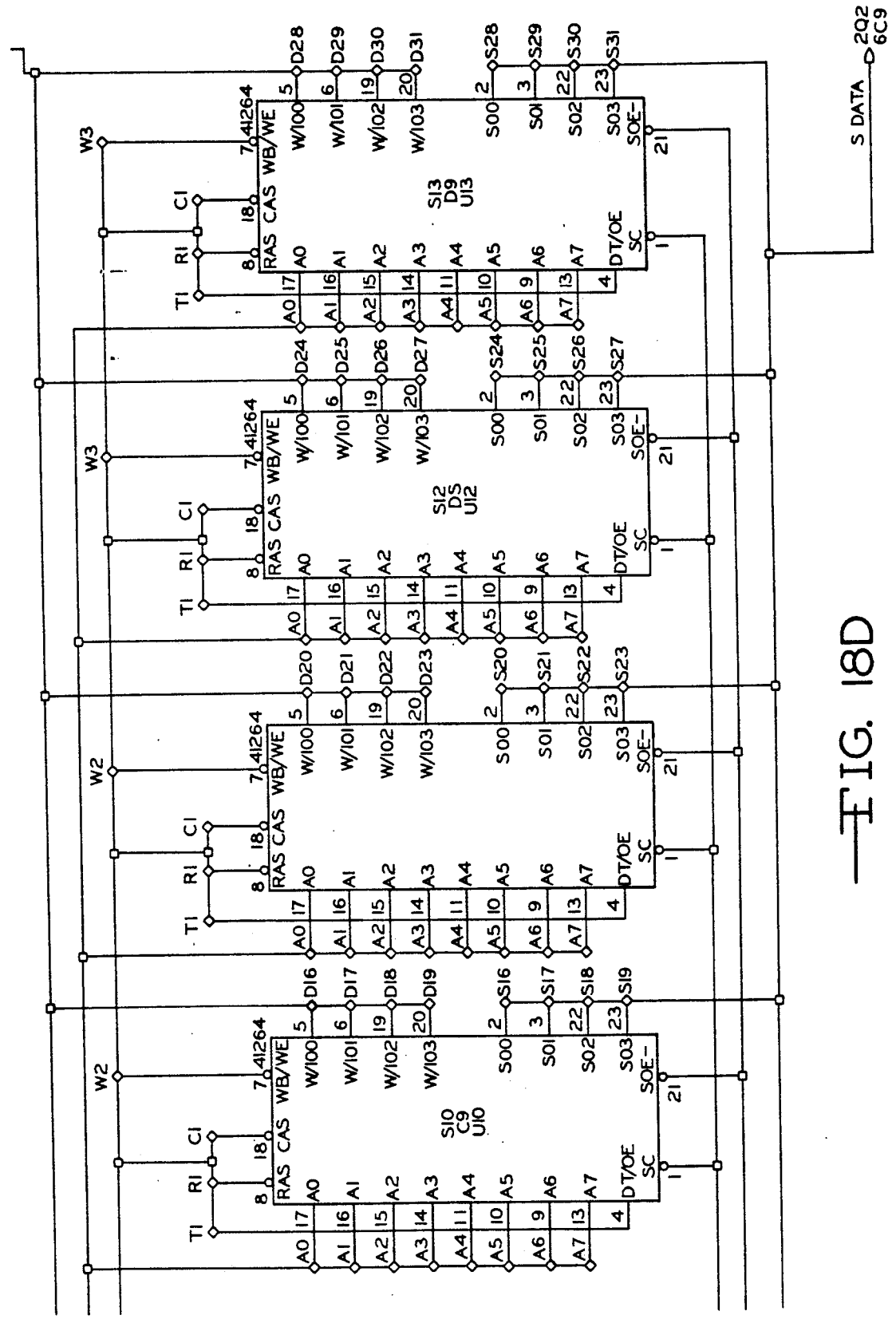
Figure 19A:
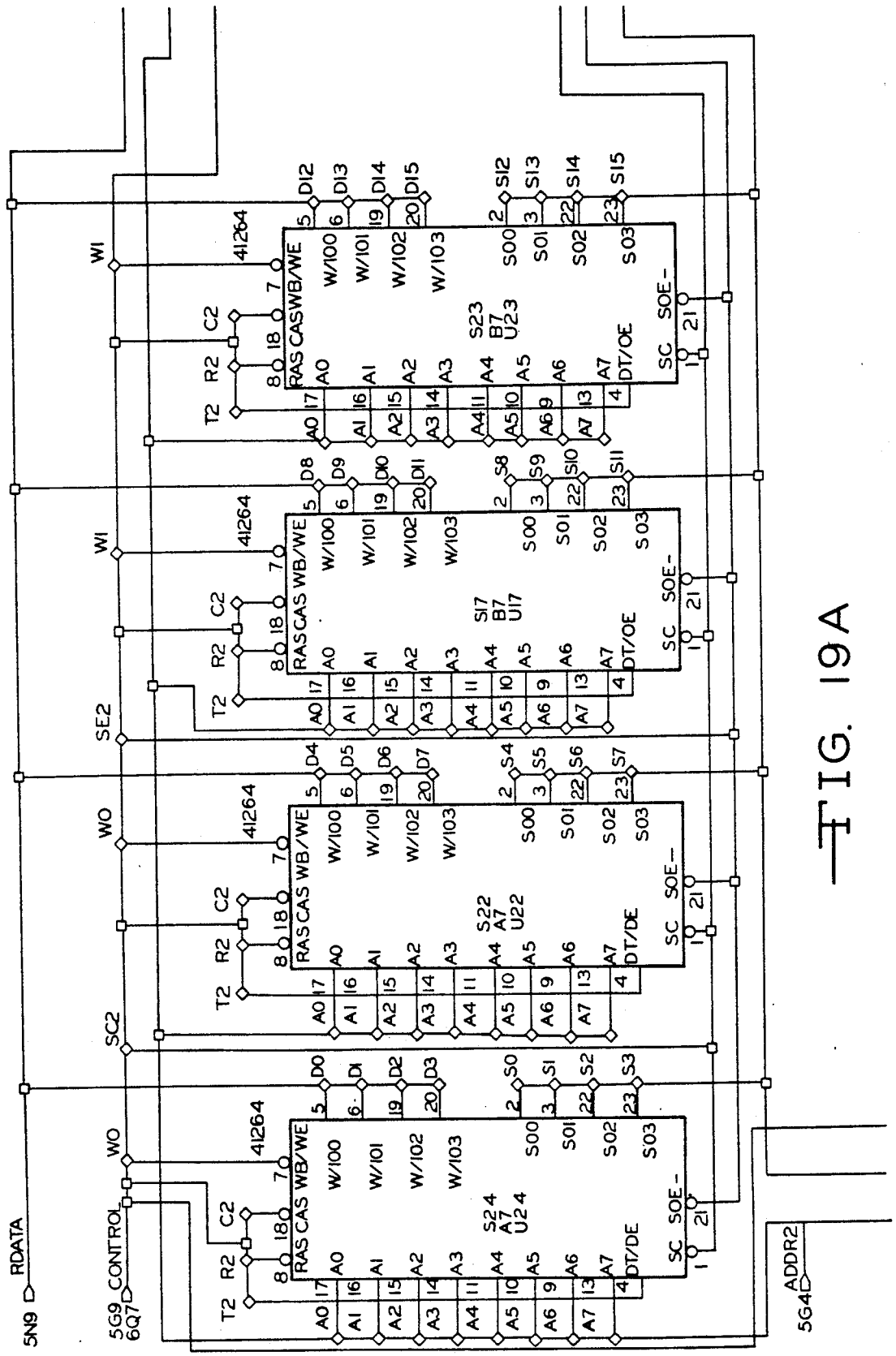
Figure 19B:
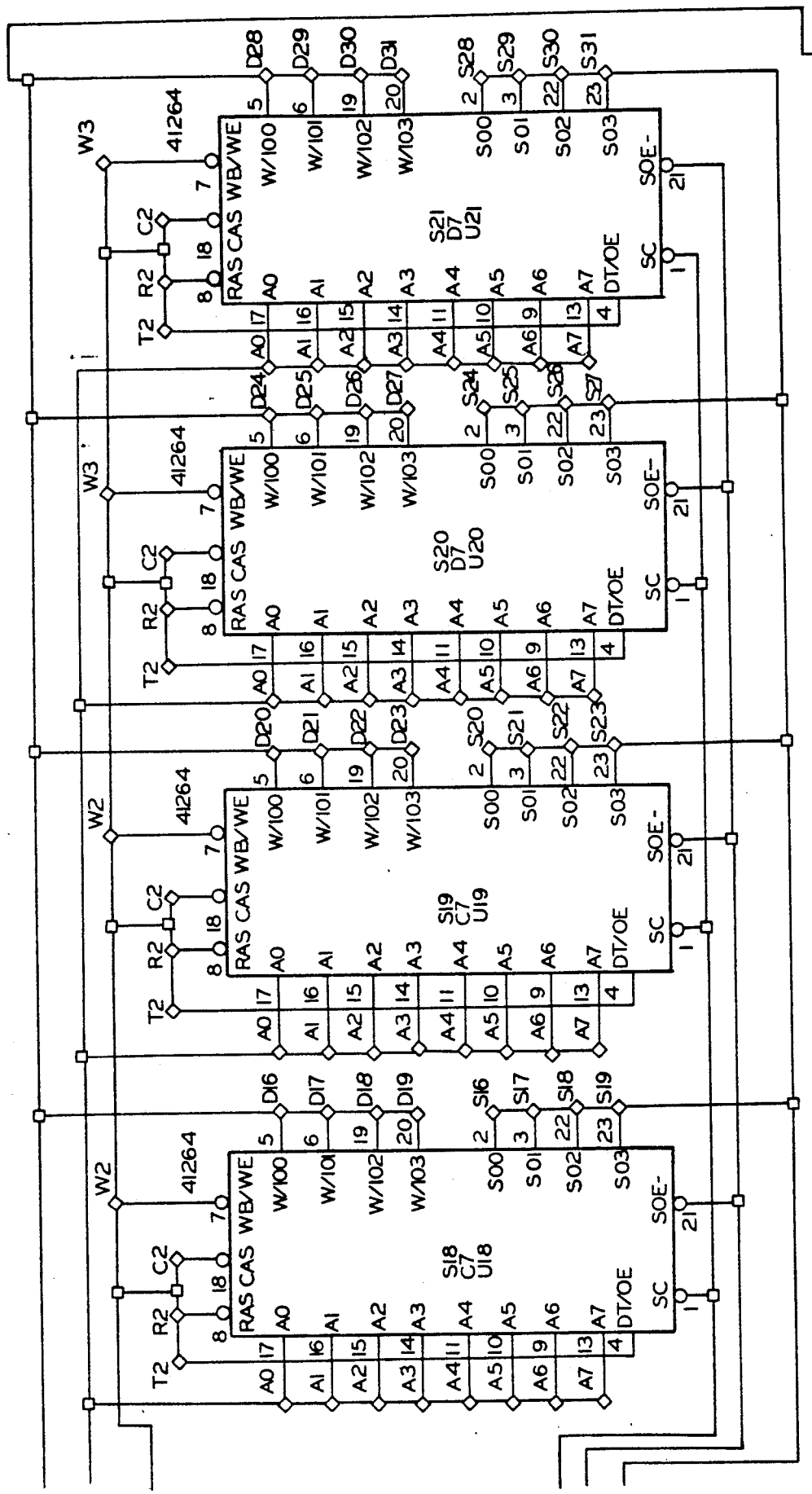
Figure 19C:
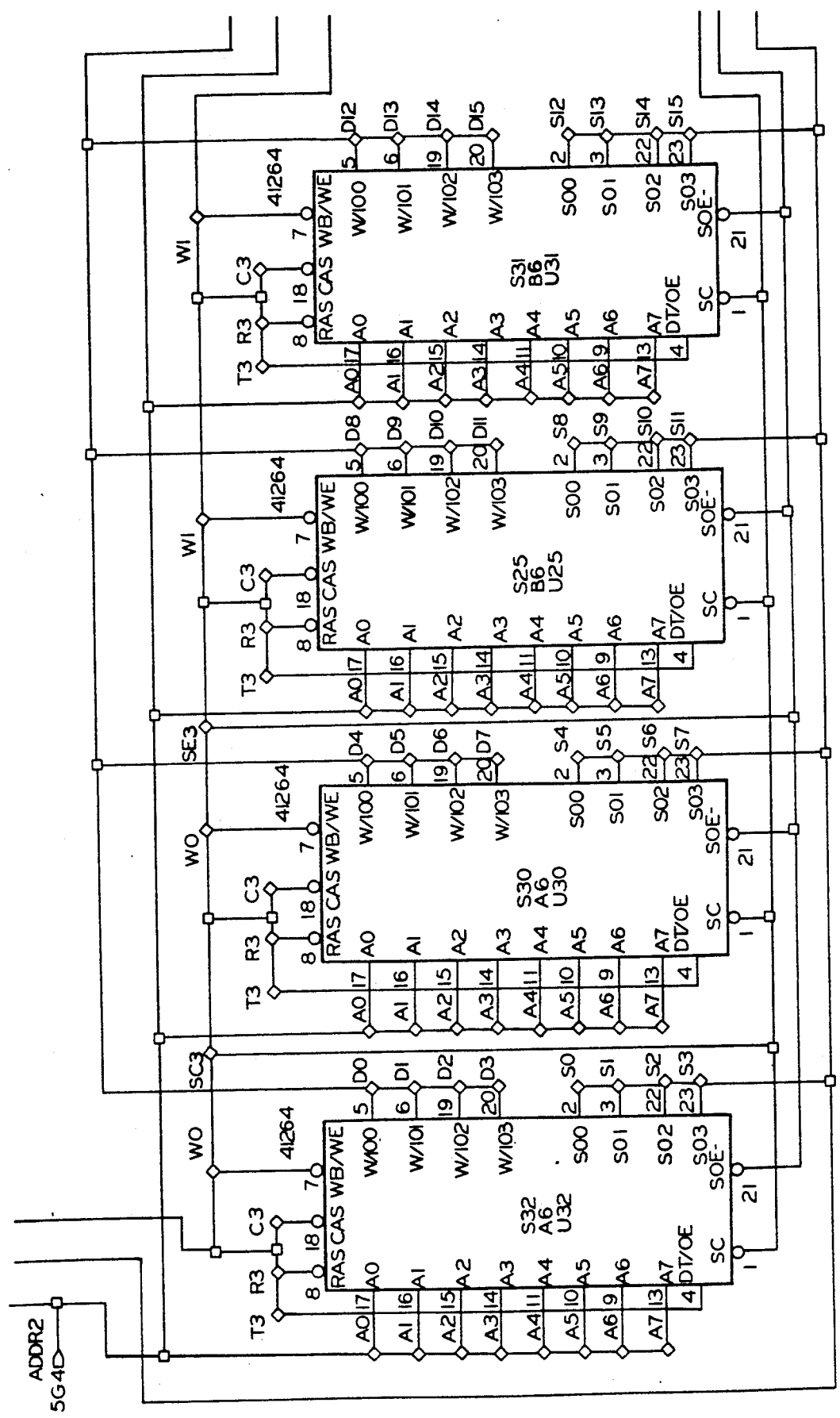
Figure 19D:
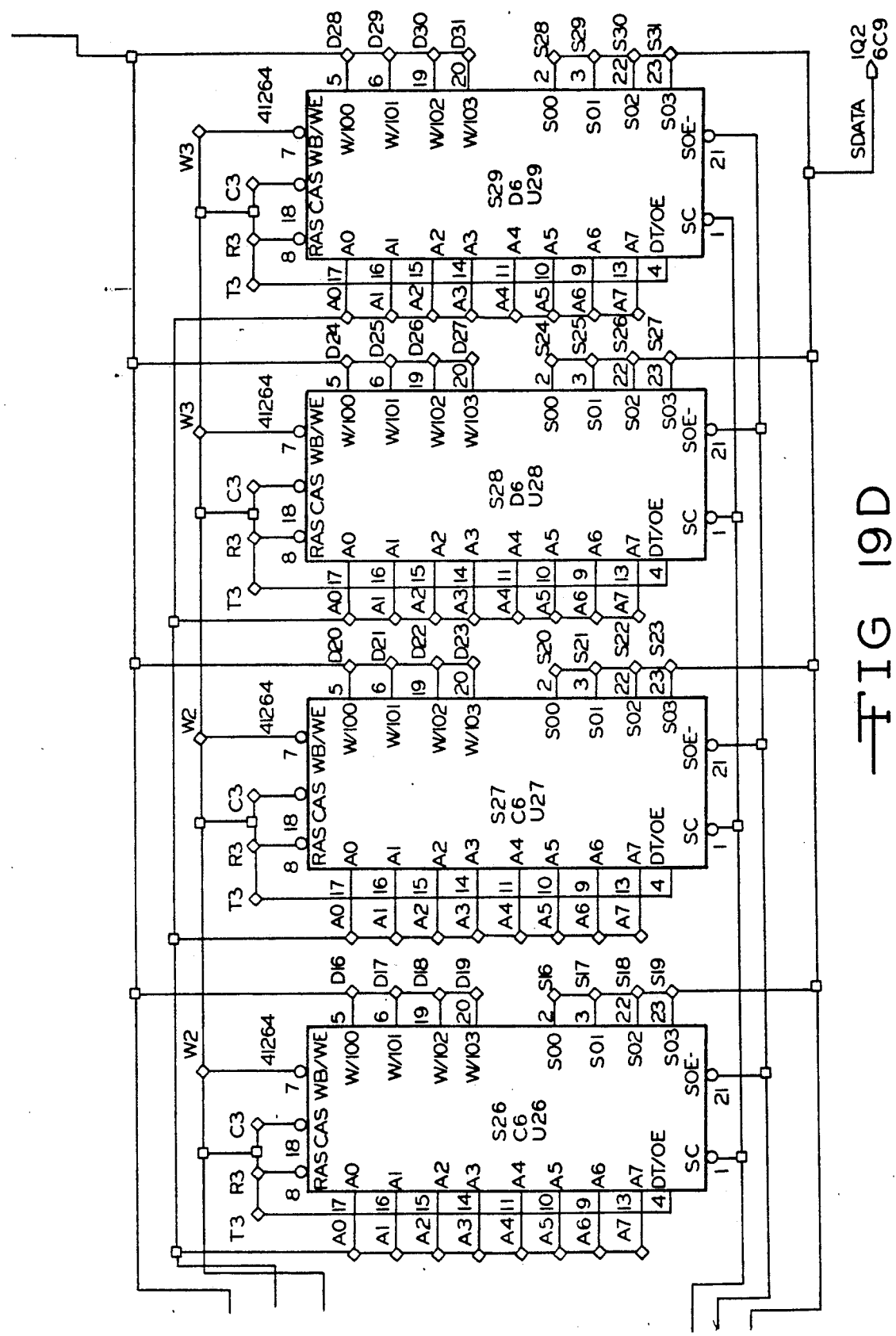
Figure 20A:
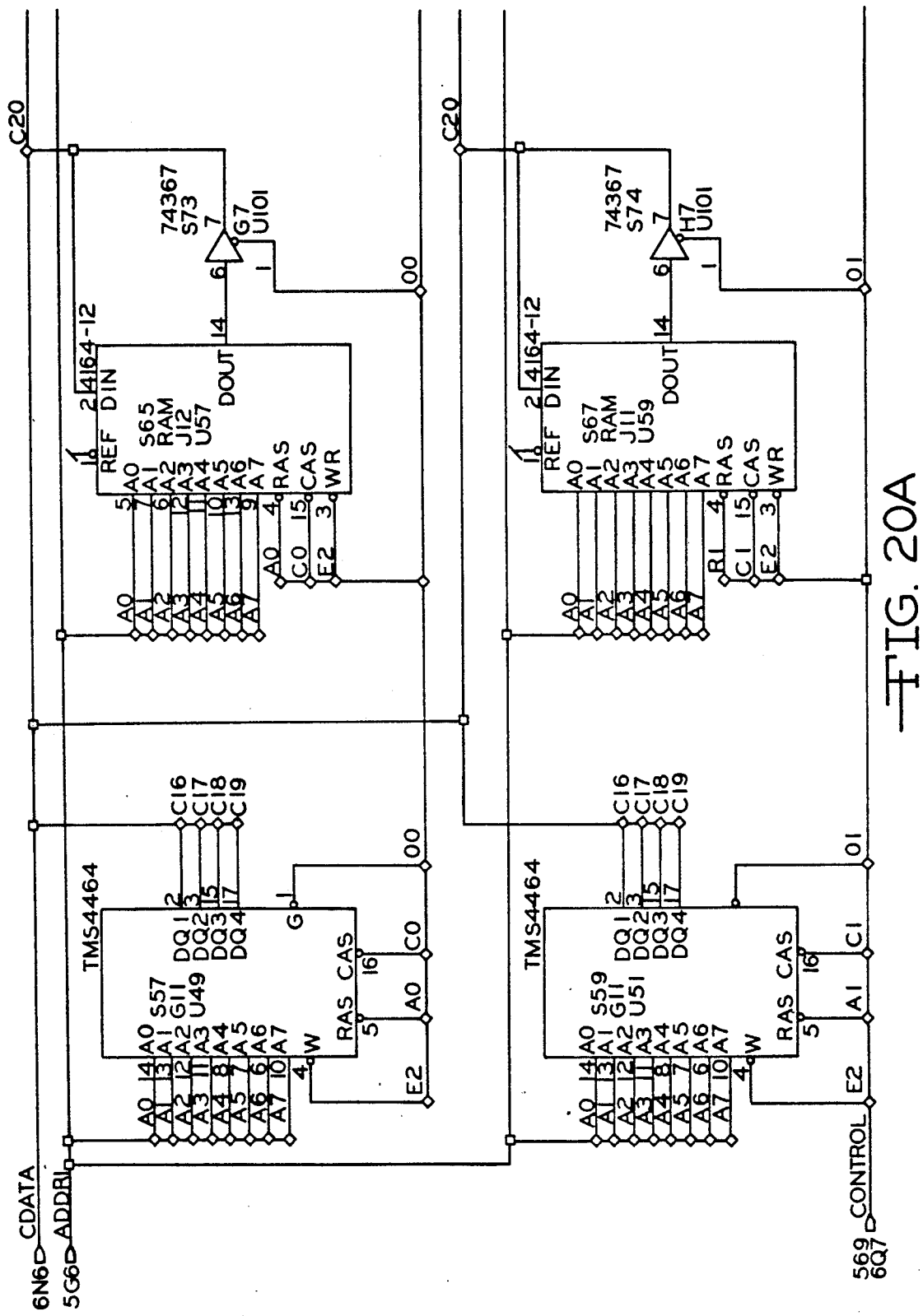
Figure 20C:
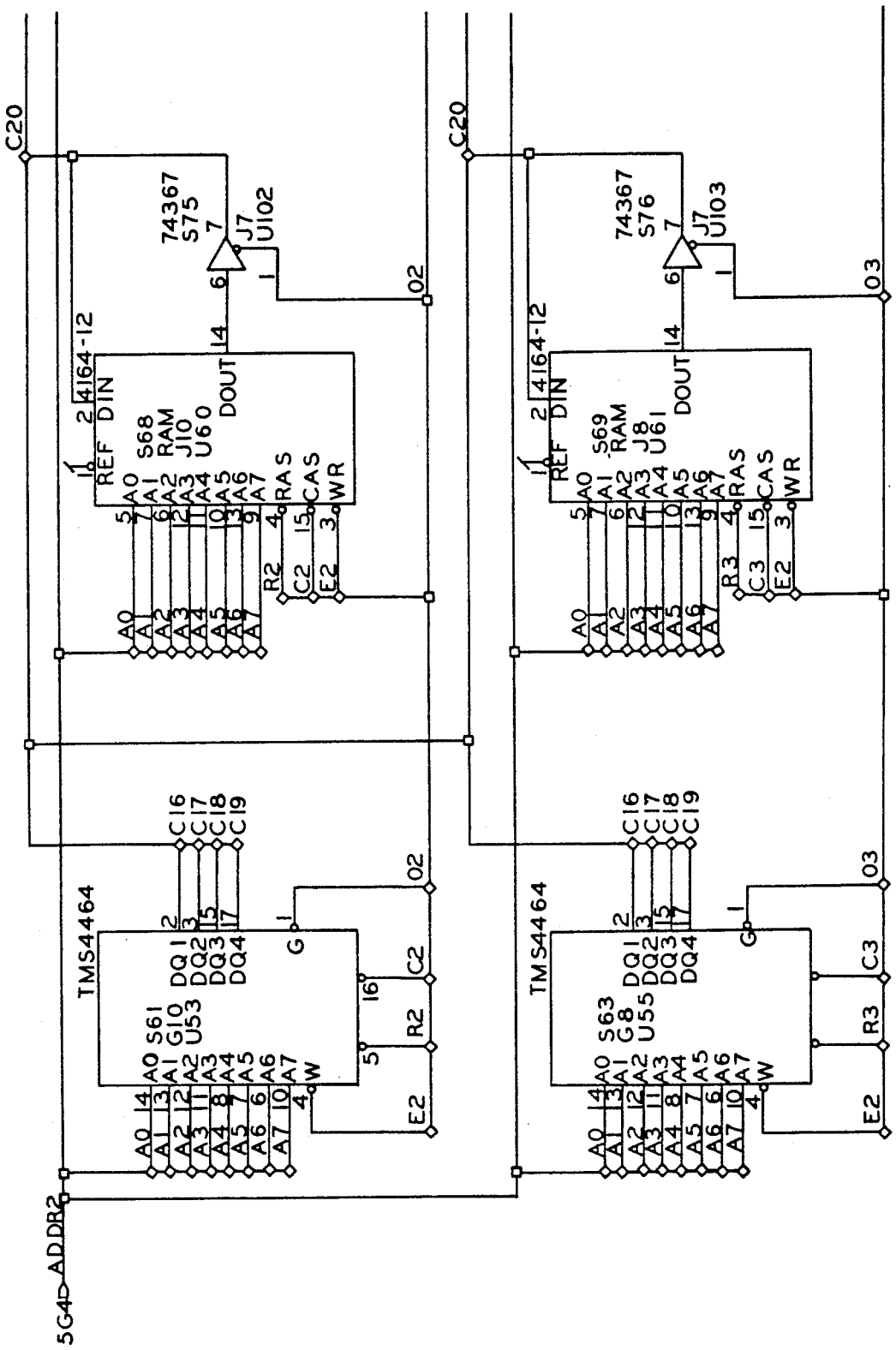
Figure 20D:
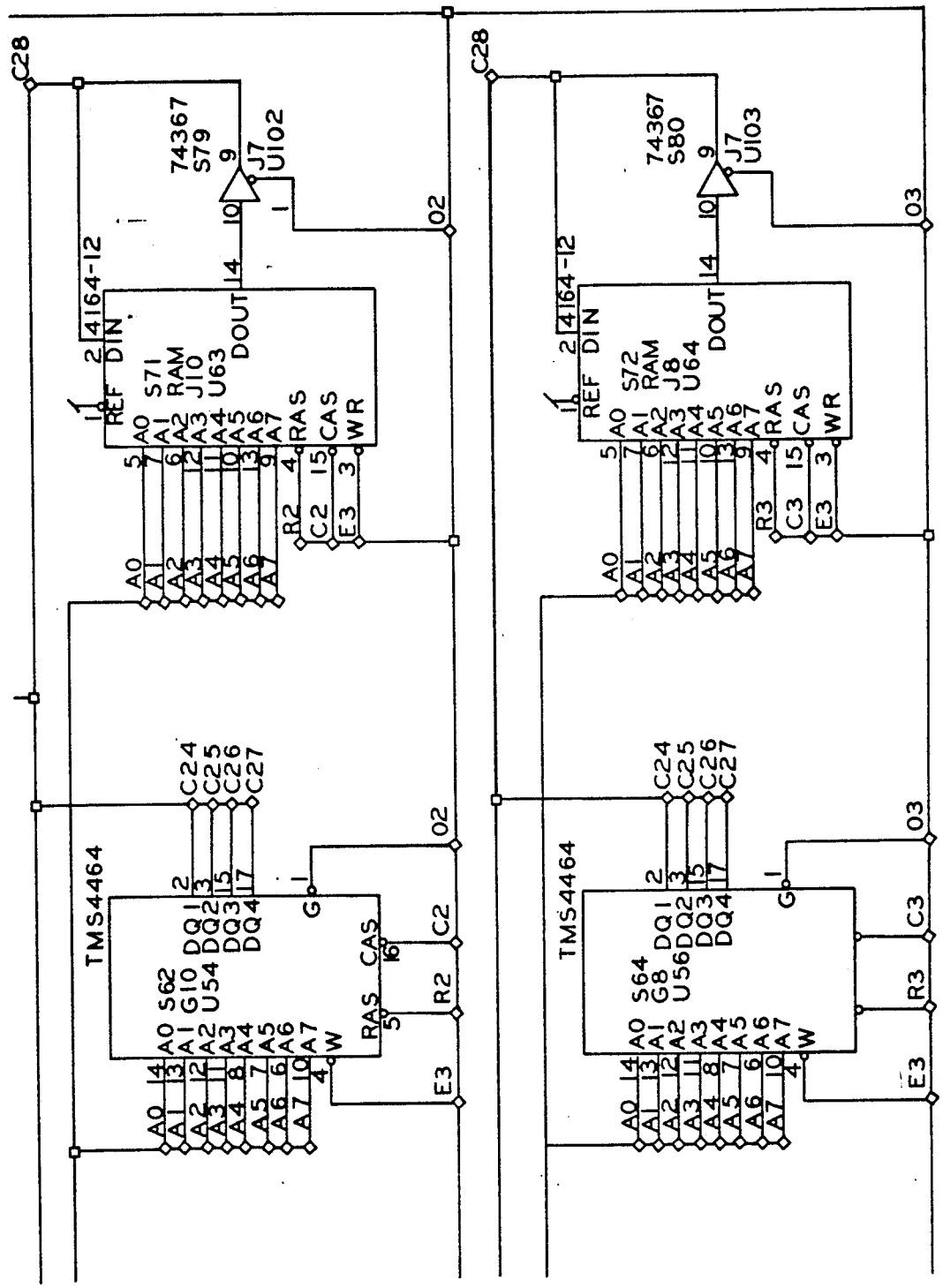
Figure 21B:
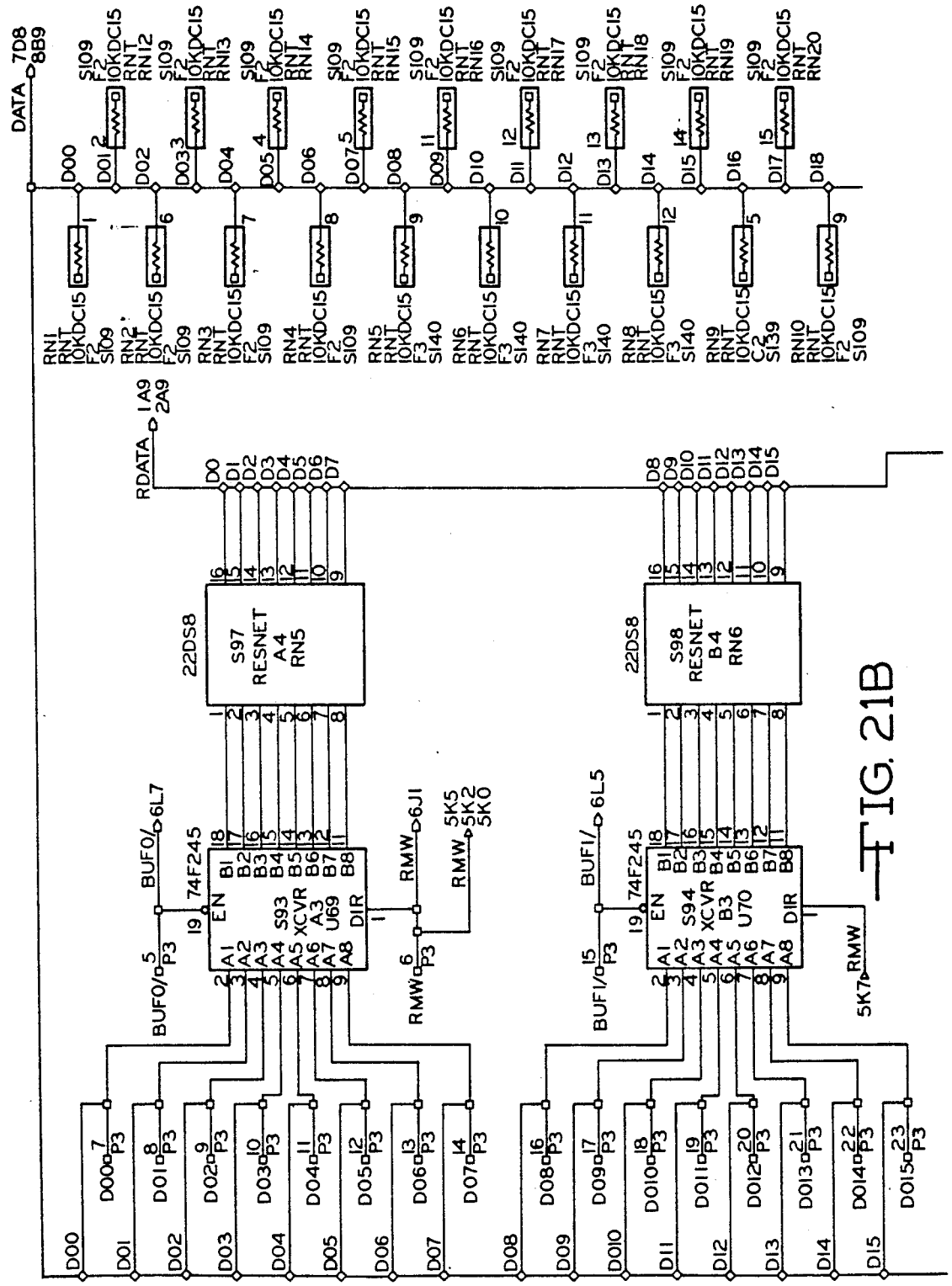
FIGS. 21A, B, C and D are schematics showing the Memory Arrays, Address liners, and Control Bus circuitry for the Image Memory Array of the present invention.
Figure 21C:
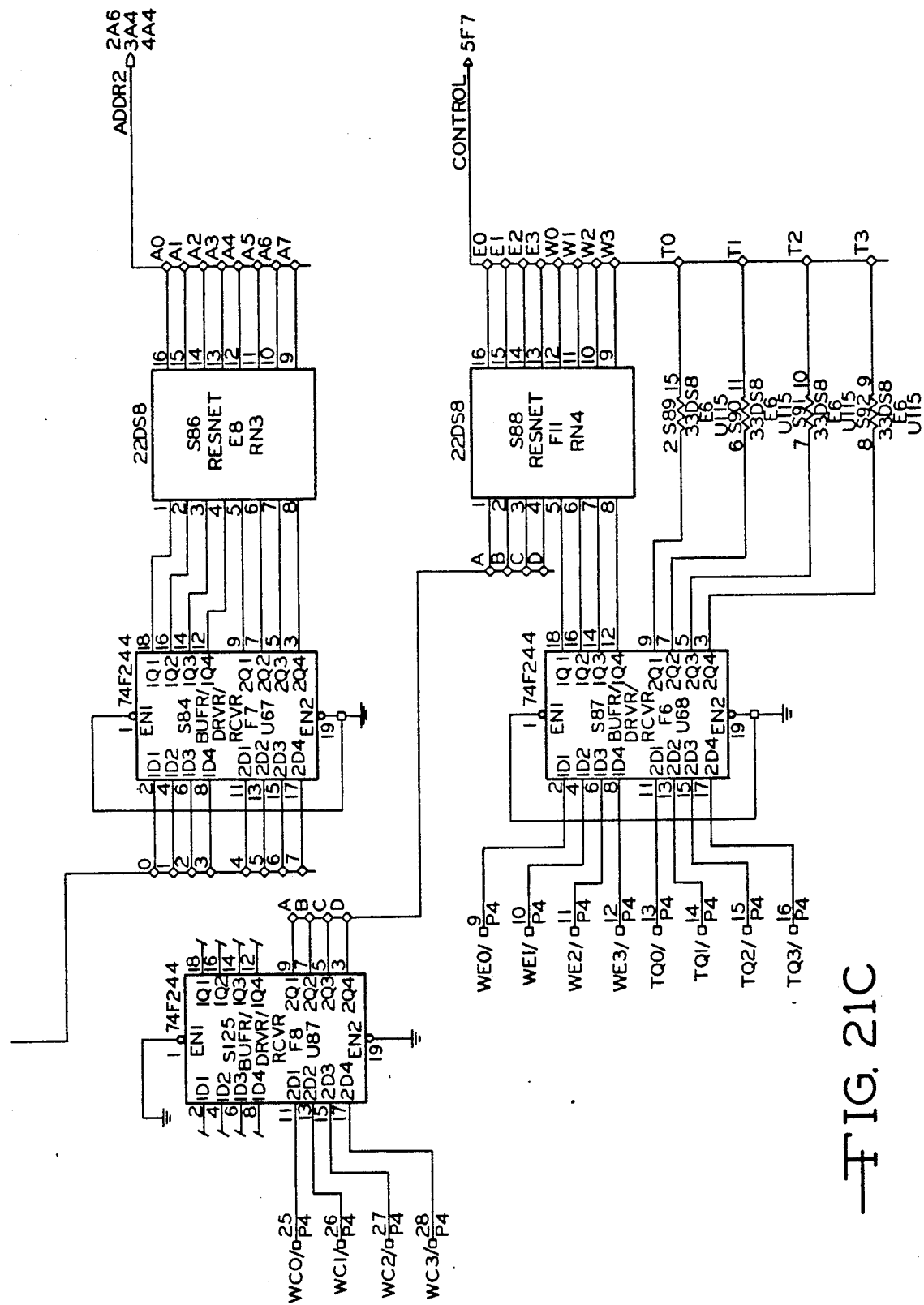
Figure 21D:
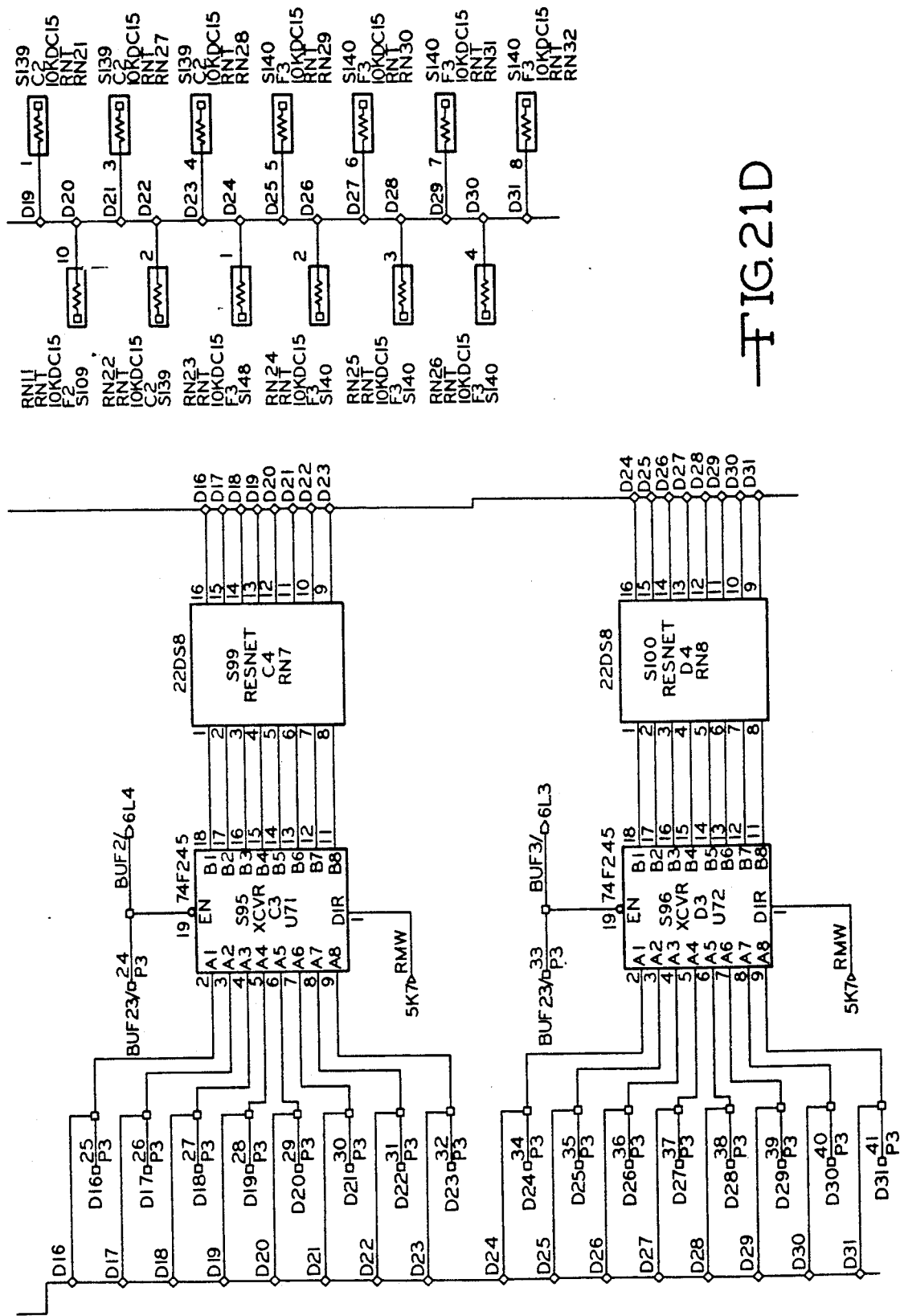
Figure 22A:
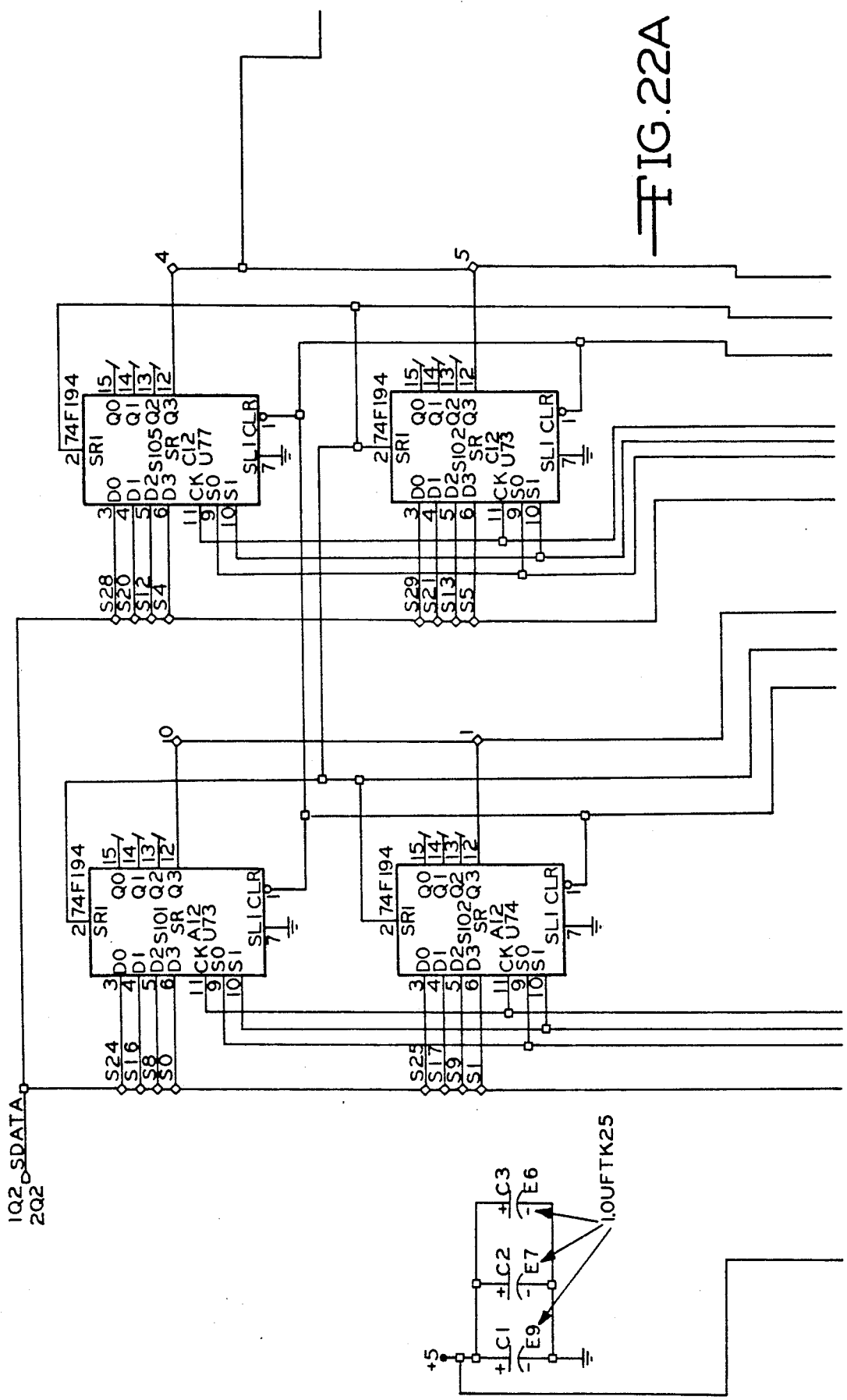
FIGS. 22A, B, C and D are schematics showing the Image Data Shift Register circuitry for the Image Memory Array of the present invention.
Figure 22B:
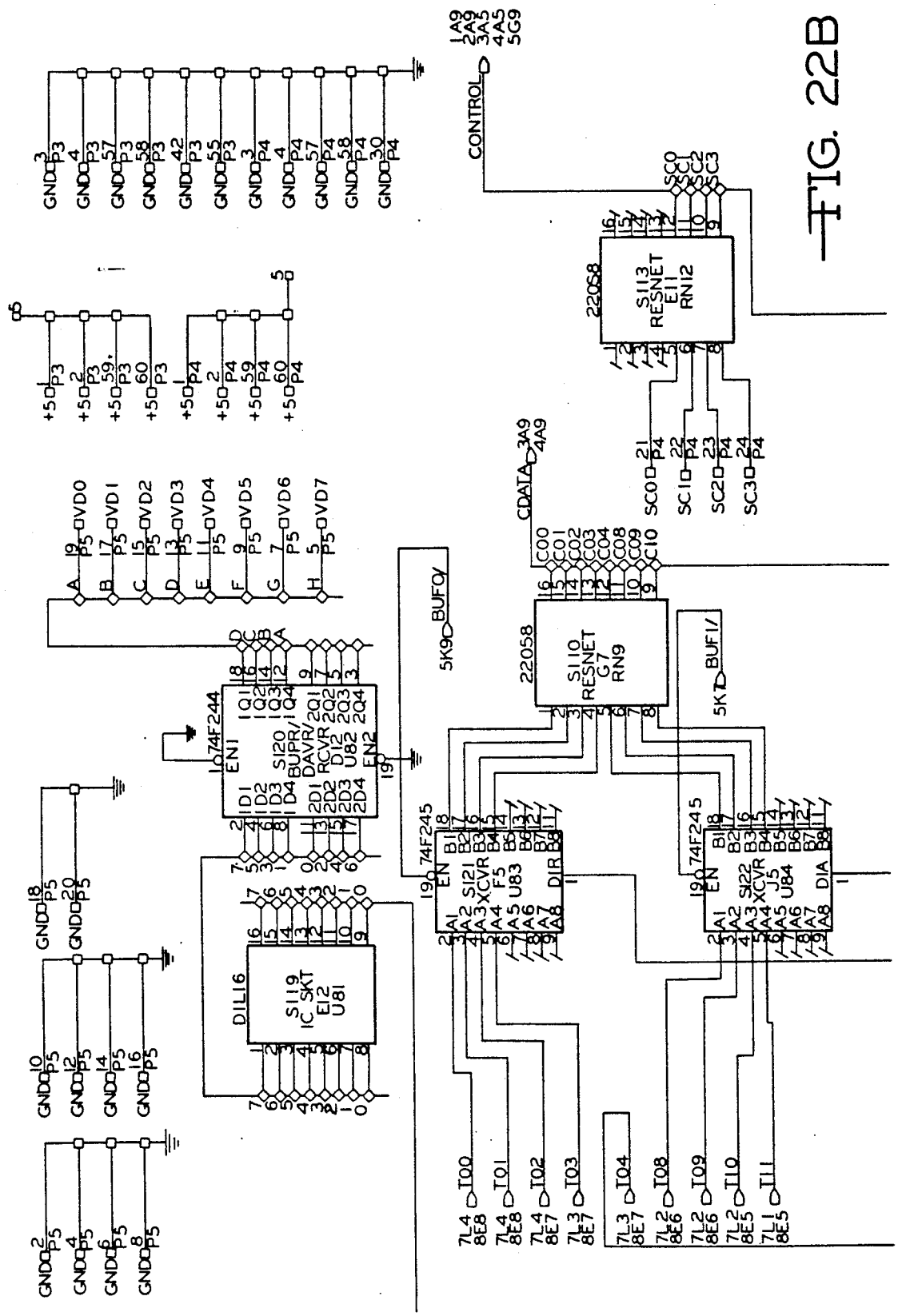
Figure 22C:
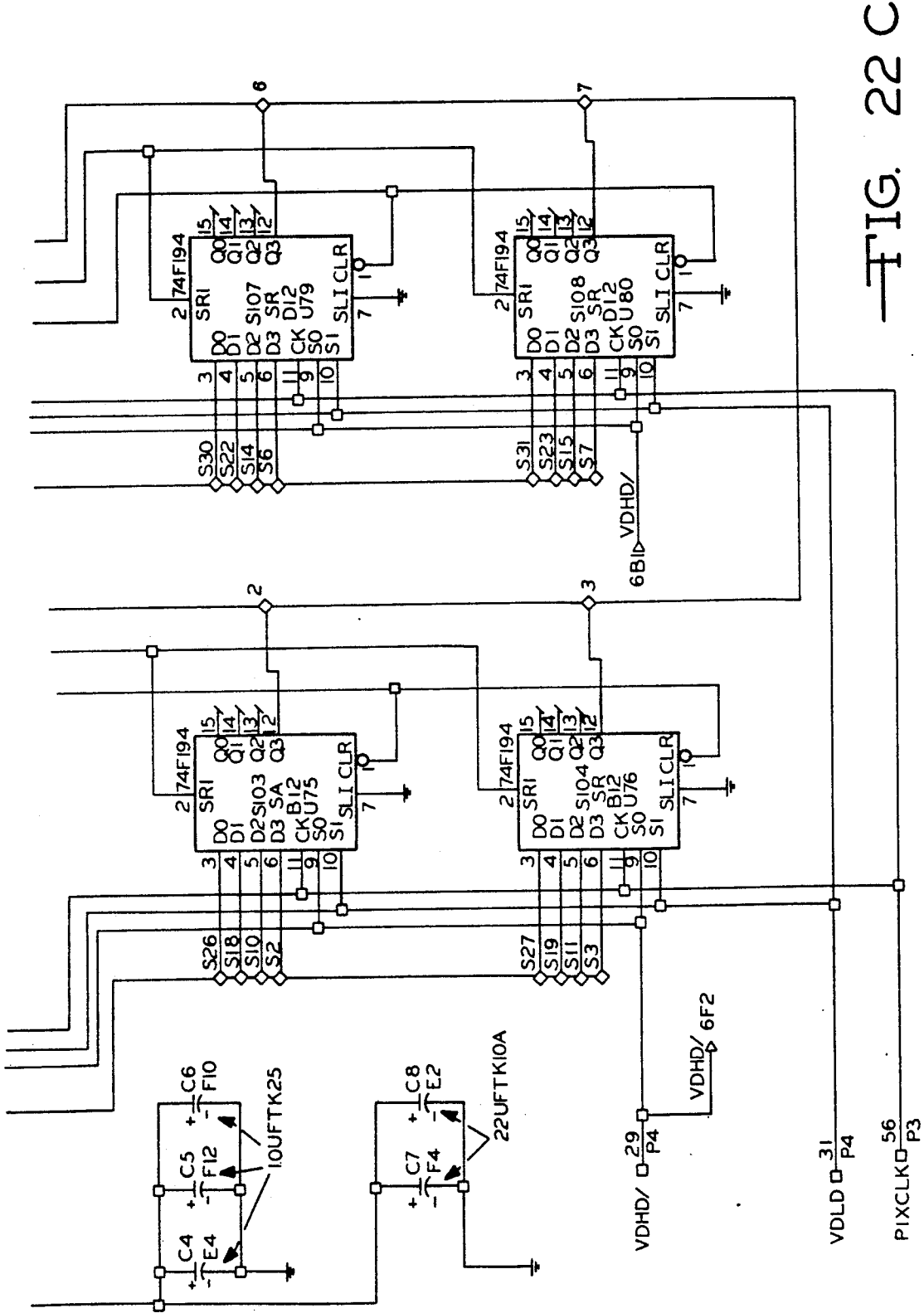
Figure 22D:
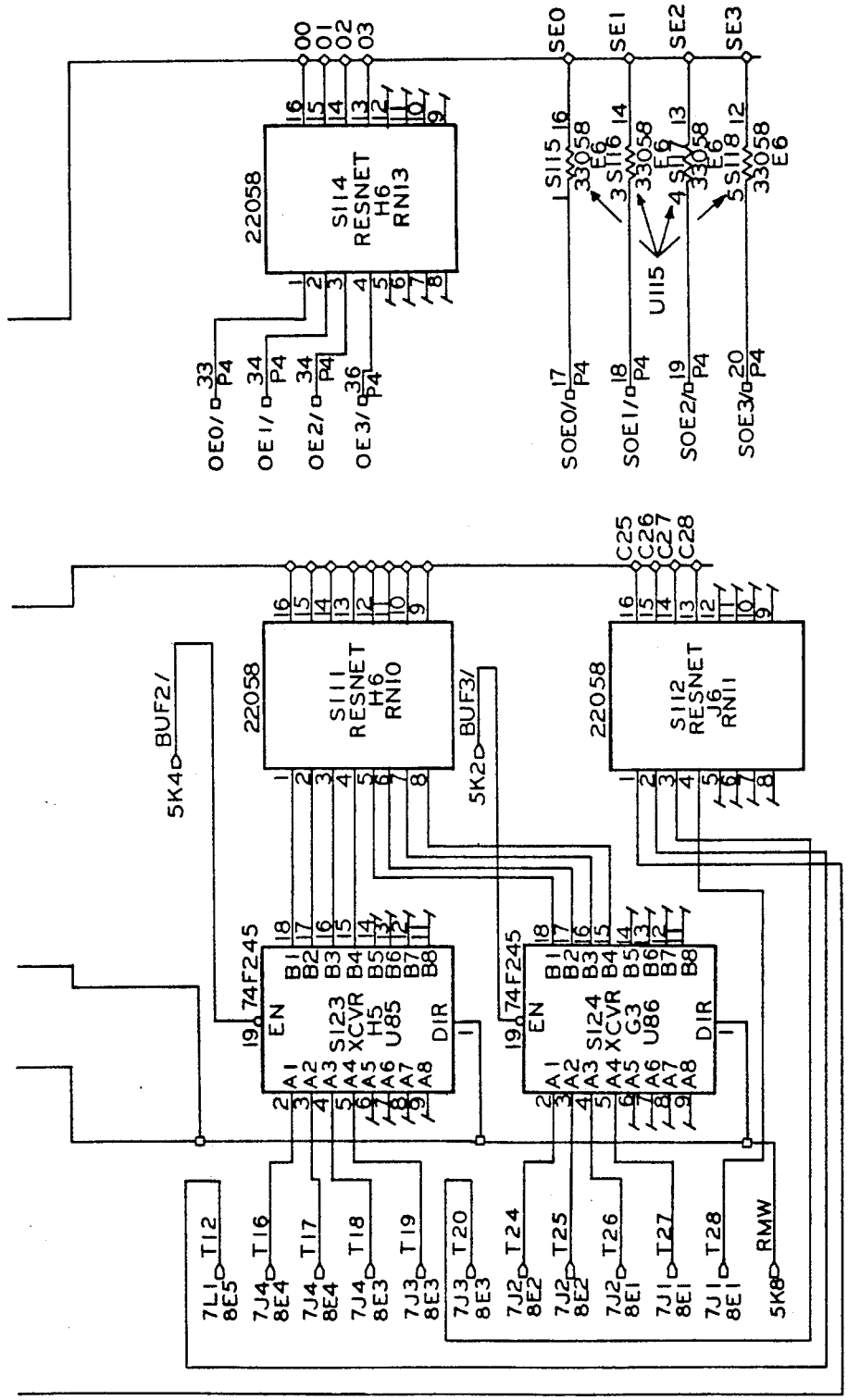
Figure 23:
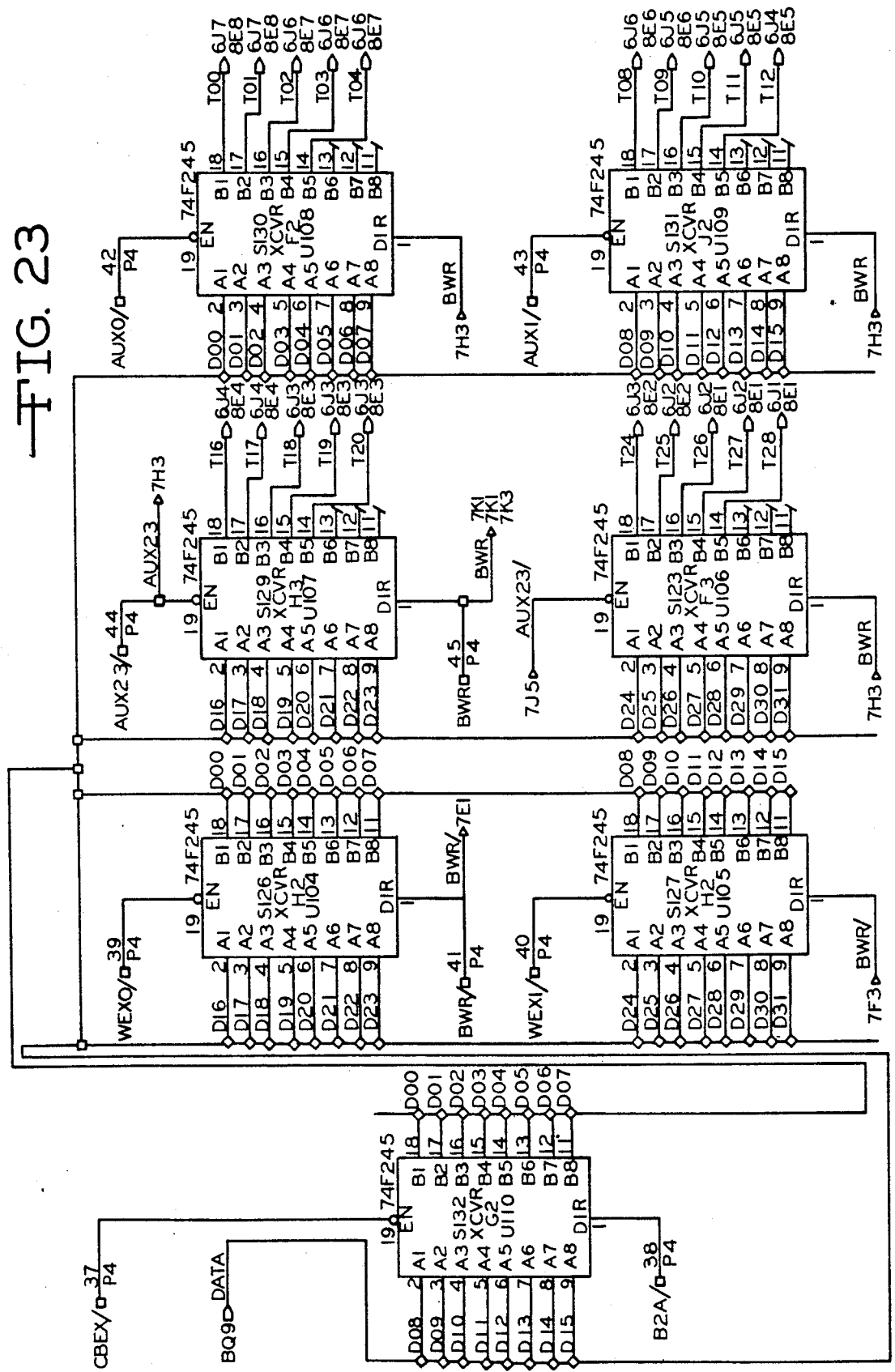
FIG. 23 is a schematic showing the Memory Array circuitry for the Image Memory Array of the present invention.

Referring to FIG. 4, laser imaging based upon detection of differences in optical density [i.e., wide angle forward light loss (FLL)] utilizes a blunt-cut high numerical aperture optical fiber faceplate 24 to collect and transmit light to the PMT 28. However, for imaging fluorescence emissions the primary beam is initially blocked on axis by introducing a bias end cut on the optical fibers. Referring to FIG. 11, the acceptance cone of the component fibers is "tipped" by angle B which is related to the bias end cut angle A as follows:

$$B = \sin^{-1}[(N_2/N_1) \sin A] - A$$

where $N_1$ and $N_2$ are the indices of refraction of air and the fiber core respectively. The numerical aperture is not significantly changed when A is approximately 30 degrees and, therefore, the light gathering power of the fibers is not diminished when the incidence angle of the excitation beam remains close to 90° however, the energy at the PMT is reduced more than 99%.

The PMT 32 is a high gain, low noise unit (Hamamatsu) having a 300–650 nm response (max. 400 nm) typically operated at 600 to 1250 volts. It is critical that transmitted light be diffused uniformly across the 2 inch diameter PMT 32 window to minimize variations in output related to spot position on target plane. This is effectively accomplished by the combination of inherent annular ray rotation at fiber output the optical and the diffusion assembly 26 which includes the cylinderical internally reflective coupling 28.

Figure 5:
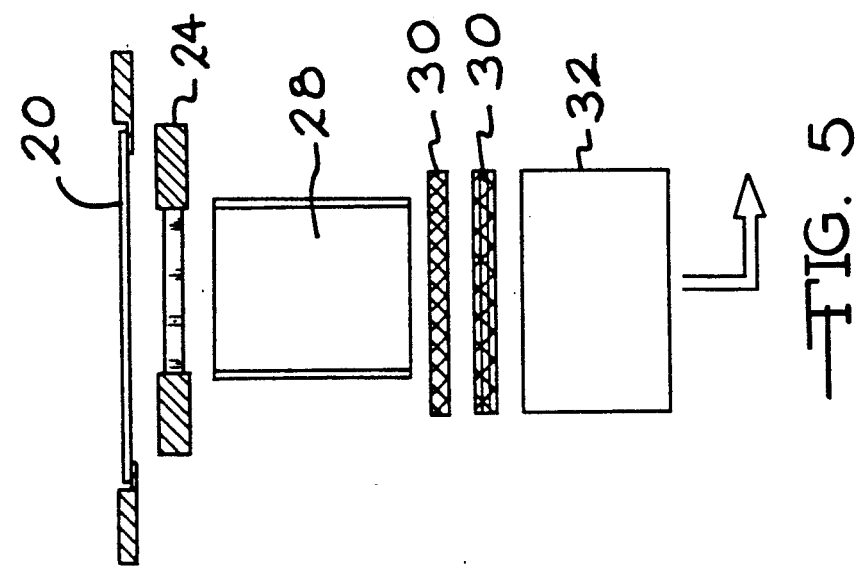
FIG. 5 is a schematic illustration of a typical detector assembly as used with the present invention.

Referring now to FIG. 5, the basic detector assembly 22 for standard densitometric imaging of translucent objects by a laser beam is shown. The detector assembly includes a blunt-cut optical fiber faceplate 24 and a diffusion assembly 26 composed of a internal reflectance tube 28 and a pair of flashed opal diffusion filters 30 and a photomultiplier tube 32.

Figure 6:
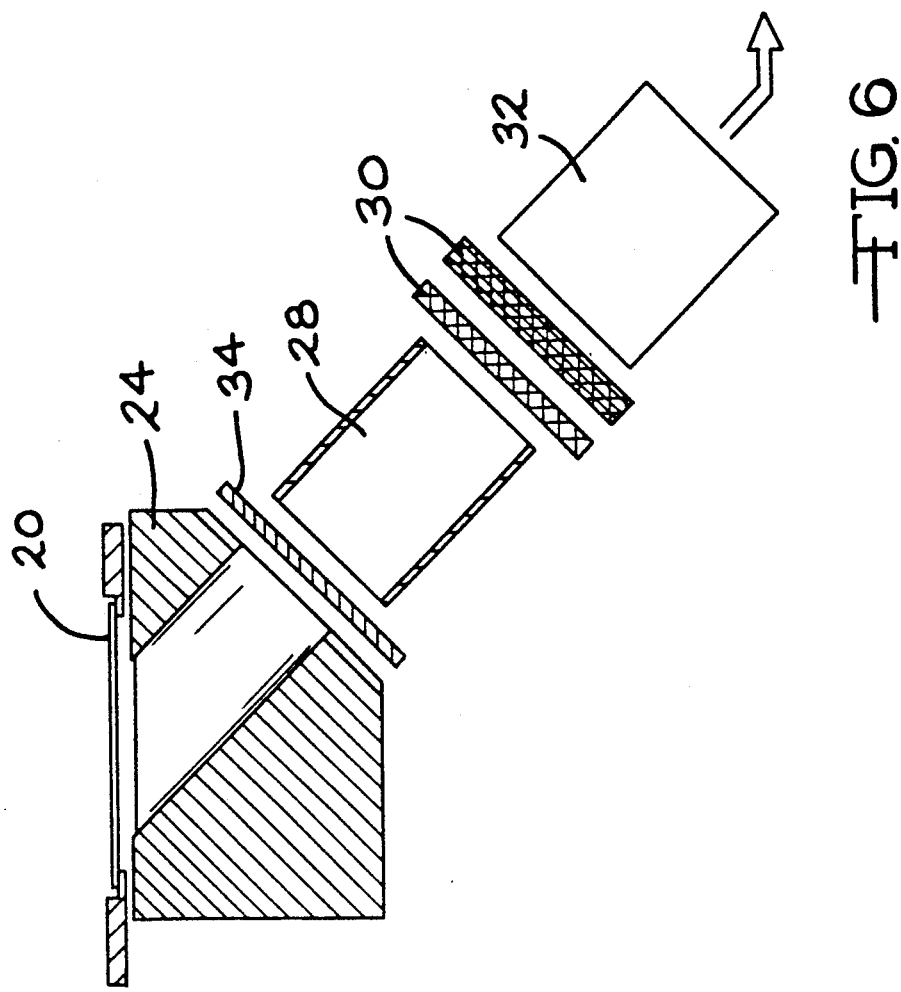
FIG. 6 is a schematic illustration of a detector assembly for use with the present invention in detecting fluorescence and forward light scatter.

Referring to FIG. 6, the basic detector assembly 22 is modified by the introduction of a dielectric interference filter 34 designed to transmit forward scatter. The critical angle of the interference filter 34 is matched to the emission cone of the optical fibers, thus eliminating primary light and accepting forward scatter. The interference filter 34 can also be replaced by a Bragg Diffraction filter which allows for 100% transmission of light with the exception of a narrow band. The Bragg Diffraction Filter has a $10^{-16}$ blocking ability.

When it is desirable to image both fluorescence and forward light scatter the standard blunt-cut fiber faceplate is replaced by a bias-end cut optical fiber faceplate 36 and the interference or dielectric filter 34 as shown in FIG. 6. When it might be desirable to capture images based on optical density and forward light scatter, the interference filter 34 can be placed between the standard blunt-cut fiber faceplate 24 of FIG. 5 and the internal reflecting tube 28. The addition of the interference filter 34 permits the imaging of forward light scatter with both types of optical fiber faceplates.

Referring to FIG. 7, the concept of using the interference filter 34 to detect forward light scatter is shown.

The interference filter 34 can be optically tuned to detect forward scatter of a variety of discrete images having discrete ranges of forward scatter angles. In the special instance where the "exclusion" cone determined by the critical angle of the interference filter 34 exceeds the maximum emission angle of the optical fibers, no light of the primary wavelength passes through to the photomultiplier tube 32. If the interference filter 34 is designed to block only the wavelength of the laser beam and pass other wavelengths, the imaging of laser-excited fluorescence from the scanned target is possible. With the bias-end cut fibers the only light that is propagated to the PMT is scattered laser light from the target and fluorescence emission. Selection of scatter versus fluorescence signals is then determined by the variable diffraction filter characteristics. The forward light scatter angle window is variable and determined by the combination of fiber NA and the characteristics of the filter incorporated in the assembly.

For the special instances of fluorescence shadowing and forward scatter fluorescence shadowing, the detector assembly 22 is further modified by placing a fluorescence sensor between the interference filter 34 and the diffusion assembly 26. For the process of fluorescence shadowing the interference filter 34 is tuned to pass densitometric images to the fluorescence sensor consisting of a material such as dyed glass which fluorescence at wavelengths accepted by the photomultiplier tube 32. Images are formed by placing the densitometric target over the detector assembly 22 and scanning the target. When it is desirable to perform the process of forward scatter fluorescence shadowing, the interference filter 34 is tuned to pass forward scatter images onto the fluorescent sensor which emits fluorescent signals to the PMT 32. The process of forward scatter fluorescence shadowing has achieved detection resolution of submicron particles in the target in the 0.2-1.0 um range.

It may be desirable to insert an F-theta collimating lens (not shown) between the beam controller 18 and the target plane 20. Such use of an F-theta lens will eliminate the changing angle of incidence of the beam of light 16 and direct the beam in a perpendicular orientation to the target plane 20 to ensure the accurate propagation of forward light scatter. The Z axis of the beam controller 18 can be preprogrammed to automatically correct for the predictable lack of flatness in the lens field and the resulting non-perfect image.

An alternative design of the optical fiber faceplate for use in the detection of fluorescence incorporates square optical fibers instead of round optical fibers. Square optical fibers can be used to propogate plane-polarized light by the phenomenon of fluorescence anisotopy.

The phenomenon of fluorescence anisotropy is the degree to which the fluorescence emission from a target is polarized relative to polarization of the excitation light. Measurement can be accomplished by simply determining the relative intensities of fluorescence emission with electric field vectors parallel and perpendicular to the electric field vector of the incident excitation light. A typical design of an instrument for such a purpose is presented in a paper by S. Kinoshita, T. Fukami, Y. Ido, and T. Kushida, published in *Cytometry*, Vol. 8, pp. 35-41, 1987. These authors define anisotropy, r, as $$r = (I_= - I_+)/(I_= + 2I_+)$$

where $I_=$ and $I_+$ are the fluorescence intensities with electric field vectors parallel and perpendicular to the electric vector of the incident excitation light.

The improved method makes use of the fact that square optical fibers having light absorbing cladding (i.e., extramural light absorbing material or E.M.A.) possess an unusual property when used to propagate plane-polarized light. As the plane of polarization of input light rotates about the axis parallel to the direction of propagation, the plane of polarization of light exiting the fibers also rotates as expected. However, unlike circular cross section optical fibers, an additional rotation is observed between plus and minus 20-25 degrees. This same phenomenon is observed using fibers without E.M.A., however, the range of differential rotation imparted on the emerging light is reduced to approximately +/-9 degrees.

Figure 8:
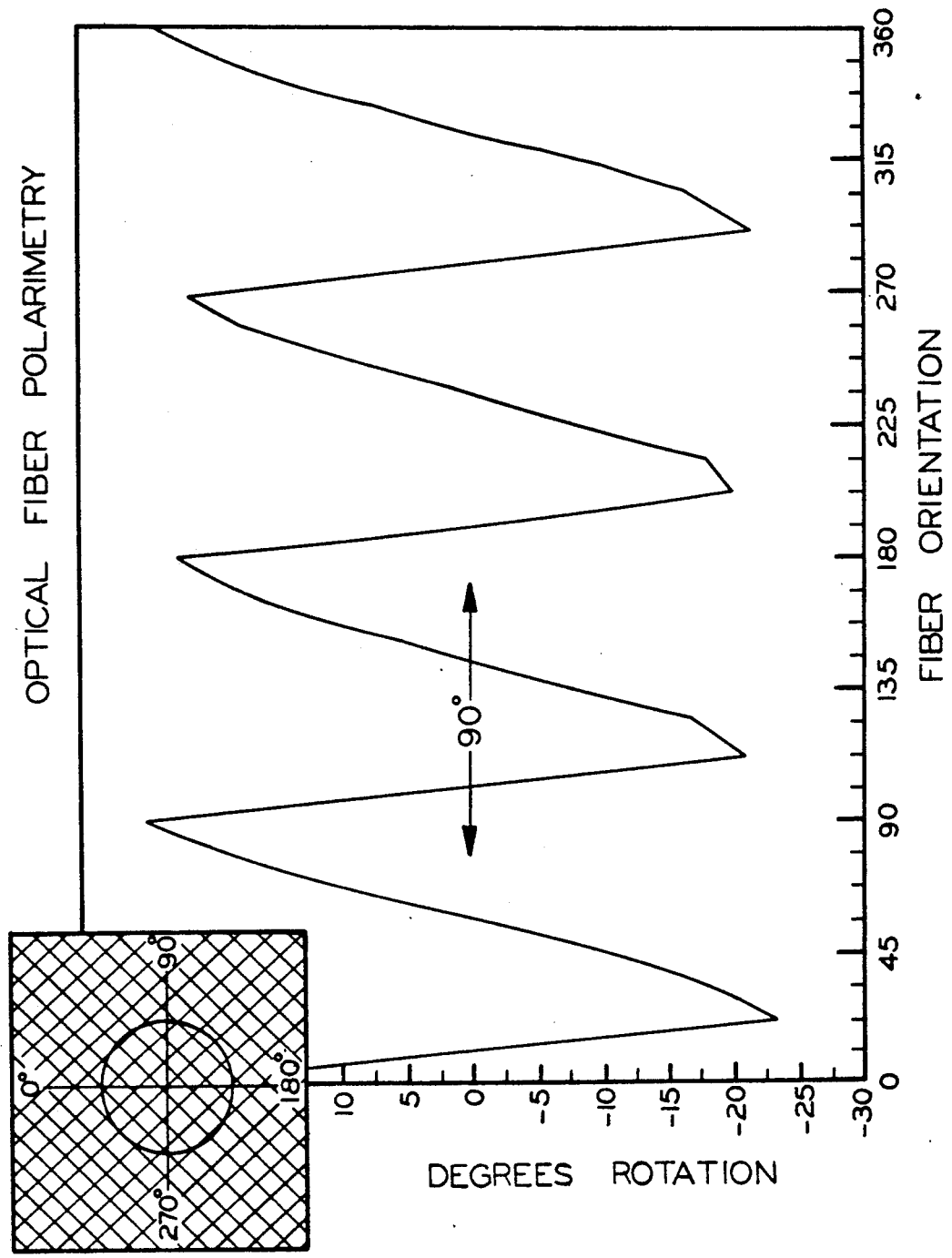
FIG. 8 is a graph showing optical fiber polarimetry for square cross-sectional optical fibers.

In effect, the use of square optical fibers with E.M.A. provides a novel means of amplifying a rotation in fluorescence emission polarization, or the degradation of polarization relative to excitation light. This is a consequence of the fact that the square optical fibers tend to rotate the plane of polarization in the direction of a plane parallel with either diagonal inscribed within the square core geometry in a manner illustrated in FIG. 8. Therefore, if incident fluorescent light is rotated (e.g., +7 degrees relative to the excitation beam), the emergent light from the fiber optics will be rotated approximately +17 degrees as illustrated in FIG. 9. This additional rotation is imparted as a result of the square cross section geometry and is enhanced by the presence of E.M.A.

Figure 10A:
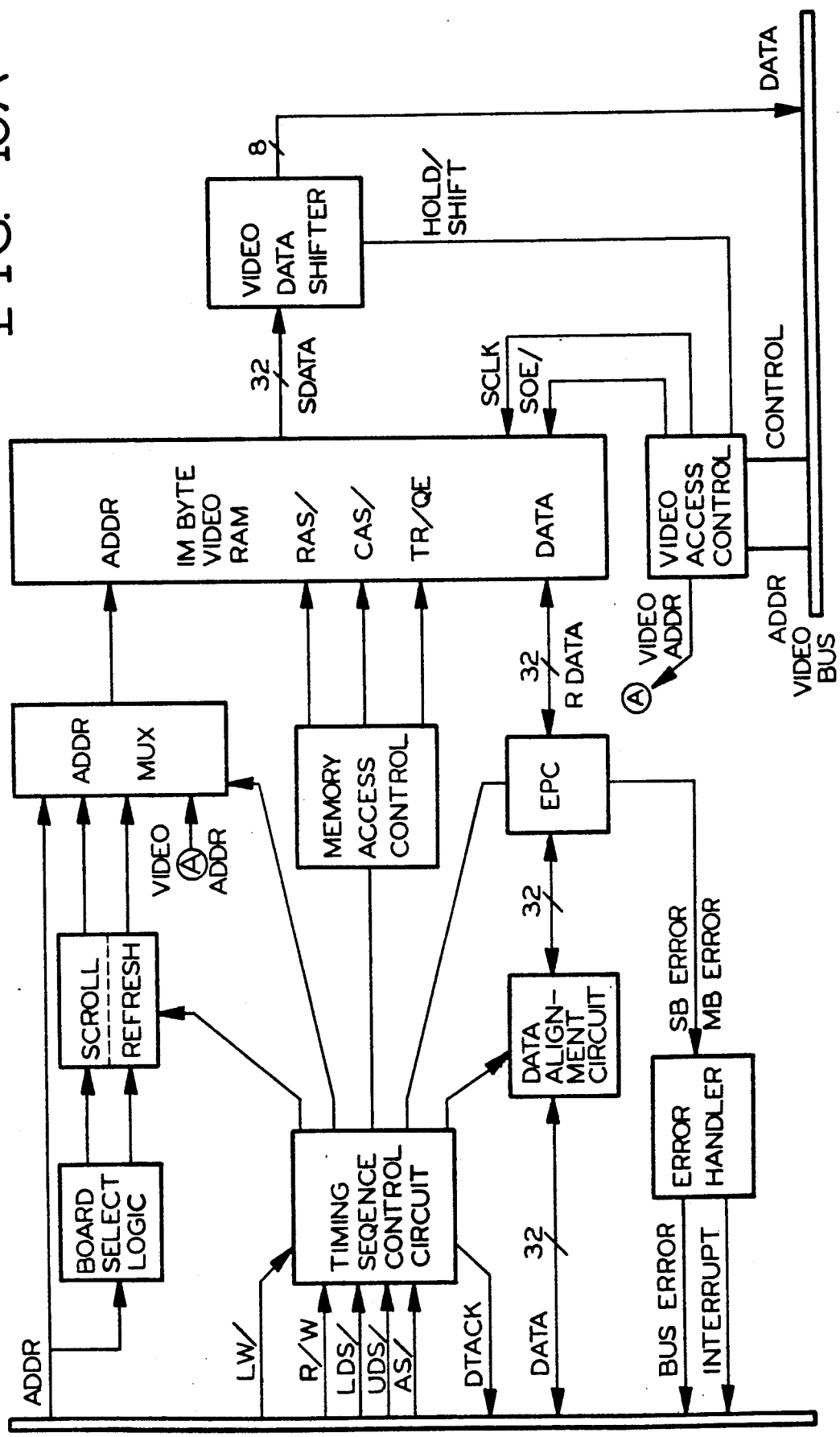
FIG. 10A is a schematic block diagram of the image memory controller and image memory array for the imaging system of the present invention.
Figure 10B:
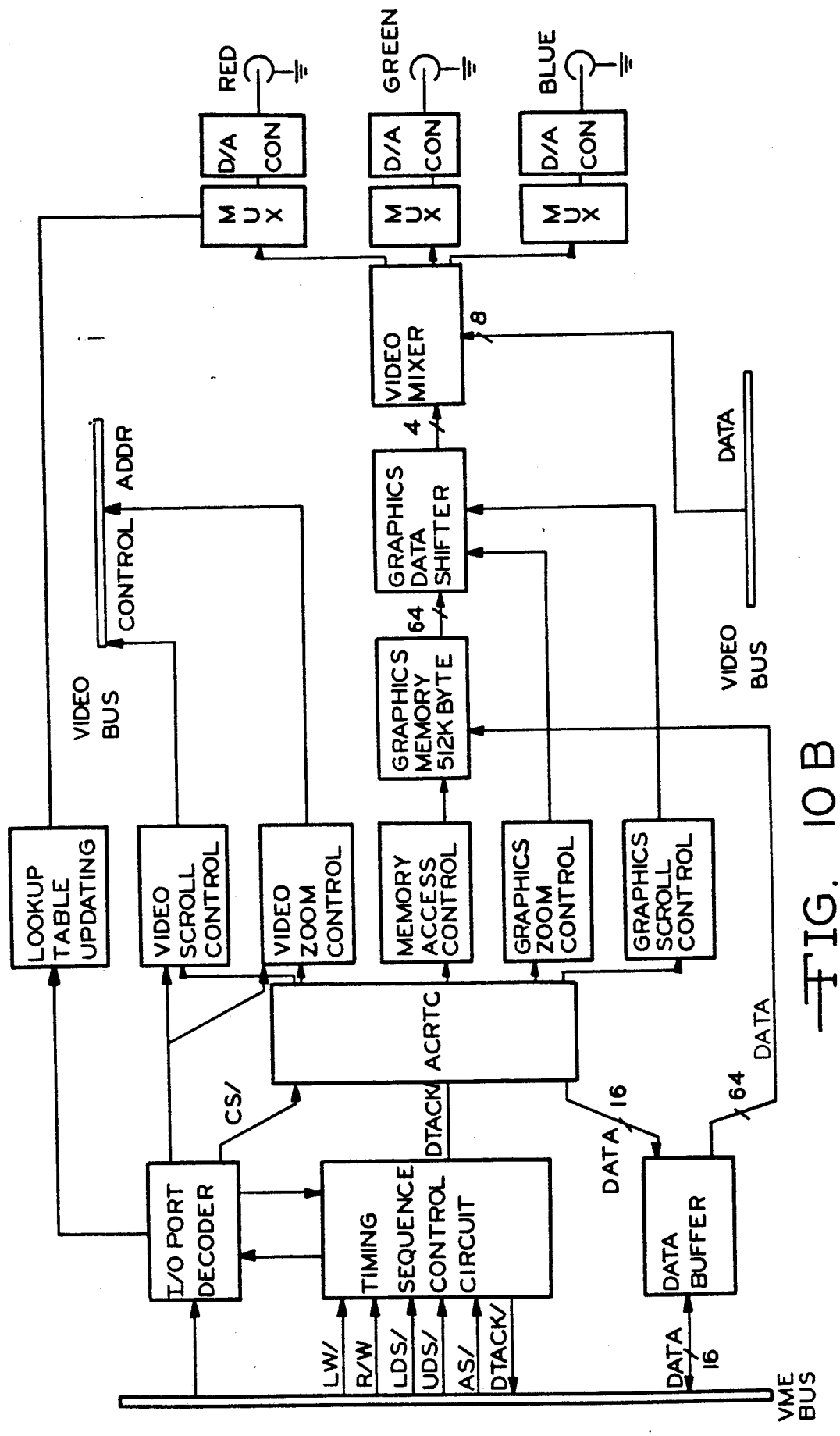
FIG. 10B is a schematic block diagram of the CRT controller and graphics memory array for the imaging system of the present invention.

Referring now to FIGS. 10A and 10B, a schematic block diagram of the computer support system is shown. The processor board is based on the Motorola 68020 32 bit microprocessor and the 68881 floating point co-processor. It provides data collection at a burst rate of one and a quarter million 12 bit words per second with 256K bytes on board memory accessible with no wait states. A dual-ported memory card, designed to support the image updating via a random port while the display RAM features one megabyte dual-ported memory utilizing 32 64K×4 video RAM chips, two bit error detection and one bit error correction circuitry is provided. The sequential (video) port features a row-access to the video memory providing four 1024 pixels/line data in the internal buffer. With a newly designed VMEbus display controller board, several display options are provided for in the system: any continuous 8 bit display out of 16 bit video information available per pixel is under software control; two display formats are provided, 512×480 and 1024×960; B/W and color (true and pseudo) displays are provided; pixel resolution is user selectable 8 to 24 bits; zoom and scroll.

Referring to FIGS. 12-17, the image memory controller board is VME bus compatible. VME bus is a trademark of Motorola, Inc., and is also known as the IEC821 bus or the IEEE Pio14/DI.O. The VME bus defines an interfacing system used to connect data processing, data storage, and peripheral control devices in a closely coupled hardware configuration. The image memory controller board enables 8, 16 and 32 bit data bus structures. The controller board offers the following functions. A power-up SCRUB function is provided to fill the memory array with Hex value FF. This function is not performed when the board is used as a display memory. The SCRUB is used when the board is used as a conventional memory. An address range-select function is provided and is based on 1M byte blocks located on 1M boundries. For the 32 bit address configuration the upper 8 bits are fixed in a user programmable PAL. This allows for 16 switch selectable 1M byte ranges using the next lowest four bits. The 1M byte memory is located on a daughter card and is divided into four banks of 256K bytes each. Four fully decoded input/output ports are provided. The input/output ports are located in short address range only (the lower 16 bits), the upper 8 or 16 bits are fixed. The input/output ports provide the following various support functions: they enable and disable the EDC circuitry; they report erroneous addresses; and, they enable and disable the interrupt, overflow, single bit error, multibit error, register clear, bus error, system failure, and diagnosis functions. The memory can interrupt any processer card on the bus if there is a single bit error, multibit error or overflow, provided that the corresponding enabling bit has been activated. This is a vector interrupt (i.e., a vector will be supplied to the host processer during the interrupt acknowledge cycle). The interleaved memory access is supported. Such support makes it possible for 2 memory cards to supply 16 bits two bytes per pixel. All even bytes of the pixel are stored in one memory card and all odd bytes are stored in the other memory card.

Referring to FIGS. 18-33, the image memory array board connects to the image memory controller board by way of two 60 pin interboard connecters. The image memory array board contains 1M byte of memory divided into four banks. Each bank consists of 8 dual ported video DRAM (Dynamic Random Access Memory) chips (uPD 41264-15). The random access port of the memory is intended for use by the VME bus (processer or DMA). The sequential port is dedicated to the video display circuit. This is an 8 bit per pixel display system although 32 bits are read at a time from the video memory through the sequential port. A shift register stores the 32 bits that are read and then supplies them in groups of eight.

Figure 24B:
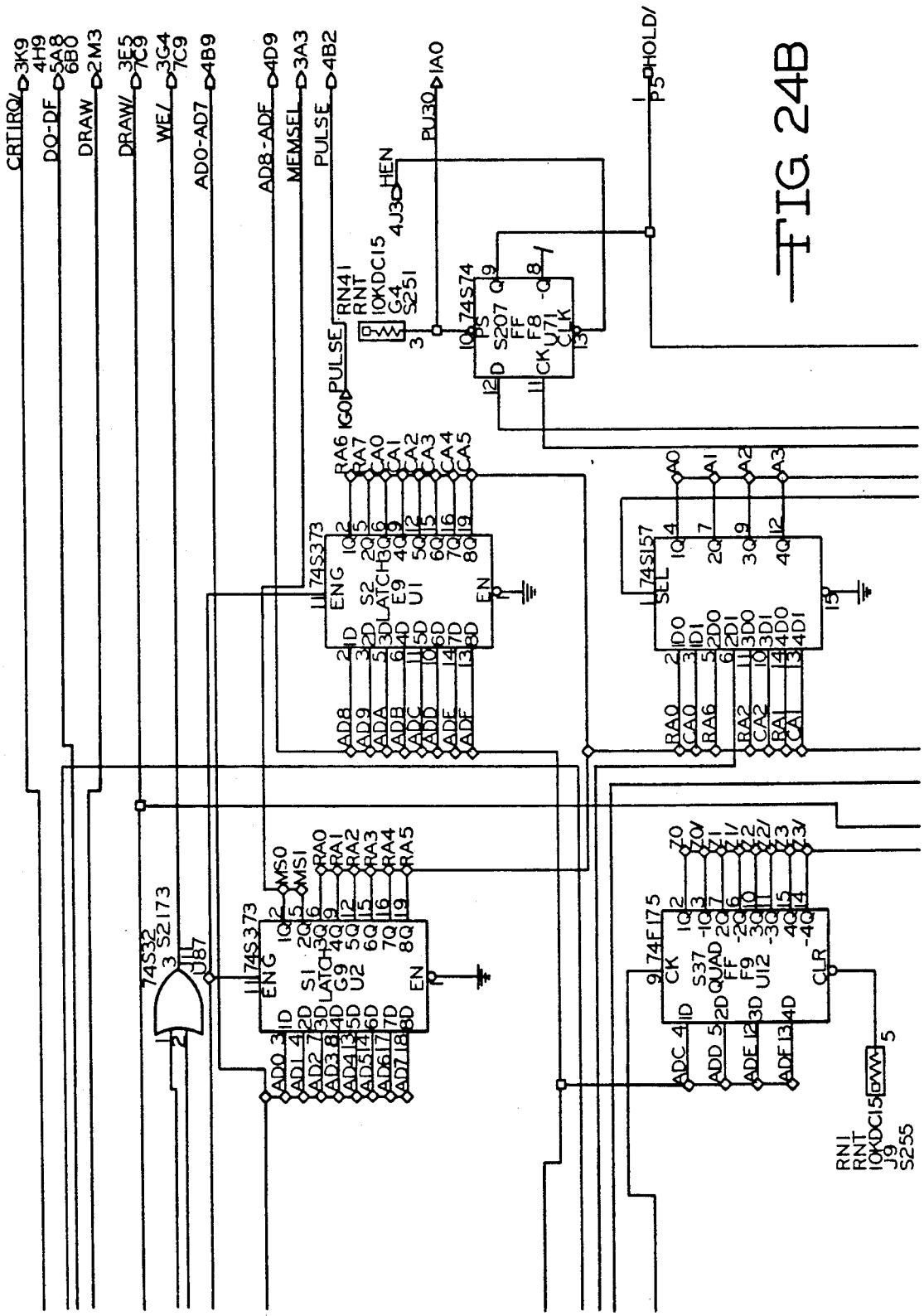
FIGS. 24A, B, C and D are schematics showing the Video Display Generator Interface circuitry for the CRT controller of the present invention.
Figure 24C:
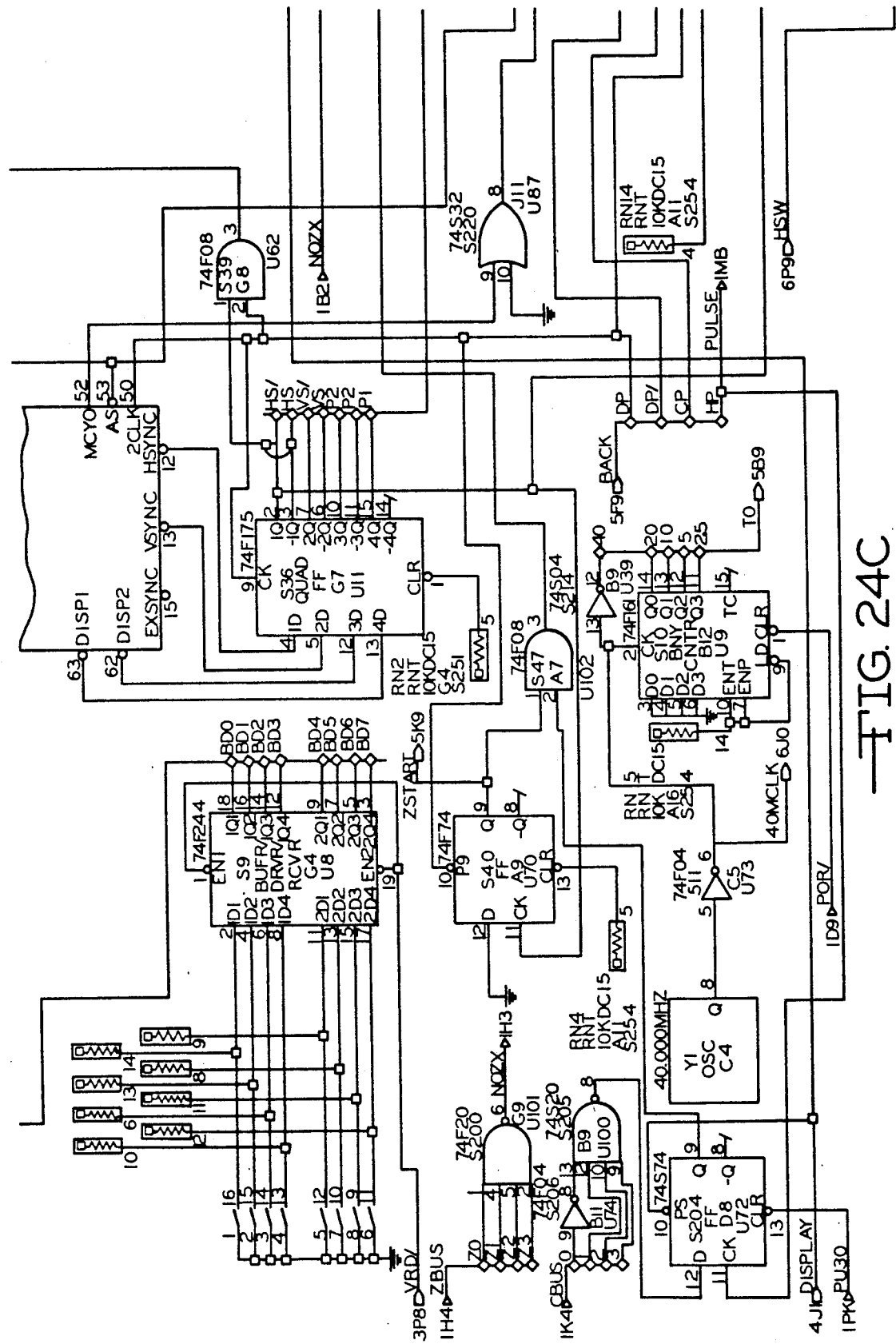
Figure 24D:
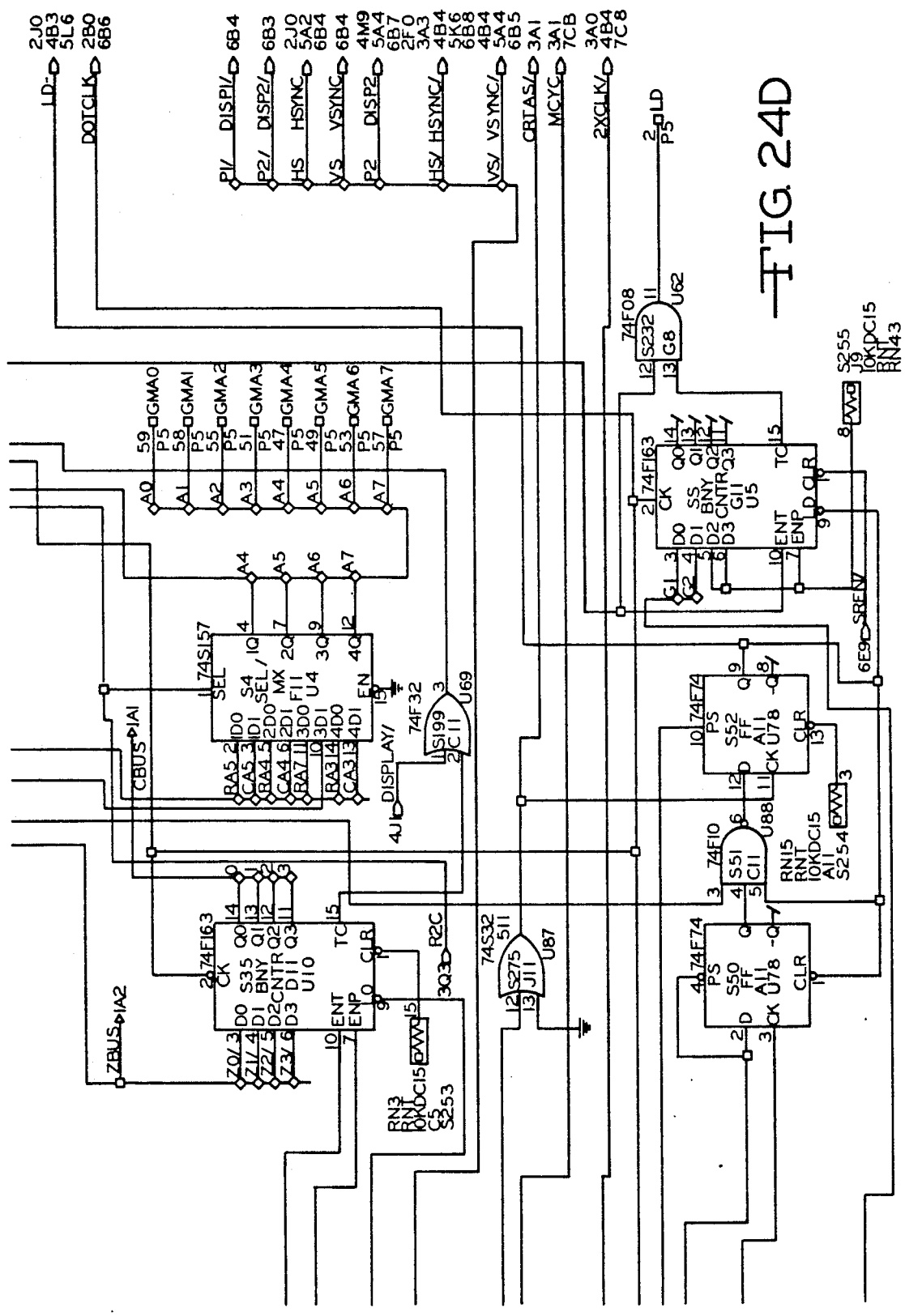
Figure 25A:
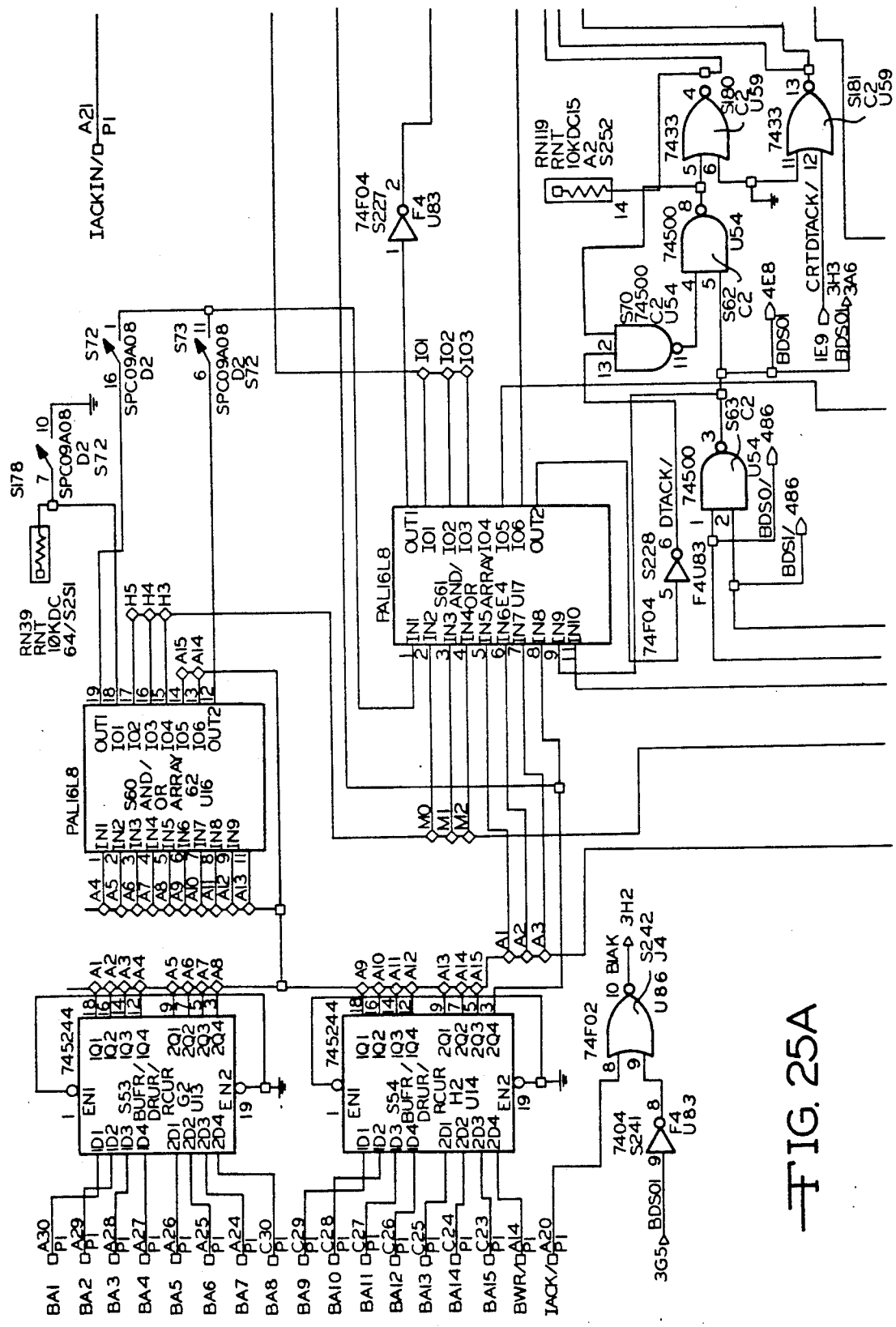
FIGS. 25A, B, C and D are schematics showing the Address Decoder, Graphics Memory Interface and Interrupt Request and Acknowledge circuitry of the CRT Controller of the present invention.
Figure 25B:
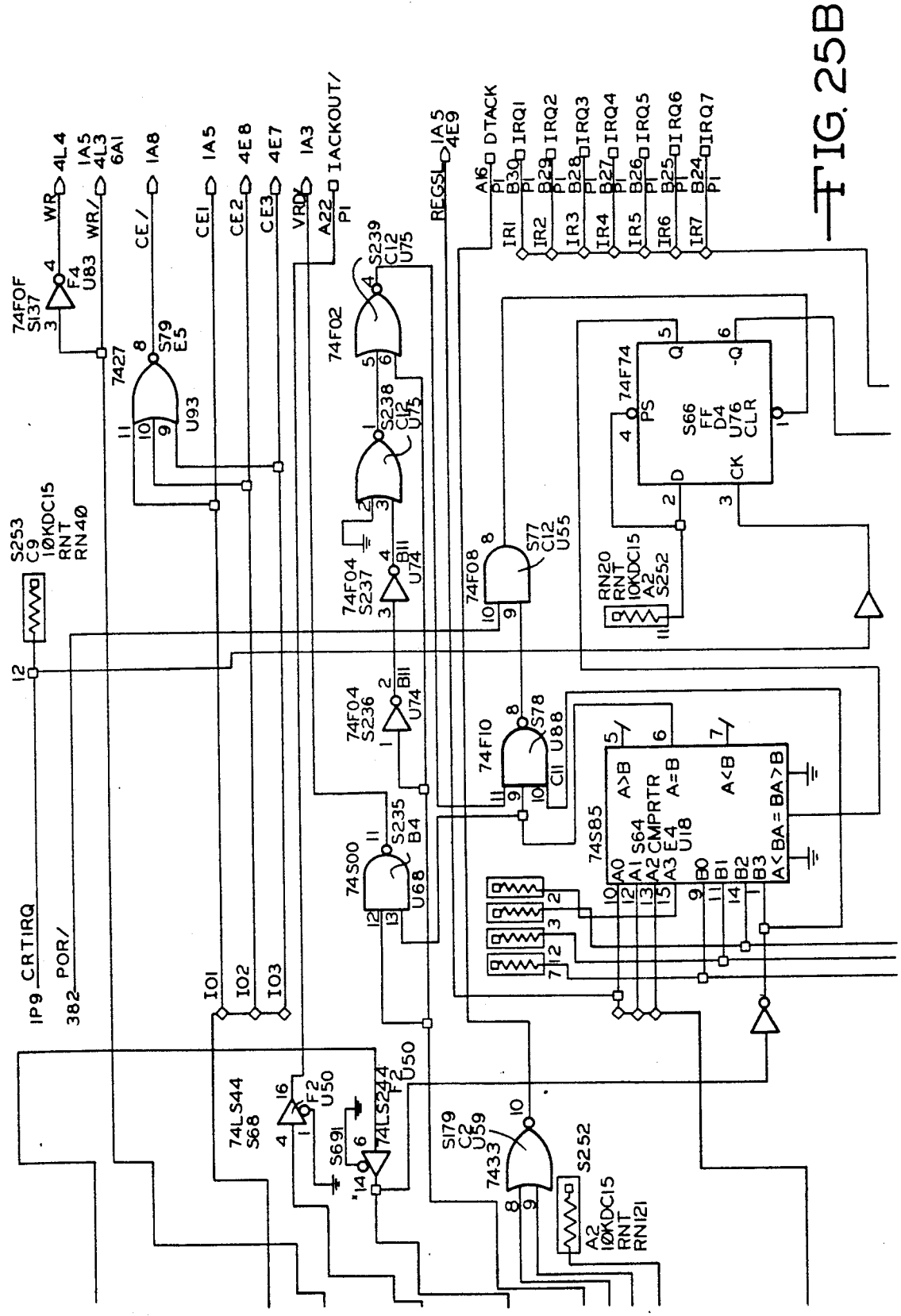
Figure 25C:
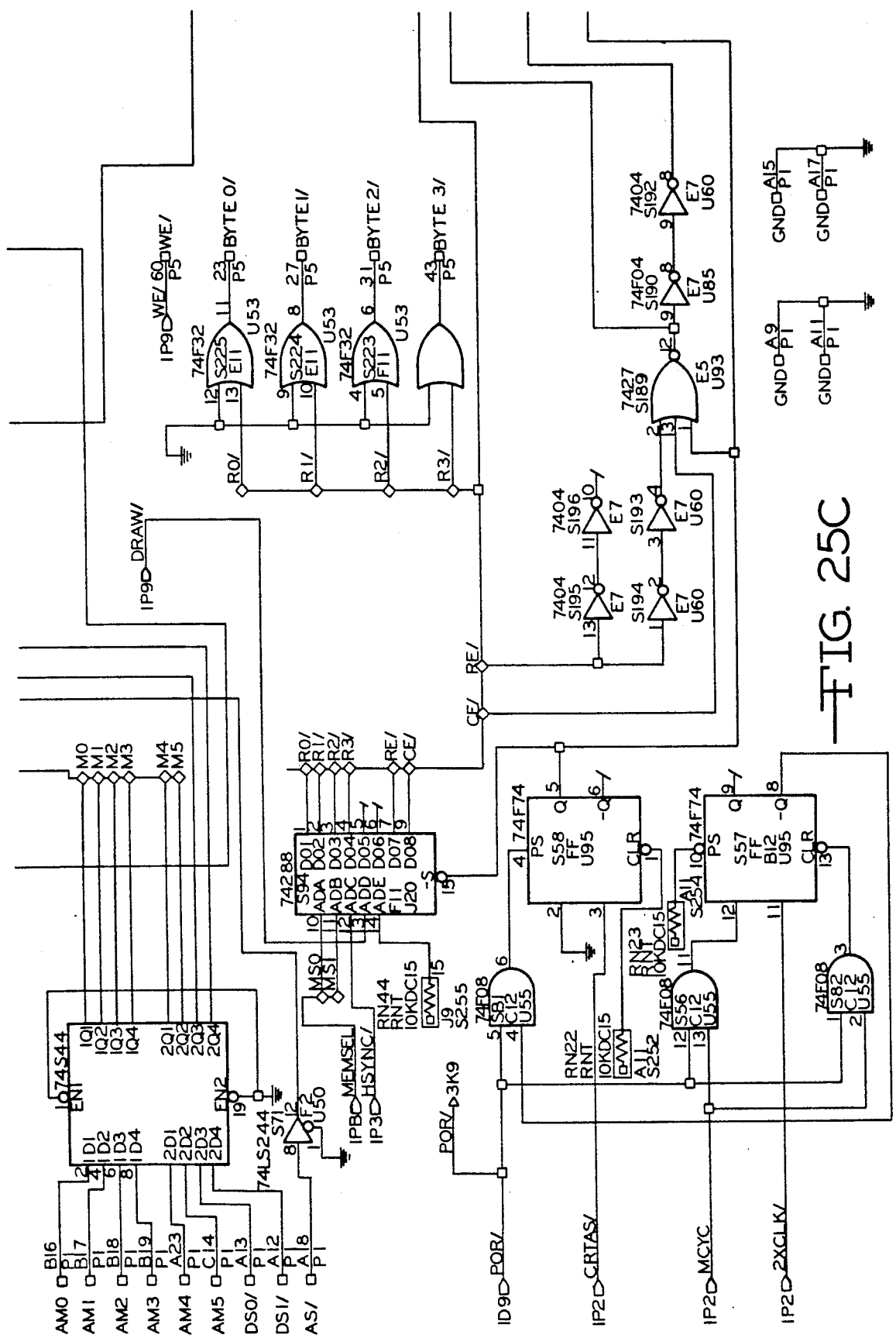
Figure 25D:
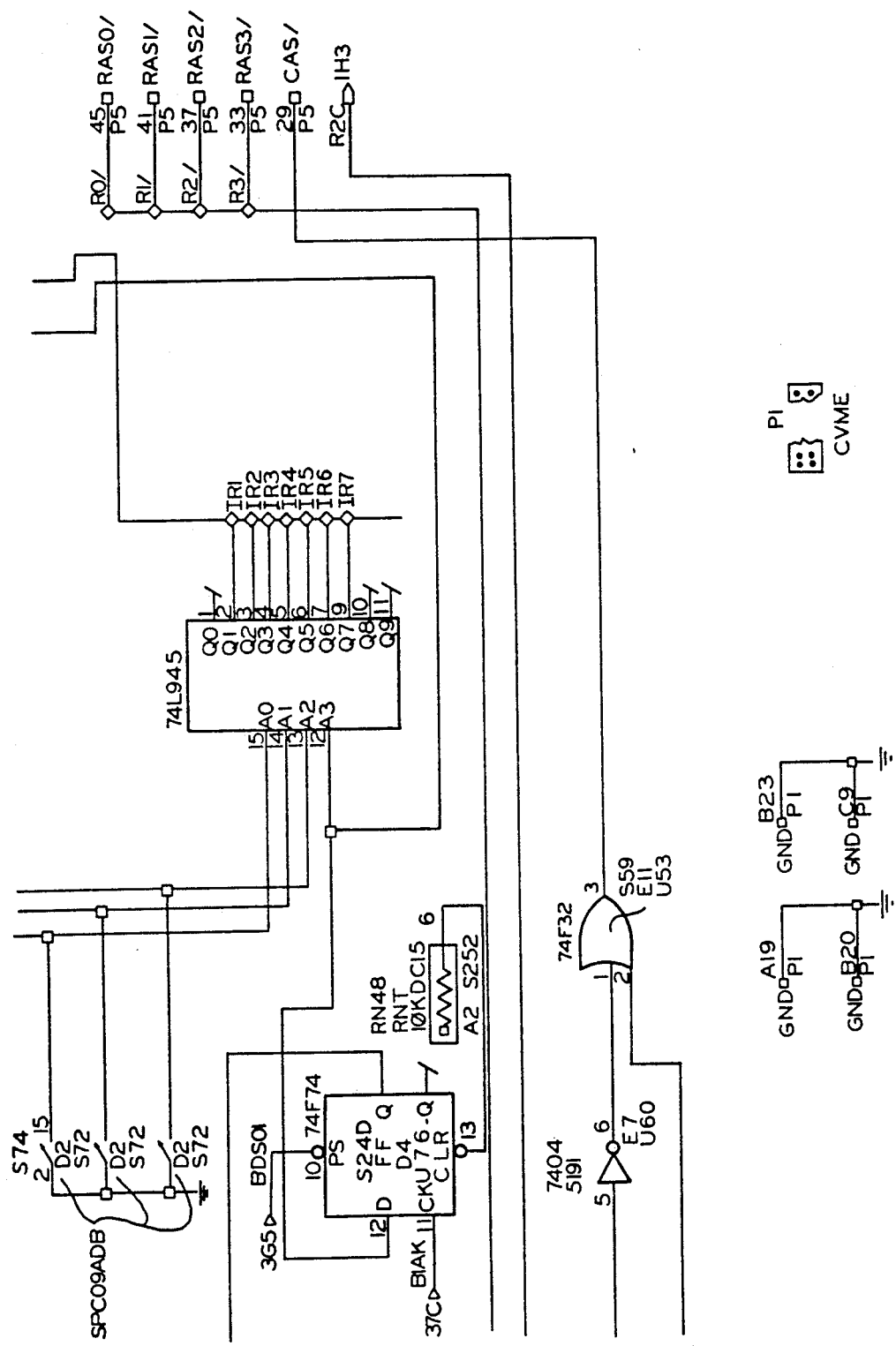
Figure 26A:
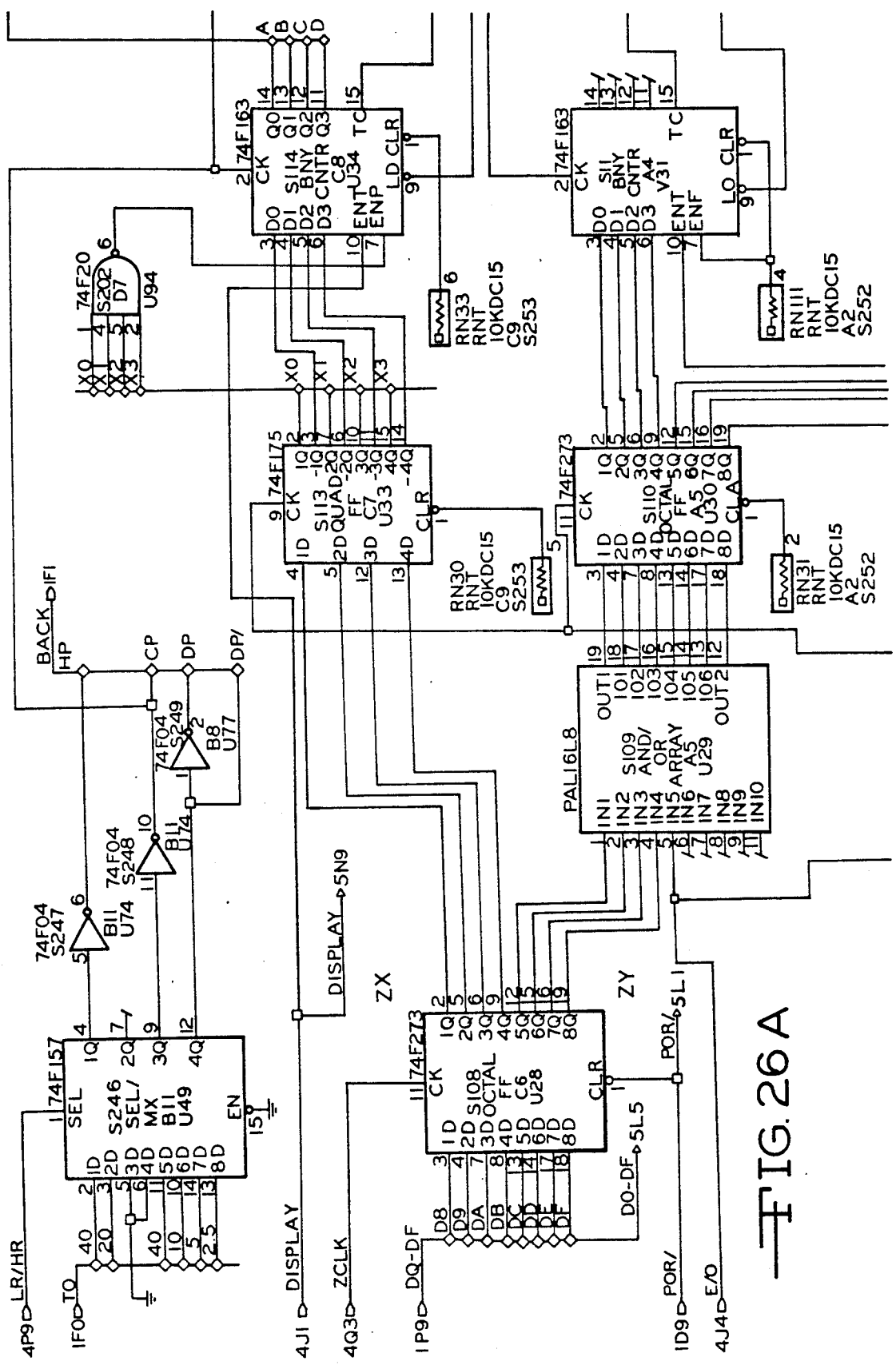
FIGS. 26A, B, C and D are schematics showing the Zoom Control and Look-up Table Circuitry for the CRT Controller of the present invention.
Figure 26B:
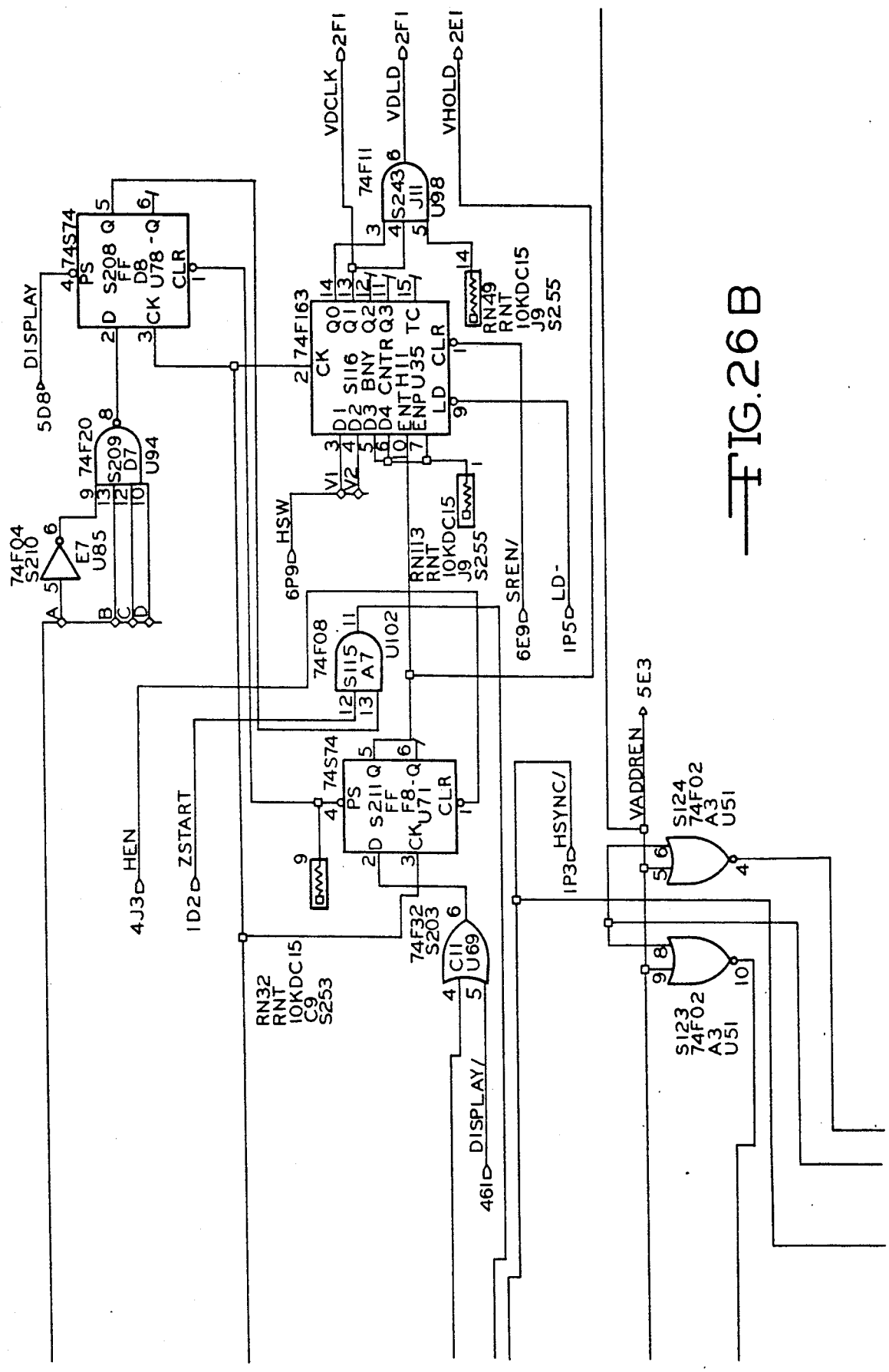
Figure 26C:
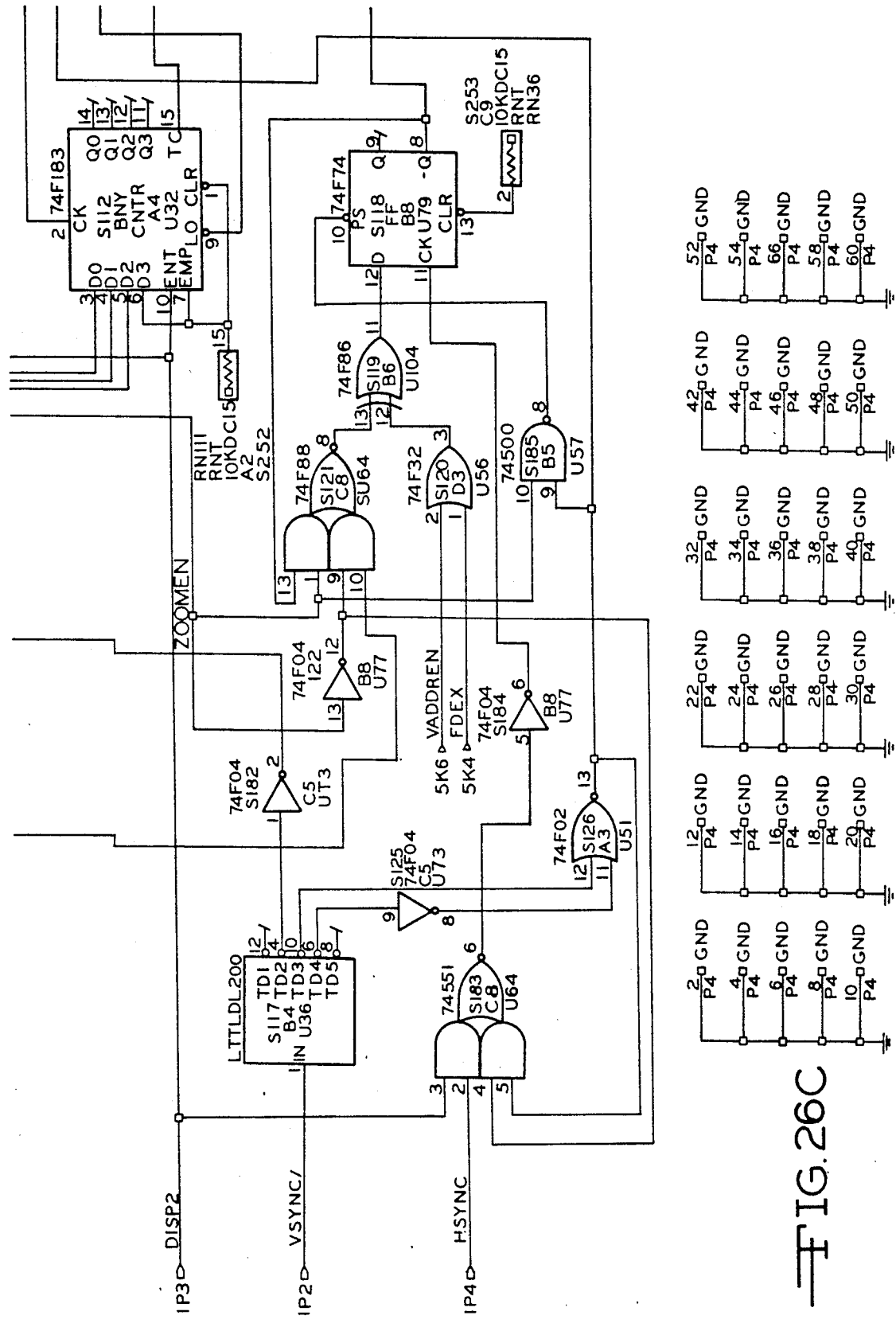
Figure 26D:
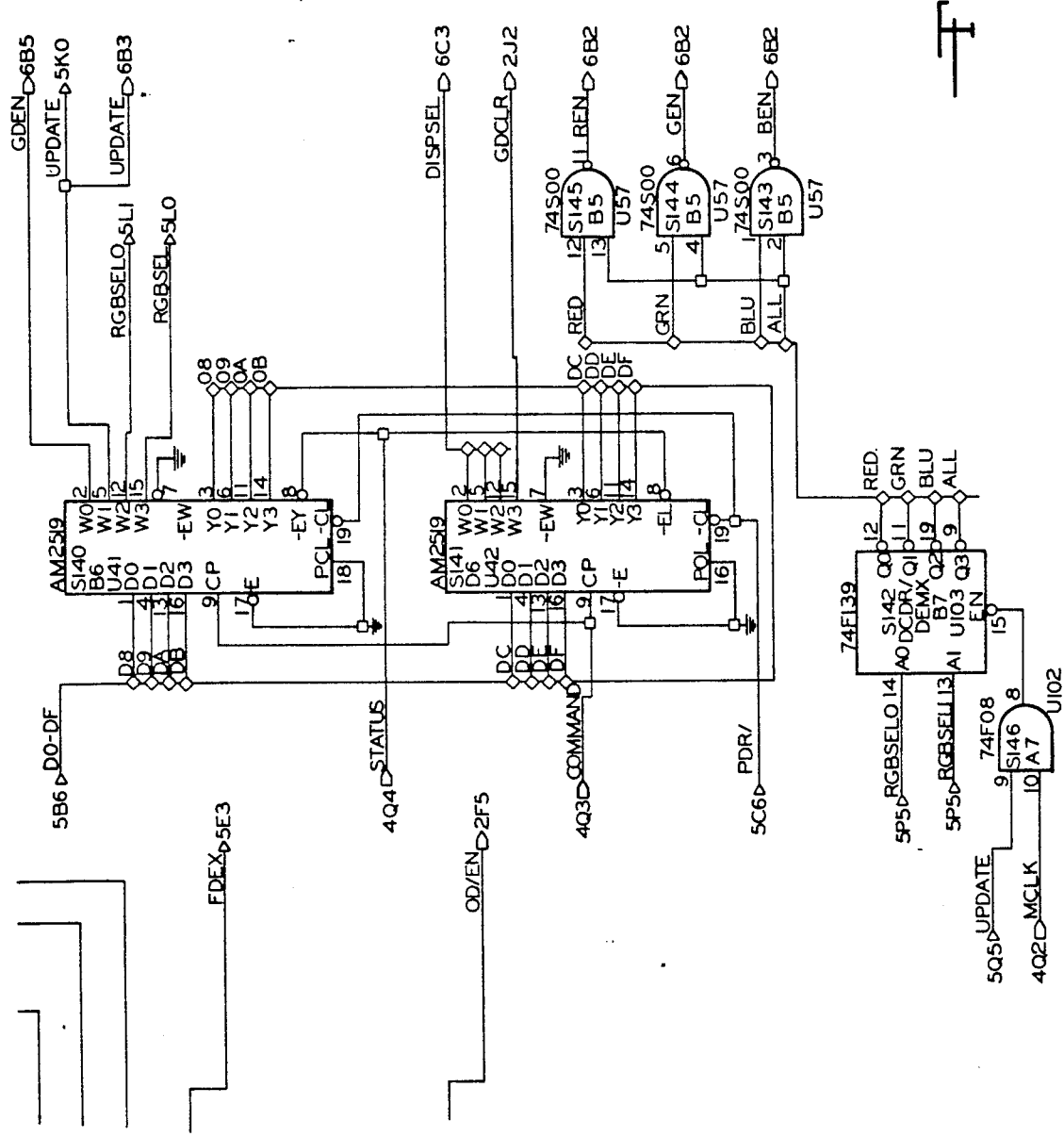
Figure 27A:
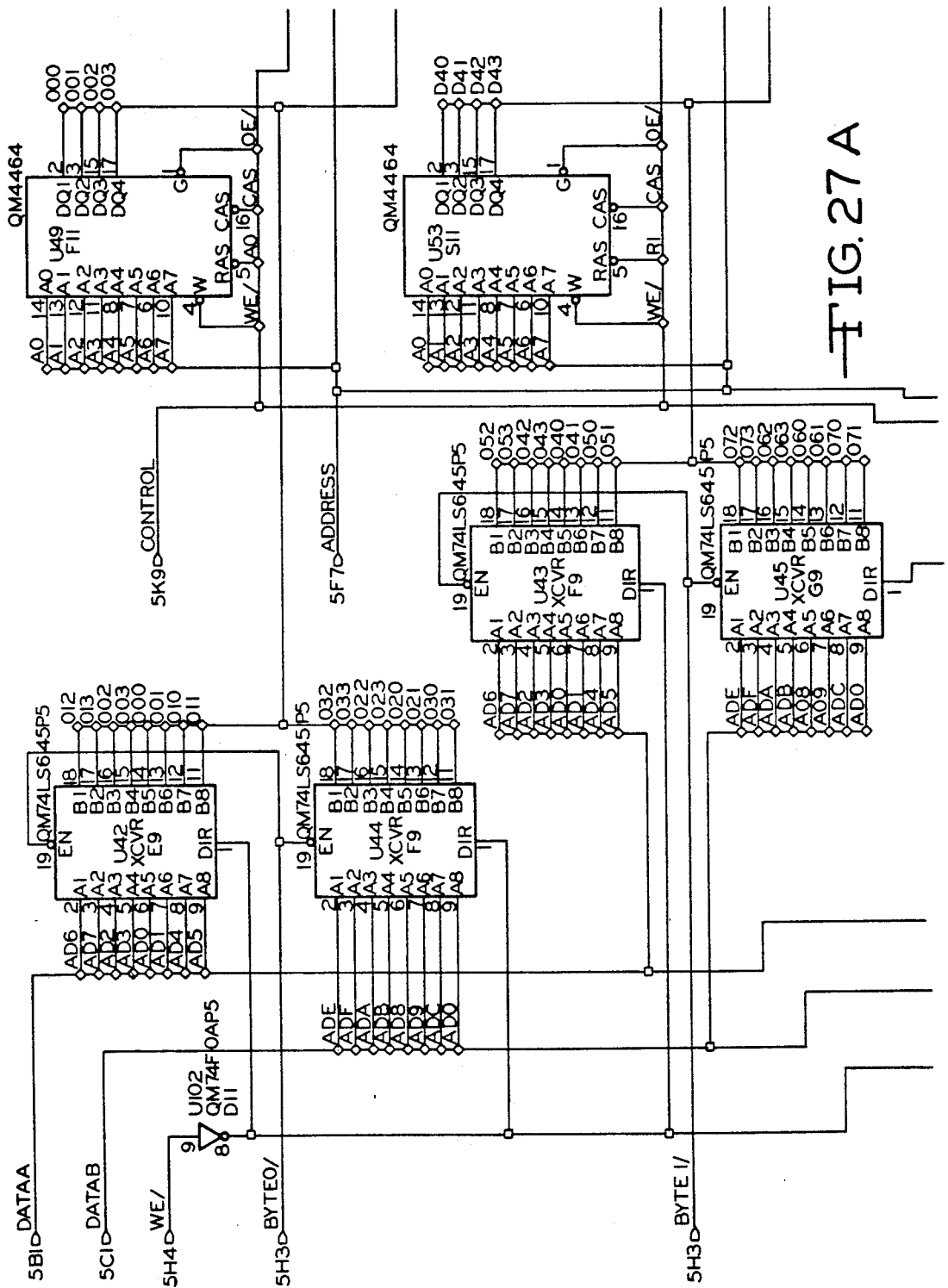
FIGS. 27A, B, C and D are schematics showing the Memory Chip Array circuitry for the Graphics Memory Array of the present invention.
Figure 27B:
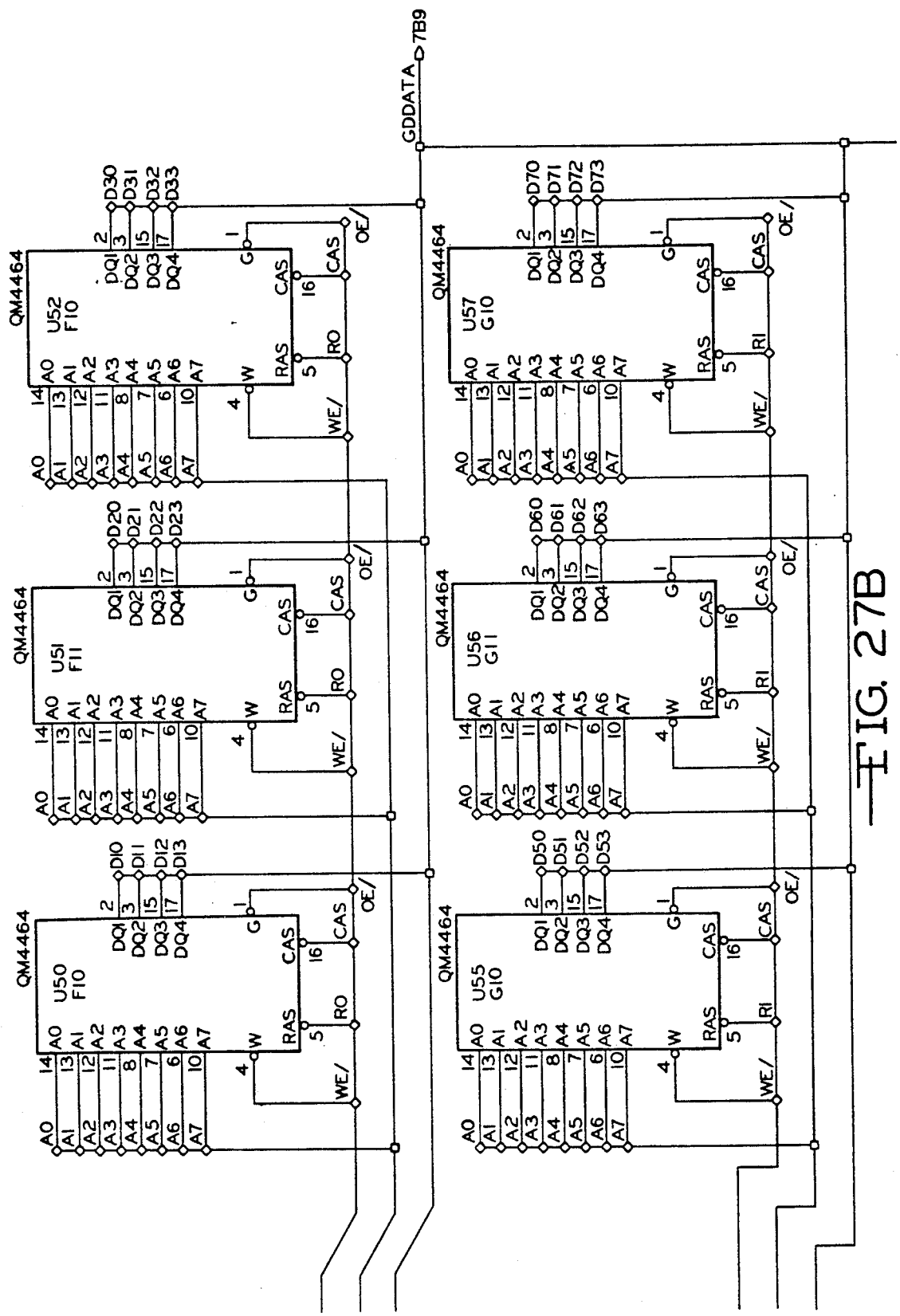
Figure 27C:
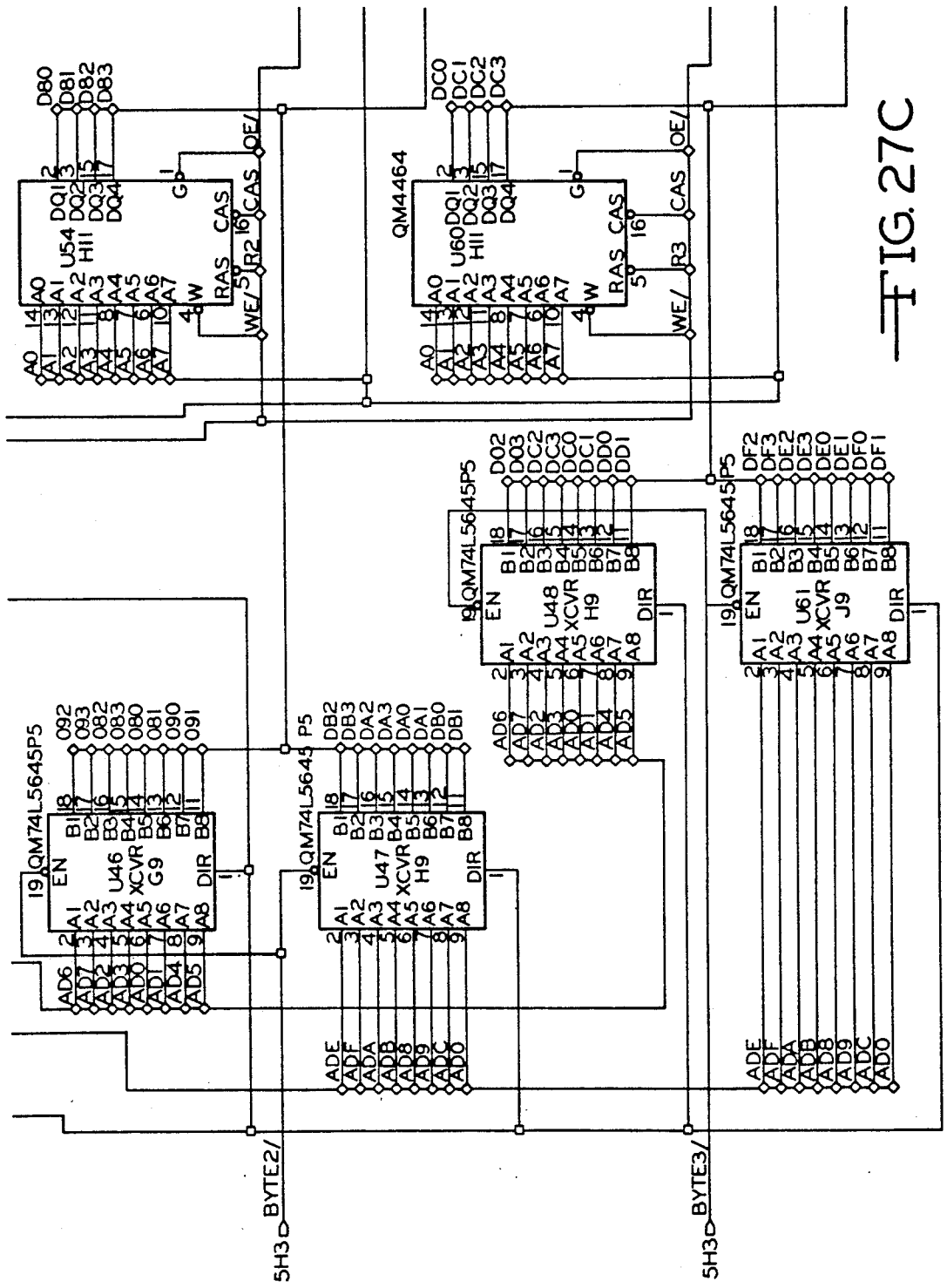
Figure 27D:
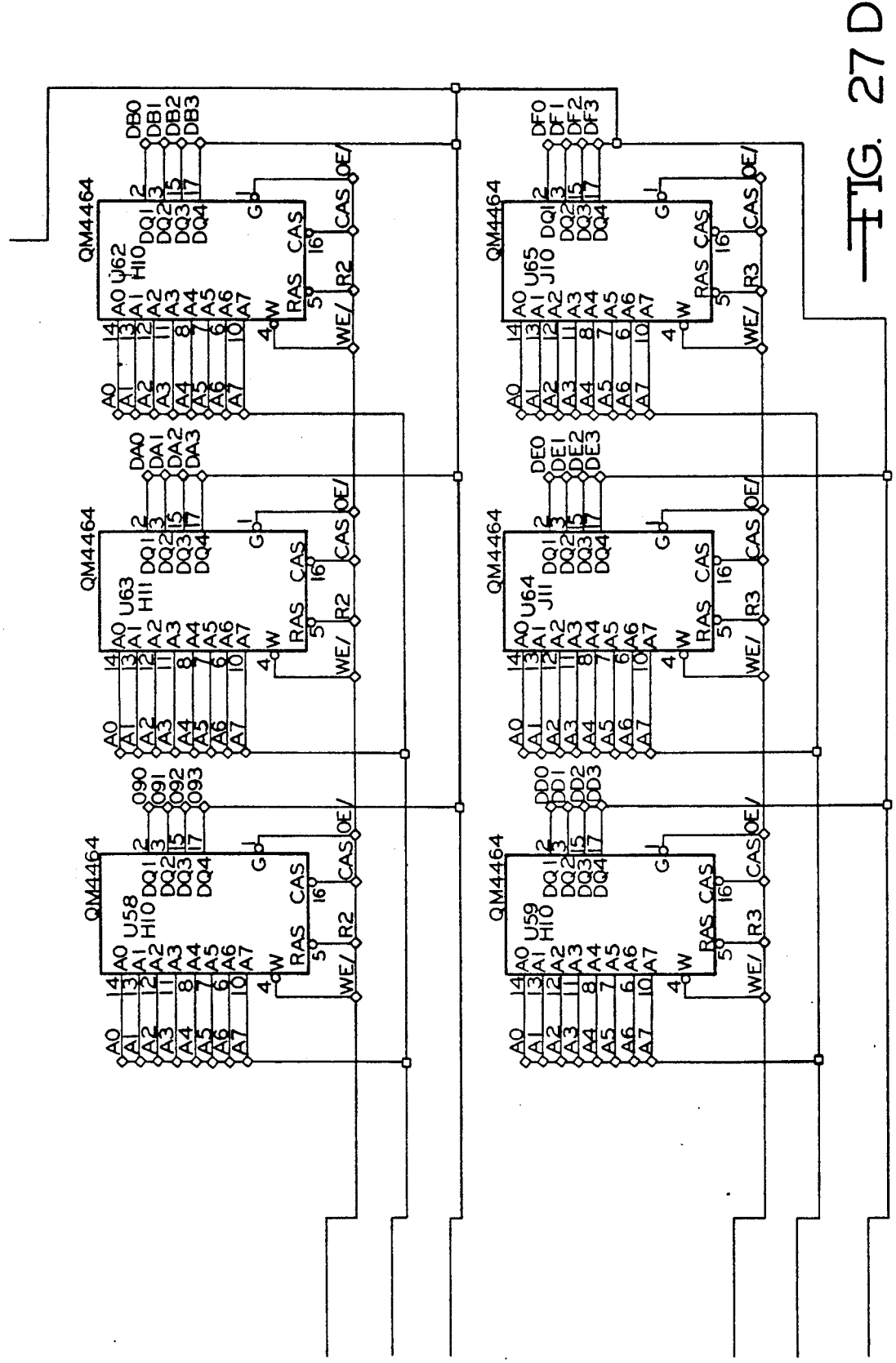

Referring to FIGS. 24-26, the CRT controller board is also VME bus compatable and has a 16 bit data bus structure accessible through a set of input/output address locations. A 512K byte graphic memory is provided. This memory is organized as a 1K×1K, 4 bit pixel memory. This organization allows for a color graphics plane where each pixel may have one of eight colors. This design supports two dimensional scrolling, zooming and graphic drawing. The CRT controller board functions as follows. At power up the controller is configured for no scrolling or zooming and the graphics plane is disabled. The input/output address is selectable from several ranges. The bit-0 of each graphics nibble is used to enable or disable an individual pixel. The remaining 3 bits are used to turn on or off the 3 primary colors of the color monitor system. This provides for 8 color combinations per pixel. Each color channel is driven by a digital/analog converter with an internal look-up table (256×8 bits). This table can be used for pseudo color displays of the image stored in memory or for certain primitive image processing algorithms. The designed display system board provides 8 bits per channel. Up to three 8 bit image plane boards may provide the input to the display system board. Therefore, 1-3 image plane boards may be used with a single display system board. The three cases are treated as follows: in an 8 bit black and white system using one image plane board the same 8 bits are used as input to the look-up tables of the red, green and blue D/A converters. If two image plane boards are used, the 16 bits per pixel and special programming hardware is provided to allow the user to chose any contiguous 8 bits for display. In the case of the three image plane boards, the overall system becomes a true color system with each image plane board providing its 8 bits to an individual color channel.

Vertical scrolling may be achieved on an every other line basis. The system is designed for interlace display and horizontal scrolling is provided for every 4 pixels due to the imaging memory organization. Image zooming is accomplished by duplication of pixels. The zooming factor is from 2 to 16. Graphics drawing is supported directly by a Hitachi video display controller (HD63484-8). Various drawings such as line, circle, ellipsis, etc., are command driven.

Figure 28A:
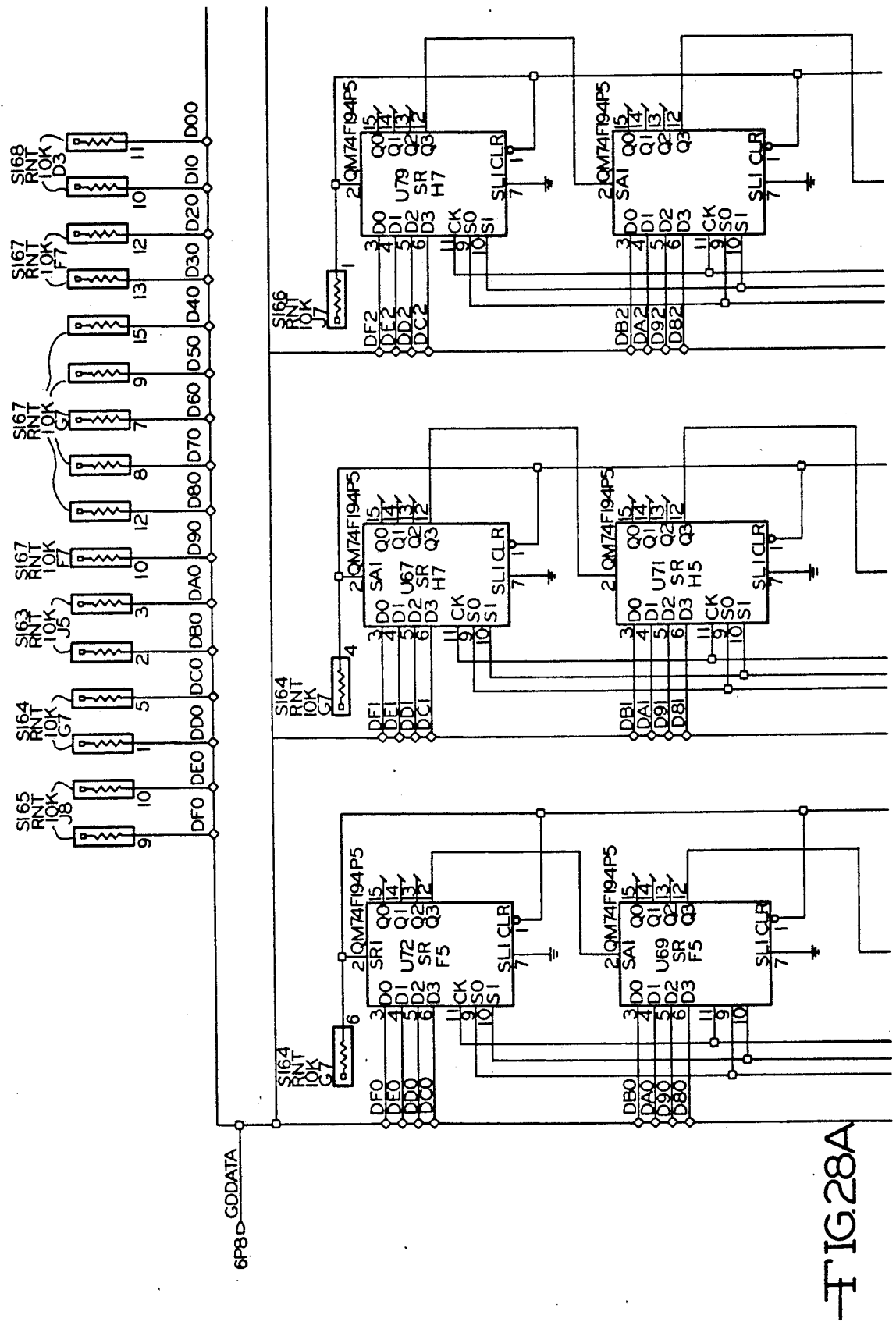
FIGS. 28A, B, C and D are schematics showing the Graphics Display and Shift Register circuitry for the Graphics Memory Array of the present invention.
Figure 28B:
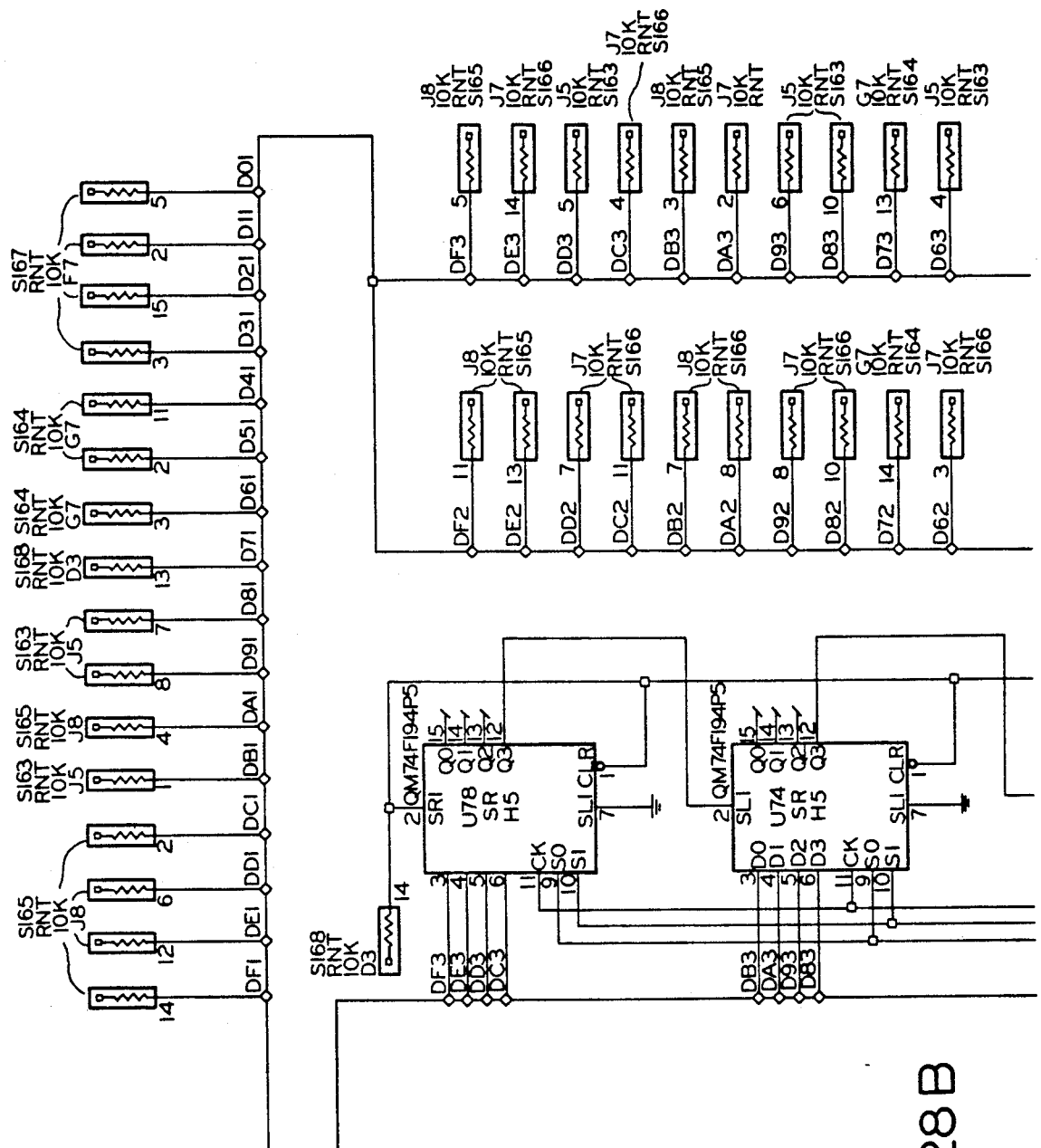
Figure 28C:
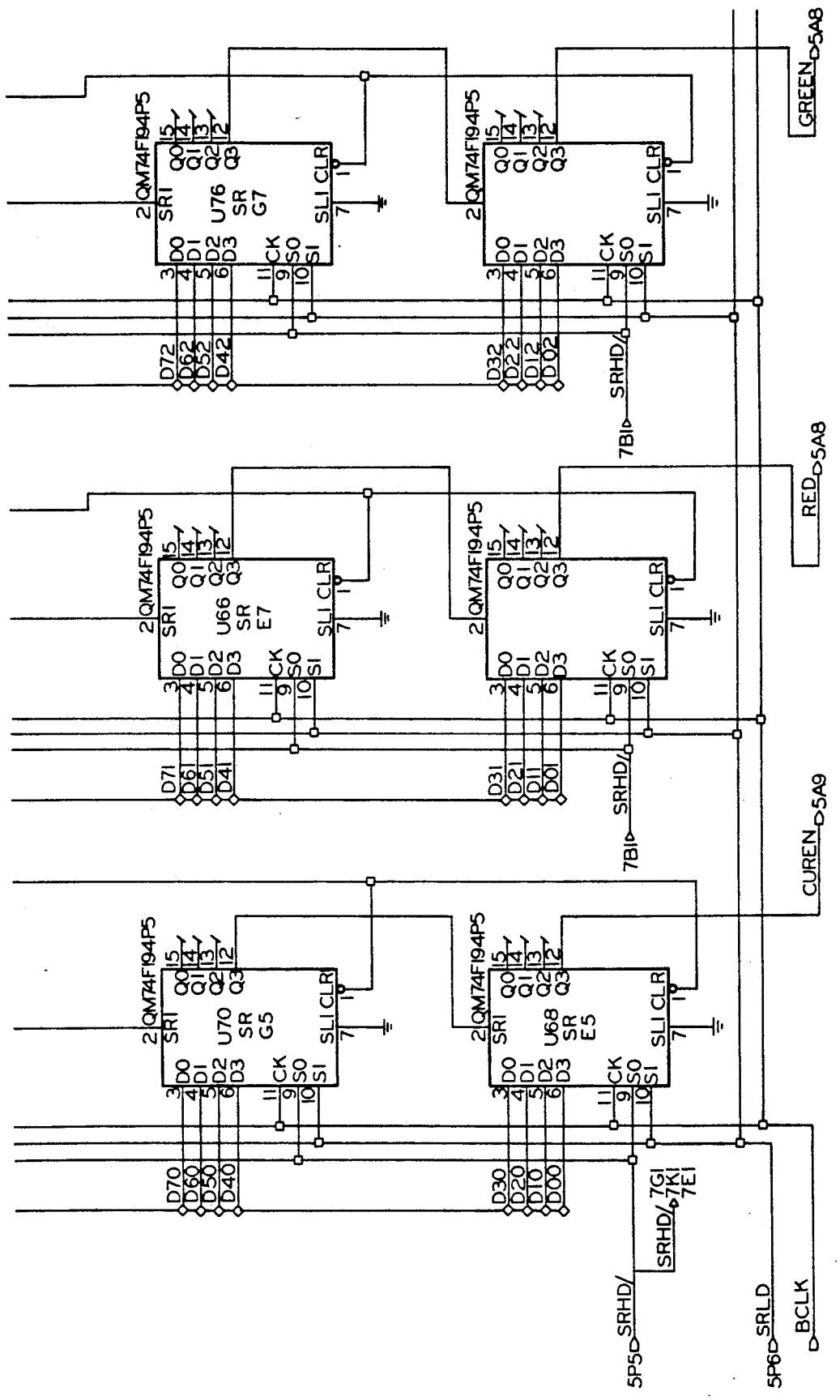
Figure 29B:
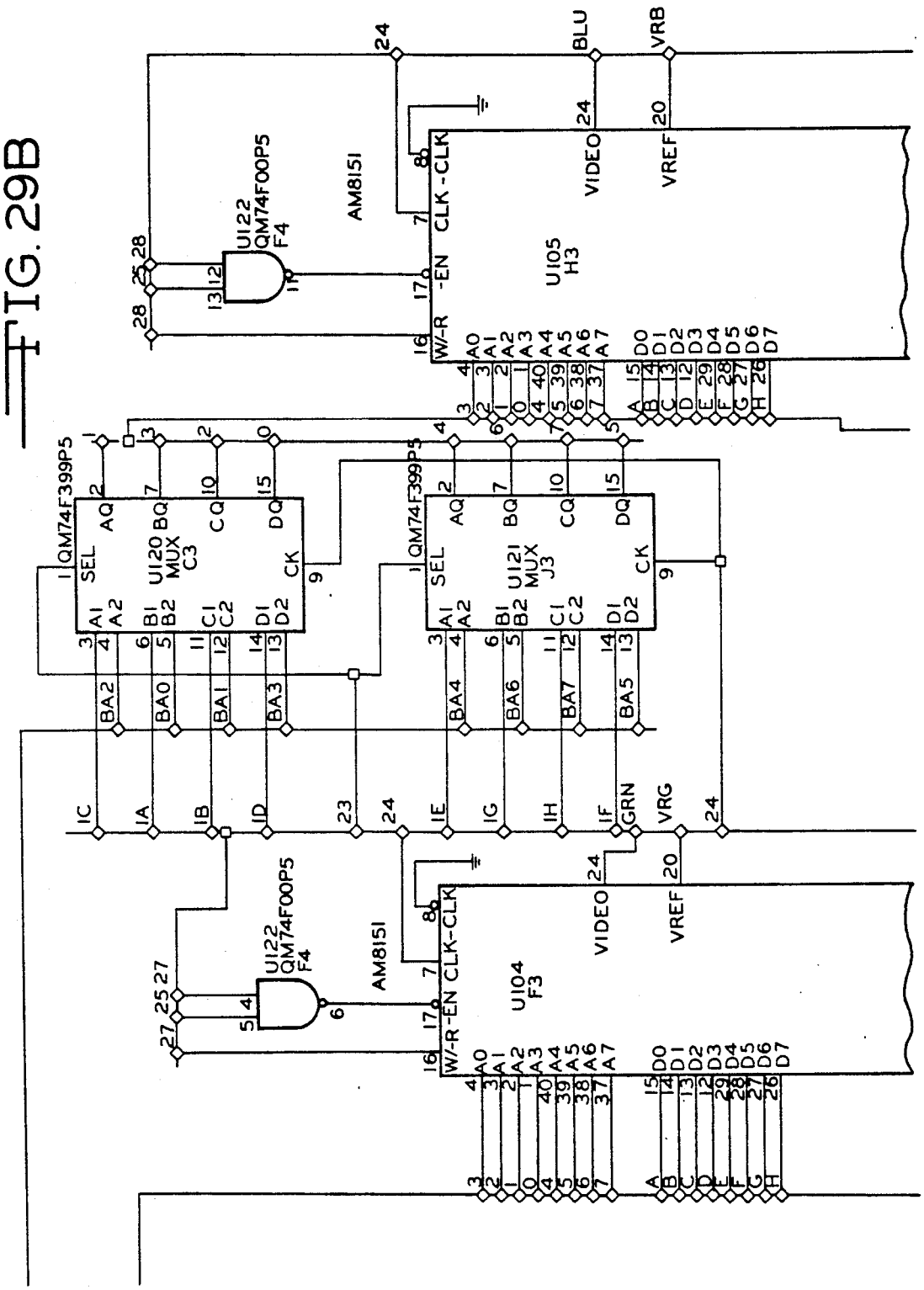
FIGS. 29A, B, C and D are schematics showing the D/A Converter circuitry for the Graphics Memory Array of the present invention.
Figure 29C:
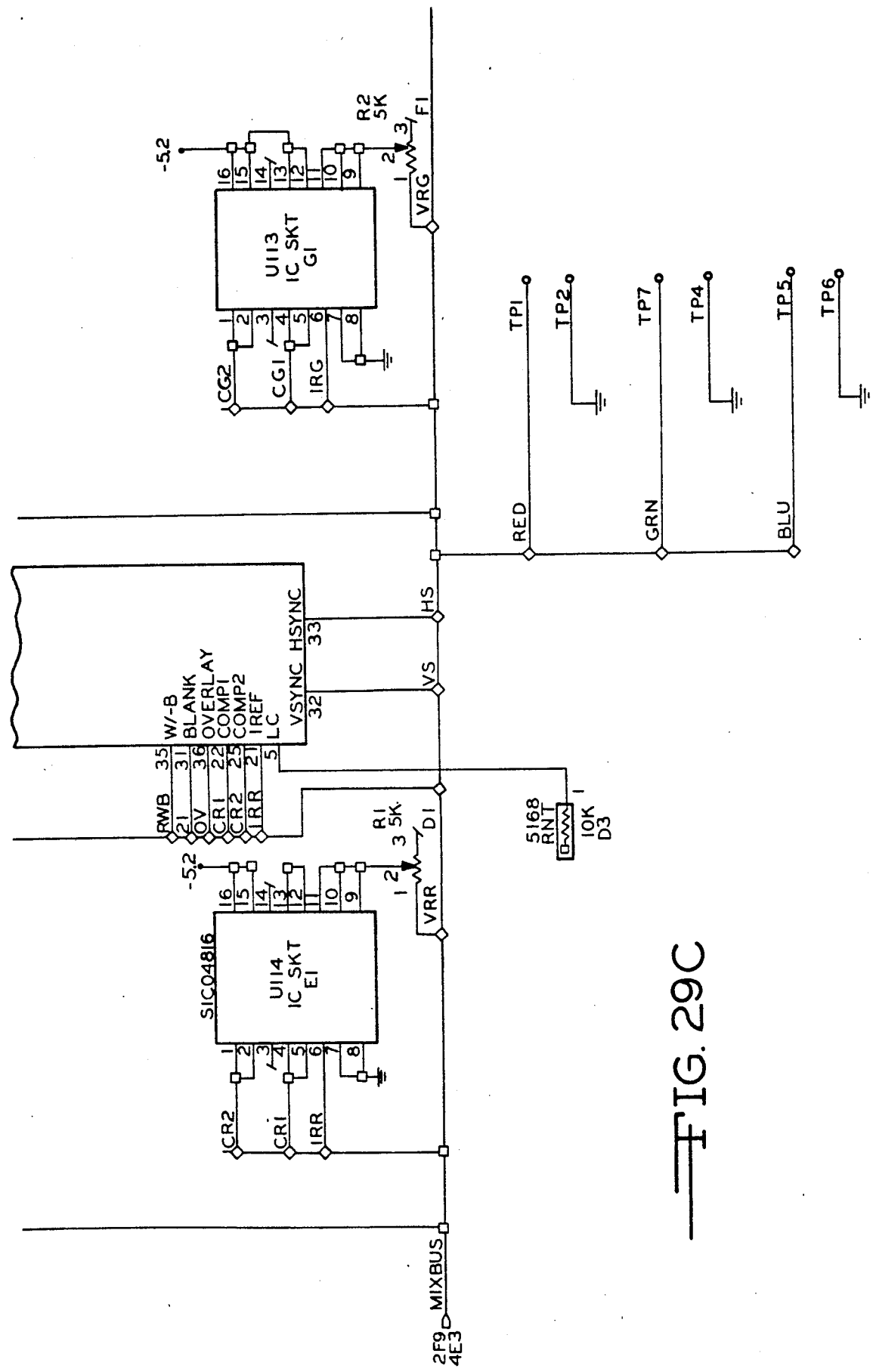
Figure 29D:
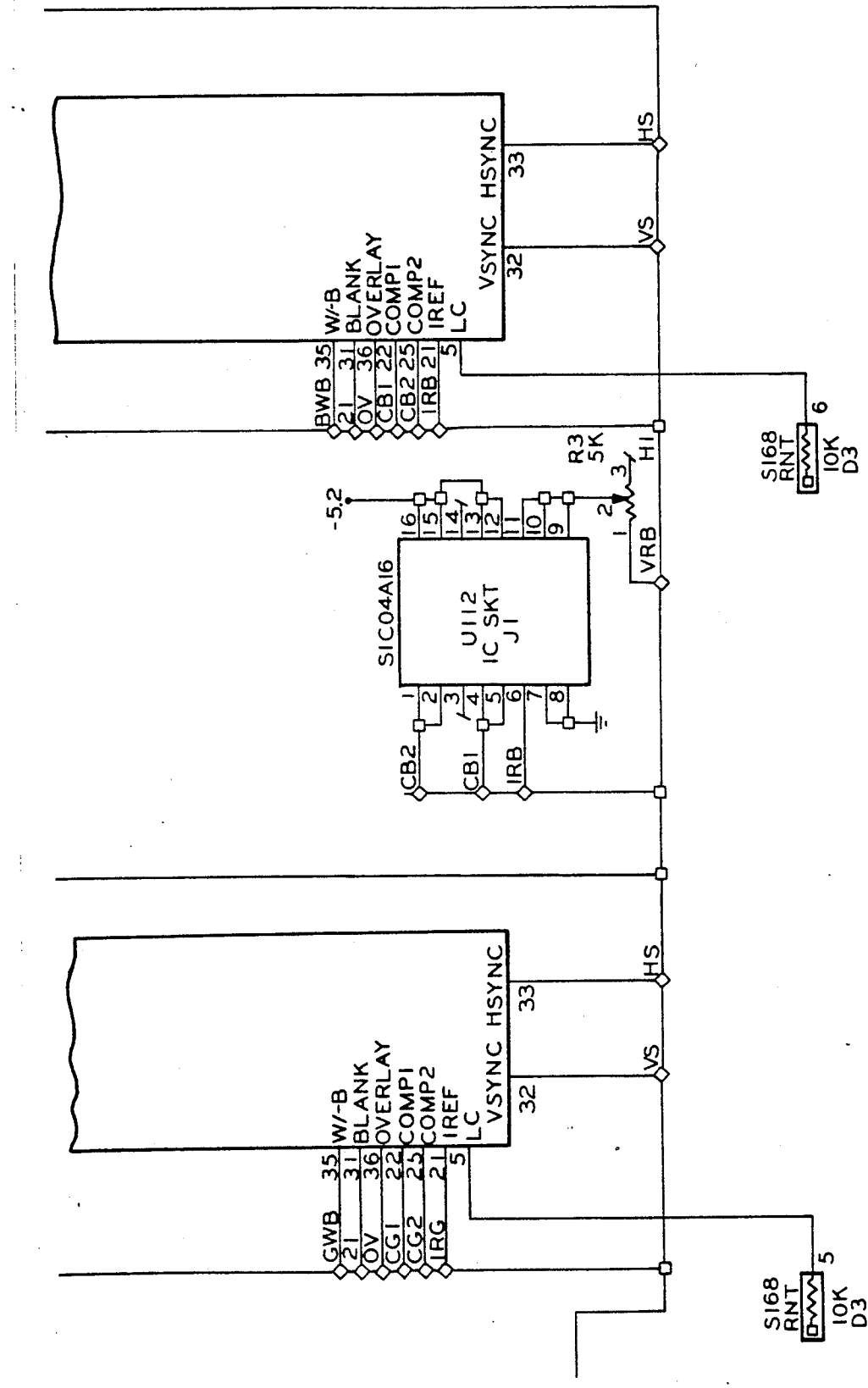

Referring to FIGS. 27-29, the graphics memory array board is connected to the CRT controller board by way of two 60 pin interboard connectors. The graphics memory array board consists of 512K bytes of DRAM memory for the graphics display. This board accepts three 8 bit video data channels, displaying the information on a CRT by using three AM8151 video D/A converters. A circuit is provided to handle any of the three special cases regarding the number of video channels. A combination circuit is provided which mixes the video (image) and graphics display information together for display. Both the video (image) and graphics can be enabled/disabled without interfering with each other.

The above description of the preferred embodiment is intended for illustrative purposes and is not intended to be limiting upon the scope and content of the following claims.

We claim:

1. An improved laser imaging apparatus comprising, in combination:
   means for generating a coherent beam of light;
   means for securing a target in a fixed position;
   a beam controller for receiving and directing such coherent beam of light into the target in a desired position to position pattern and at a desired rate of travel;
   control means for determining the pattern and rate of travel of such beam;
   an optical fiber faceplate having a selected emission cone for collecting light emission transmitted from such target;
   a dielectric interference filter having a critical angle matched relative to such emission cone of said optical fiber faceplate for receiving and blocking such beam of light and accepting all forward scatter from said faceplate;
   means for receiving and filtering such forward scatter from said dielectric filter;
   means for receiving such filtered forward scatter and generating signals as a function of the intensity and location of the forward scatter received; and
   means for receiving such signals and generating a visual display as a function of the intensity and location of such light emission.

2. The imaging apparatus of claim 1, wherein said dielectric interference filter is a Bragg Diffaction filter.

3. The imaging apparatus of claim 1, wherein said beam controller has X, Y coordinate scanning capability with a simultaneous Z coordinate correction to cause such beam to have a topographical field of focus in the plane of the target.

4. An improved laser imaging apparatus comprising, in combination:
means for generating a coherent beam of light;
means for securing a target in a fixed position;
a beam controller for receiving and directing such coherent beam of light into the target in a desired position to position pattern and at a desired rate of travel;
control means for determining such pattern and rate of travel of such beam;
a blunt-cut optical fiber faceplate having a selected emission cone and having a selected acceptance angle of a high numerical aperture to capture differences in the optical density of such light emission being transmitted from the target;
a dielectric interference filter having a critical angle matched relative to such emission cone of said optical fiber faceplate for accepting and transmitting light emission based on optical density and forward scatter;
means for receiving and filtering such light transmitted from said dielectric interference filter;
means for receiving such filtered light and generating signals as a function of the intensity and location of the light received; and,
means for receiving such signals and generating a visual display as a function of the intensity and location of such light emission.

5. The imaging apparatus of claim 4 further including a fluorescent sensor located between said dielectric interference filter and said filter means, said fluorescent sensor receiving light emission from said dielectric interference filter and creating fluorescent shadow images from said light emission.

6. The imaging apparatus of claim 4, wherein said beam controller has X, Y coordinate scanning capability with a simultaneous Z coordinate correction to cause such beam to have a topographical field of focus in the plane of the target.

7. An improved laser imaging apparatus comprising, in combination:
means for generating a coherent beam of light;
means for securing a target in a fixed position;
a beam controller for receiving and directing such coherent beam of light into the target in a desired position to position pattern and at a desired rate of travel;
control means for determining such pattern and rate of travel of such beam;
an optical fiber faceplate having a selected emission cone for collecting light emission transmitted from the target, said optical fibers of said faceplate being of a square cross section to propagate plane polarized light through fluorescence anistopy;
filter means for receiving and filtering such light collected by said faceplate;
means for receiving such filtered light and generating signals as a function of intensity and location of the light received; and,
means for receiving such signals and generating a visual display as a result of the intensity and location of such light emission.

8. The imaging apparatus of claim 7, wherein said cross sectional optical fibers include extramural light absorbing material, said material enhancing the ability of said square optical fibers to propagate plane polarized light.

9. The imaging apparatus of claim 7, wherein said beam controller has X, Y coordinate scanning capability with a simultaneous Z coordinate correction to cause such beam to have a topographical field of focus in the plane of the target.

10. An improved laser imaging apparatus comprising, in combination:
means for generating a coherent beam of light;
means for securing a target in a fixed position;
a three-dimensional beam controller for receiving and directing such coherent beam of light into the target in a desired position to position pattern and at a desired rate of travel, said beam controller having X, Y coordinate scanning capability with a simultaneous Z coordinate correction to cause such beam to have a topographical field of focus in the plane of the target;
control means for determining the three-dimensional pattern and rate of travel of such beam;
a bias-cut optical fiber faceplace having a selected acceptance angle to block any light being transmitted from the target which is outside of such acceptance angle and capture any other light emission from the target which is within such specified acceptance angle;
a dielectric interference filter having a critical angle matched relative to said selected acceptance angle of said bias-cut optical fiber faceplate to accept and transmit submicron light emission based on fluorescence and forward light scatter while blocking such beam of light;
means for receiving and filtering such submicron emission from said dielectric interference filter;
means for receiving such filtered submicron emission and generating signals as a function of the intensity and location of the fluorescence and forward light scatter comprising such submicron emission; and
means for receiving such signals and generating a visual display as a function of the intensity and location of such images.

11. The imaging apparatus of claim 10 further including a fluorescent sensor for receiving such fluorescense and forward scatter submicron emission from said dielectric interference filter and creating fluorescent shadow images in the 0.2–1.0 um range.

* * * * *